(12) United States Patent
Lillard et al.

(10) Patent No.: US 8,512,701 B2
(45) Date of Patent: Aug. 20, 2013

(54) ANTI-CXCL13 AND ANTI-CXCR5 ANTIBODIES FOR THE PREVENTION AND TREATMENT OF CANCER AND CANCER CELL MIGRATION

(75) Inventors: James W. Lillard, Smyrna, GA (US); Rajesh Singh, Atlanta, GA (US); Shailesh Singh, Powder Springs, GA (US)

(73) Assignee: Morehouse School of Medicine, Atlanta, GA (US)

( * ) Notice: Subject to any disclaimer, the term of this patent is extended or adjusted under 35 U.S.C. 154(b) by 71 days.

(21) Appl. No.: 13/248,904

(22) Filed: Sep. 29, 2011

(65) Prior Publication Data

US 2012/0128688 A1 May 24, 2012

Related U.S. Application Data

(63) Continuation-in-part of application No. 13/233,769, filed on Sep. 15, 2011, which is a continuation-in-part of application No. 12/967,273, filed on Dec. 14, 2010, now Pat. No. 8,097,250, which is a continuation of application No. 10/712,398, filed on Nov. 14, 2003, now Pat. No. 7,919,083.

(60) Provisional application No. 60/426,347, filed on Nov. 15, 2002.

(51) Int. Cl.
*A61K 39/395* (2006.01)

(52) U.S. Cl.
USPC .................................. 424/130.1; 424/174.1

(58) Field of Classification Search
None
See application file for complete search history.

(56) References Cited

U.S. PATENT DOCUMENTS

| | | | |
|---|---|---|---|
| 4,676,980 A | 6/1987 | Segal et al. | |
| 4,816,567 A | 3/1989 | Cabilly et al. | |
| 4,818,542 A | 4/1989 | DeLuca et al. | |
| 4,868,116 A | 9/1989 | Morgan et al. | |
| 4,980,286 A | 12/1990 | Morgan et al. | |
| 5,135,917 A | 8/1992 | Burch | |
| 5,168,053 A | 12/1992 | Altman et al. | |
| 5,176,996 A | 1/1993 | Hogan et al. | |
| 5,334,711 A | 8/1994 | Sproat et al. | |
| 5,476,766 A | 12/1995 | Gold et al. | |
| 5,530,101 A | 6/1996 | Queen et al. | |
| 5,543,293 A | 8/1996 | Gold et al. | |
| 5,580,967 A | 12/1996 | Joyce | |
| 5,595,873 A | 1/1997 | Joyce | |
| 5,624,824 A | 4/1997 | Yuan et al. | |
| 5,631,115 A | 5/1997 | Ohtsuka et al. | |
| 5,646,042 A | 7/1997 | Stinchcomb et al. | |
| 5,652,107 A | 7/1997 | Lizardi et al. | |
| 5,683,873 A | 11/1997 | George et al. | |
| 5,683,874 A | 11/1997 | Kool | |
| 5,728,521 A | 3/1998 | Yuan et al. | |
| 5,861,254 A | 1/1999 | Schneider et al. | |
| 5,861,288 A | 1/1999 | Usman et al. | |
| 5,869,248 A | 2/1999 | Yuan et al. | |
| 5,869,253 A | 2/1999 | Draper | |
| 5,874,566 A | 2/1999 | Veerapanane et al. | |
| 5,877,162 A | 3/1999 | Werner et al. | |
| 5,910,408 A | 6/1999 | Szostak et al. | |
| 5,962,426 A | 10/1999 | Glazer | |
| 5,989,906 A | 11/1999 | Thompson | |
| 5,994,320 A | 11/1999 | Low et al. | |
| 6,017,756 A | 1/2000 | Draper | |
| 6,022,962 A | 2/2000 | Chowrira et al. | |
| 6,030,776 A | 2/2000 | Eaton et al. | |
| 6,046,319 A | 4/2000 | Power et al. | |
| 6,051,698 A | 4/2000 | Janjic et al. | |
| 6,057,437 A | 5/2000 | Kamiya et al. | |
| 6,261,834 B1 | 7/2001 | Srivastava | |
| 6,936,248 B1 | 8/2005 | Andrew et al. | |
| 2005/0065333 A1* | 3/2005 | Seth | ............................ 536/23.5 |
| 2009/0028866 A1 | 1/2009 | Hoon et al. | |
| 2009/0215053 A1 | 8/2009 | Galon et al. | |

FOREIGN PATENT DOCUMENTS

| | | |
|---|---|---|
| WO | 89/07136 | 8/1989 |
| WO | 90/02806 | 3/1990 |
| WO | 92/03566 | 3/1992 |
| WO | 93/22434 | 11/1993 |
| WO | 95/24489 | 9/1995 |
| WO | 97/18312 | 5/1997 |
| WO | 98/58058 | 12/1998 |
| WO | 99/50461 | 10/1999 |
| WO | 00/53635 | 9/2000 |
| WO | WO 00/53635 | * 9/2000 |

OTHER PUBLICATIONS

International Search Report (Application No. PCT/US2003/036557 filed Nov. 14, 2003).
Arenberg, D., et al., "Inhibition of Interleukin-8 Reduces Tumorigenesis of Human Non-Small Cell Lung Cancer in SCID Mice", J Clin Invest, vol. 97, pp. 2792-2802 (1996).
Morrison, et al., Proc. Natl. Acad. Sci. USA 81:6851-6855 (1984).
Mulligan, Science 260:926-932 (1993).
Sun, et al., Nature genetics 8:33-41 (1994).
Cotter, et al., Curr Opin Mol Ther 5:633-644 (1999).
Scharf, et al., Results probl Cell Differ 20:125-162 (1994).
Bitter, et al., Methods in Enzymol 153:516-544 (1987).
Hammond, et al., Nature Rev Gen 2:110-119 (2001).
Sharp, Genes Dev 15:485-490 (2001).

(Continued)

*Primary Examiner* — Mark Halvorson
(74) *Attorney, Agent, or Firm* — Ping Wang; Andrews Kurth LLP

(57) ABSTRACT

Methods for prevention or inhibition of the growth or metastasis of cancer cells in a subject are disclosed. One method comprises the step of administering to the subject a therapeutically effective amount of an antibody to the chemokine CXCL13 and/or the chemokine receptor CXCR5. Another method comprises the step of administering to the subject a therapeutically effective amount of an expression vector that expresses an antibody to the chemokine CXCL13 and/or the chemokine receptor CXCR5.

13 Claims, 33 Drawing Sheets

(56) References Cited

OTHER PUBLICATIONS

Waterhouse, et al., Proc. Natl. Acad. Sci. USA 95(23):13959-13964 (1998).
Marro, et al., Biochem biophys Res Commun. Oct. 13, 2006; 349:270:276.
Forster, et al., Science 238:407-409 (1990).
Yuan, et al., Proc. Natl. Acad. Sci. USA 89:8006-8010 (1992).
Yuan, et al., Embo J 14:159-168 (1995).
Carrara, et al., Proc. Natl. Acad. Sci. USA 92:2627-2631 (1995).
A.H. Kibbe Handbook of Pharmaceutical Excipients, 3rd ed. Pharmaceutical Press, London, UK (2000).
Zlotnik, "Chemokines and Cancer," International Journal of Cancer, 2006, pp. 2026-2029, vol. 119.
Johnson et al., "CCL25-CCR9 interaction modulates ovarian cancer cell migration, metalloproteinase expression, and invasion," World Journal of Surgical Oncology, 2010, pp. 1-10; vol. 8—No. 62.
Singh et al., "Expression and Functional Role of CCR9 in Prostate Cancer Cell Migration and Invasion," Clinical Cancer Research, Dec. 15, 2004, pp. 8743-8750, vol. 10.
Panse et al., "Chemokine CXCL13 is overexpressed in the tumour tissue and in the peripheral blood of breast cancer patients," British Journal of Cancer, 2008, pp. 930-938, vol. 99.
Meijer et al., "The CXCR5 Chemokine Receptor is Expressed by Carcinoma Cells and Promotes Growth of Colon Carcinoma in the Liver," Cancer Research, Oct. 1, 2006, pp. 9576-9582, vol. 66.
International Search Report and Written Opinion of the International Searching Authority issued in International Patent Application No. PCT/US2011/064653 mailed Dec. 3, 2012.

\* cited by examiner

CXCL13 blockade inhibits change in bone mineral density (BMD) induced by prostate cancer

SEQUENCE LISTING

```
<160> NUMBER OF SEQ ID NOS: 115

<210> SEQ ID NO 1
<211> LENGTH: 350
<212> TYPE: PRT
<213> ORGANISM: Homo sapiens

<400> SEQUENCE: 1

Met Ser Asn Ile Thr Asp Pro Gln Met Trp Asp Phe Asp Leu Asn
1               5                   10                  15

Phe Thr Gly Met Pro Pro Ala Asp Glu Asp Tyr Ser Pro Cys Met Leu
                20                  25                  30

Glu Thr Glu Thr Leu Asn Lys Tyr Val Val Ile Ile Ala Tyr Ala Leu
            35                  40                  45

Val Phe Leu Leu Ser Leu Leu Gly Asn Ser Leu Val Met Leu Val Ile
        50                  55                  60
```

Leu Tyr Ser Arg Val Gly Arg Ser Val Thr Asp Val Tyr Leu Leu Asn
65                  70                  75                  80

Leu Ala Leu Ala Asp Leu Leu Phe Ala Leu Thr Leu Pro Ile Trp Ala
                85                  90                  95

Ala Ser Lys Val Asn Gly Trp Ile Phe Gly Thr Phe Leu Cys Lys Val
            100                 105                 110

Val Ser Leu Leu Lys Glu Val Asn Phe Tyr Ser Gly Ile Leu Leu Leu
        115                 120                 125

Ala Cys Ile Ser Val Asp Arg Tyr Leu Ala Ile Val His Ala Thr Arg
    130                 135                 140

Thr Leu Thr Gln Lys Arg His Leu Val Lys Phe Val Cys Leu Gly Cys
145                 150                 155                 160

Trp Gly Leu Ser Met Asn Leu Ser Leu Pro Phe Phe Leu Phe Arg Gln
                165                 170                 175

Ala Tyr His Pro Asn Asn Ser Ser Pro Val Cys Tyr Glu Val Leu Gly
            180                 185                 190

Asn Asp Thr Ala Lys Trp Arg Met Val Leu Arg Ile Leu Pro His Thr
        195                 200                 205

Phe Gly Phe Ile Val Pro Leu Phe Val Met Leu Phe Cys Tyr Gly Phe
    210                 215                 220

Thr Leu Arg Thr Leu Phe Lys Ala His Met Gly Gln Lys His Arg Ala
225                 230                 235                 240

Met Arg Val Ile Phe Ala Val Val Leu Ile Phe Leu Leu Cys Trp Leu
                245                 250                 255

Pro Tyr Asn Leu Val Leu Leu Ala Asp Thr Leu Met Arg Thr Gln Val
            260                 265                 270

Ile Gln Glu Ser Cys Glu Arg Arg Asn Asn Ile Gly Arg Ala Leu Asp
        275                 280                 285

Ala Thr Glu Ile Leu Gly Phe Leu His Ser Cys Leu Asn Pro Ile Ile
    290                 295                 300

Tyr Ala Phe Ile Gly Gln Asn Phe Arg His Gly Phe Leu Lys Ile Leu
305                 310                 315                 320

Ala Met His Gly Leu Val Ser Lys Glu Phe Leu Ala Arg His Arg Val
                325                 330                 335

Thr Ser Tyr Thr Ser Ser Ser Val Asn Val Ser Ser Asn Leu
            340                 345                 350

<210> SEQ ID NO 2
<211> LENGTH: 360
<212> TYPE: PRT
<213> ORGANISM: Homo sapiens

<400> SEQUENCE: 2

Met Glu Asp Phe Asn Met Glu Ser Asp Ser Phe Glu Asp Phe Trp Lys
1               5                   10                  15

Gly Glu Asp Leu Ser Asn Tyr Ser Tyr Ser Ser Thr Leu Pro Pro Phe
            20                  25                  30

Leu Leu Asp Ala Ala Pro Cys Glu Pro Glu Ser Leu Glu Ile Asn Lys
        35                  40                  45

Tyr Phe Val Val Ile Ile Tyr Ala Leu Val Phe Leu Leu Ser Leu Leu
    50                  55                  60

Gly Asn Ser Leu Val Met Leu Val Ile Leu Tyr Ser Arg Val Gly Arg
65                  70                  75                  80

Ser Val Thr Asp Val Tyr Leu Leu Asn Leu Ala Leu Ala Asp Leu Leu
                85                  90                  95

Phe Ala Leu Thr Leu Pro Ile Trp Ala Ala Ser Lys Val Asn Gly Trp
                100                 105                 110

Ile Phe Gly Thr Phe Leu Cys Lys Val Val Ser Leu Leu Lys Glu Val
            115                 120                 125

Asn Phe Tyr Ser Gly Ile Leu Leu Ala Cys Ile Ser Val Asp Arg
        130                 135                 140

Tyr Leu Ala Ile Val His Ala Thr Arg Thr Leu Thr Gln Lys Arg Tyr
145                 150                 155                 160

Leu Val Lys Phe Ile Cys Leu Ser Ile Trp Gly Leu Ser Leu Leu Leu
                165                 170                 175

Ala Leu Pro Val Leu Leu Phe Arg Arg Thr Val Tyr Ser Ser Asn Val
            180                 185                 190

Ser Pro Ala Cys Tyr Glu Asp Met Gly Asn Asn Thr Ala Asn Trp Arg
        195                 200                 205

Met Leu Leu Arg Ile Leu Pro Gln Ser Phe Gly Phe Ile Val Pro Leu
210                 215                 220

Leu Ile Met Leu Phe Cys Tyr Gly Phe Thr Leu Arg Thr Leu Phe Lys
225                 230                 235                 240

Ala His Met Gly Gln Lys His Arg Ala Met Arg Val Ile Phe Ala Val
                245                 250                 255

Val Leu Ile Phe Leu Leu Cys Trp Leu Pro Tyr Asn Leu Val Leu Leu
            260                 265                 270

Ala Asp Thr Leu Met Arg Thr Gln Val Ile Gln Glu Thr Cys Glu Arg
        275                 280                 285

Arg Asn His Ile Asp Arg Ala Leu Asp Ala Thr Glu Ile Leu Gly Ile
290                 295                 300

Leu His Ser Cys Leu Asn Pro Leu Ile Tyr Ala Phe Ile Gly Gln Lys
305                 310                 315                 320

Phe Arg His Gly Leu Leu Lys Ile Leu Ala Ile His Gly Leu Ile Ser
                325                 330                 335

Lys Asp Ser Leu Pro Lys Asp Ser Arg Pro Ser Phe Val Gly Ser Ser
            340                 345                 350

Ser Gly His Thr Ser Thr Thr Leu
        355                 360

<210> SEQ ID NO 3
<211> LENGTH: 107
<212> TYPE: PRT
<213> ORGANISM: Homo sapiens

<400> SEQUENCE: 3

Met Ala Arg Ala Ala Leu Ser Ala Ala Pro Ser Asn Pro Arg Leu Leu
1               5                   10                  15

Arg Val Ala Leu Leu Leu Leu Leu Val Ala Ala Gly Arg Arg Ala
            20                  25                  30

Ala Gly Ala Ser Val Ala Thr Glu Leu Arg Cys Gln Cys Leu Gln Thr
        35                  40                  45

Leu Gln Gly Ile His Pro Lys Asn Ile Gln Ser Val Asn Val Lys Ser
    50                  55                  60

Pro Gly Pro His Cys Ala Gln Thr Glu Val Ile Ala Thr Leu Lys Asn
65                  70                  75                  80

Gly Arg Lys Ala Cys Leu Asn Pro Ala Ser Pro Ile Val Lys Lys Ile
                85                  90                  95

Ile Glu Lys Met Leu Asn Ser Asp Lys Ser Asn
            100                 105

<210> SEQ ID NO 4
<211> LENGTH: 107
<212> TYPE: PRT
<213> ORGANISM: Homo sapiens

<400> SEQUENCE: 4

```
Met Ala Arg Ala Thr Leu Ser Ala Ala Pro Ser Asn Pro Arg Leu Leu
1               5                   10                  15
Arg Val Ala Leu Leu Leu Leu Leu Val Ala Ala Ser Arg Arg Ala
            20                  25                  30
Ala Gly Ala Pro Leu Ala Thr Glu Leu Arg Cys Gln Cys Leu Gln Thr
        35                  40                  45
Leu Gln Gly Ile His Leu Lys Asn Ile Gln Ser Val Lys Val Lys Ser
    50                  55                  60
Pro Gly Pro His Cys Ala Gln Thr Glu Val Ile Ala Thr Leu Lys Asn
65                  70                  75                  80
Gly Gln Lys Ala Cys Leu Asn Pro Ala Ser Pro Met Val Lys Lys Ile
                85                  90                  95
Ile Glu Lys Met Leu Lys Asn Gly Lys Ser Asn
                100                 105
```

<210> SEQ ID NO 5
<211> LENGTH: 107
<212> TYPE: PRT
<213> ORGANISM: Homo sapiens

<400> SEQUENCE: 5

```
Met Ala His Ala Thr Leu Ser Ala Ala Pro Ser Asn Pro Arg Leu Leu
1               5                   10                  15
Arg Val Ala Leu Leu Leu Leu Leu Val Ala Ala Ser Arg Arg Ala
            20                  25                  30
Ala Gly Ala Ser Val Val Thr Glu Leu Arg Cys Gln Cys Leu Gln Thr
        35                  40                  45
Leu Gln Gly Ile His Leu Lys Asn Ile Gln Ser Val Asn Val Arg Ser
    50                  55                  60
Pro Gly Pro His Cys Ala Gln Thr Glu Val Ile Ala Thr Leu Lys Asn
65                  70                  75                  80
Gly Lys Lys Ala Cys Leu Asn Pro Ala Ser Pro Met Val Gln Lys Ile
                85                  90                  95
Ile Glu Lys Ile Leu Asn Lys Gly Ser Thr Asn
                100                 105
```

<210> SEQ ID NO 6
<211> LENGTH: 114
<212> TYPE: PRT
<213> ORGANISM: Homo sapiens

<400> SEQUENCE: 6

```
Met Ser Leu Leu Ser Ser Arg Ala Ala Arg Val Pro Gly Pro Ser Ser
1               5                   10                  15
Ser Leu Cys Ala Leu Leu Val Leu Leu Leu Leu Thr Gln Pro Gly
            20                  25                  30
Pro Ile Ala Ser Ala Gly Pro Ala Ala Val Leu Arg Glu Leu Arg
        35                  40                  45
Cys Val Cys Leu Gln Thr Thr Gln Gly Val His Pro Lys Met Ile Ser
    50                  55                  60
Asn Leu Gln Val Phe Ala Ile Gly Pro Gln Cys Ser Lys Val Glu Val
```

```
                  65                  70                  75                  80
Val Ala Ser Leu Lys Asn Gly Lys Glu Ile Cys Leu Asp Pro Glu Ala
                  85                  90                  95

Pro Phe Leu Lys Lys Val Ile Gln Lys Ile Leu Asp Gly Gly Asn Lys
               100                 105                 110

Glu Asn

<210> SEQ ID NO 7
<211> LENGTH: 114
<212> TYPE: PRT
<213> ORGANISM: Homo sapiens

<400> SEQUENCE: 7

Met Ser Leu Pro Ser Ser Arg Ala Ala Arg Val Pro Gly Pro Ser Gly
  1               5                  10                  15

Ser Leu Cys Ala Leu Leu Ala Leu Leu Leu Leu Thr Pro Pro Gly
                 20                  25                  30

Pro Leu Ala Ser Ala Gly Pro Val Ser Ala Val Leu Thr Glu Leu Arg
                 35                  40                  45

Cys Thr Cys Leu Arg Val Thr Leu Arg Val Asn Pro Lys Thr Ile Gly
             50                  55                  60

Lys Leu Gln Val Phe Pro Ala Gly Pro Gln Cys Ser Lys Val Glu Val
 65                  70                  75                  80

Val Ala Ser Leu Lys Asn Gly Lys Gln Val Cys Leu Asp Pro Glu Ala
                  85                  90                  95

Pro Phe Leu Lys Lys Val Ile Gln Lys Ile Leu Asp Ser Gly Asn Lys
               100                 105                 110

Lys Asn

<210> SEQ ID NO 8
<211> LENGTH: 128
<212> TYPE: PRT
<213> ORGANISM: Homo sapiens

<400> SEQUENCE: 8

Met Ser Leu Arg Leu Asp Thr Thr Pro Ser Cys Asn Ser Ala Arg Pro
  1               5                  10                  15

Leu His Ala Leu Gln Val Leu Leu Leu Ser Leu Leu Leu Thr Ala
                 20                  25                  30

Leu Ala Ser Ser Thr Lys Gly Gln Thr Lys Arg Asn Leu Ala Lys Gly
                 35                  40                  45

Lys Glu Glu Ser Leu Asp Ser Asp Leu Tyr Ala Glu Leu Arg Cys Met
         50                  55                  60

Cys Ile Lys Thr Thr Ser Gly Ile His Pro Lys Asn Ile Gln Ser Leu
 65                  70                  75                  80

Glu Val Ile Gly Lys Gly Thr His Cys Asn Gln Val Glu Val Ile Ala
                  85                  90                  95

Thr Leu Lys Asp Gly Arg Lys Ile Cys Leu Asp Pro Asp Ala Pro Arg
               100                 105                 110

Ile Lys Lys Ile Val Gln Lys Lys Leu Ala Gly Asp Glu Ser Ala Asp
             115                 120                 125

<210> SEQ ID NO 9
<211> LENGTH: 99
<212> TYPE: PRT
<213> ORGANISM: Homo sapiens

<400> SEQUENCE: 9
```

```
Met Thr Ser Lys Leu Ala Val Ala Leu Leu Ala Ala Phe Leu Ile Ser
1               5                   10                  15

Ala Ala Leu Cys Glu Gly Ala Val Leu Pro Arg Ser Ala Lys Glu Leu
            20                  25                  30

Arg Cys Gln Cys Ile Lys Thr Tyr Ser Lys Pro Phe His Pro Lys Phe
            35                  40                  45

Ile Lys Glu Leu Arg Val Ile Glu Ser Gly Pro His Cys Ala Asn Thr
50                  55                  60

Glu Ile Ile Val Lys Leu Ser Asp Gly Arg Glu Leu Cys Leu Asp Pro
65                  70                  75                  80

Lys Glu Asn Trp Val Gln Arg Val Val Glu Lys Phe Leu Lys Arg Ala
                85                  90                  95

Glu Asn Ser
```

<210> SEQ ID NO 10
<211> LENGTH: 352
<212> TYPE: PRT
<213> ORGANISM: Homo sapiens

<400> SEQUENCE: 10

```
Met Glu Gly Ile Ser Ile Tyr Thr Ser Asp Asn Tyr Thr Glu Glu Met
1               5                   10                  15

Gly Ser Gly Asp Tyr Asp Ser Met Lys Glu Pro Cys Phe Arg Glu Glu
            20                  25                  30

Asn Ala Asn Phe Asn Lys Ile Phe Leu Pro Thr Ile Tyr Ser Ile Ile
            35                  40                  45

Phe Leu Thr Gly Ile Val Gly Asn Gly Leu Val Ile Leu Val Met Gly
50                  55                  60

Tyr Gln Lys Lys Leu Arg Ser Met Thr Asp Lys Tyr Arg Leu His Leu
65                  70                  75                  80

Ser Val Ala Asp Leu Leu Phe Val Ile Thr Leu Pro Phe Trp Ala Val
                85                  90                  95

Asp Ala Val Ala Asn Trp Tyr Phe Gly Asn Phe Leu Cys Lys Ala Val
            100                 105                 110

His Val Ile Tyr Thr Val Asn Leu Tyr Ser Ser Val Leu Ile Leu Ala
            115                 120                 125

Phe Ile Ser Leu Asp Arg Tyr Leu Ala Ile Val His Ala Thr Asn Ser
130                 135                 140

Gln Arg Pro Arg Lys Leu Leu Ala Glu Lys Val Val Tyr Val Gly Val
145                 150                 155                 160

Trp Ile Pro Ala Leu Leu Leu Thr Ile Pro Asp Phe Ile Phe Ala Asn
                165                 170                 175

Val Ser Glu Ala Asp Asp Arg Tyr Ile Cys Asp Arg Phe Tyr Pro Asn
            180                 185                 190

Asp Leu Trp Val Val Phe Gln Phe Gln His Ile Met Val Gly Leu
            195                 200                 205

Ile Leu Pro Gly Ile Val Ile Leu Ser Cys Tyr Cys Ile Ile Ile Ser
210                 215                 220

Lys Leu Ser His Ser Lys Gly His Gln Lys Arg Lys Ala Leu Lys Thr
225                 230                 235                 240

Thr Val Ile Leu Ile Leu Ala Phe Phe Ala Cys Trp Leu Pro Tyr Tyr
                245                 250                 255

Ile Gly Ile Ser Ile Asp Ser Phe Ile Leu Leu Glu Ile Ile Lys Gln
            260                 265                 270
```

```
Gly Cys Glu Phe Glu Asn Thr Val His Lys Trp Ile Ser Ile Thr Glu
            275                 280                 285

Ala Leu Ala Phe Phe His Cys Cys Leu Asn Pro Ile Leu Tyr Ala Phe
        290                 295                 300

Leu Gly Ala Lys Phe Lys Thr Ser Ala Gln His Ala Leu Thr Ser Val
305                 310                 315                 320

Ser Arg Gly Ser Ser Leu Lys Ile Leu Ser Lys Gly Lys Arg Gly Gly
                325                 330                 335

His Ser Ser Val Ser Thr Glu Ser Glu Ser Ser Phe His Ser Ser
                340                 345                 350
```

<210> SEQ ID NO 11
<211> LENGTH: 93
<212> TYPE: PRT
<213> ORGANISM: Homo sapiens

<400> SEQUENCE: 11

```
Met Asn Ala Lys Val Val Val Leu Val Leu Val Leu Thr Ala Leu
1               5                   10                  15

Cys Leu Ser Asp Gly Lys Pro Val Ser Leu Ser Tyr Arg Cys Pro Cys
                20                  25                  30

Arg Phe Phe Glu Ser His Val Ala Arg Ala Asn Val Lys His Leu Lys
            35                  40                  45

Ile Leu Asn Thr Pro Asn Cys Ala Leu Gln Ile Val Ala Arg Leu Lys
        50                  55                  60

Asn Asn Asn Arg Gln Val Cys Ile Asp Pro Lys Leu Lys Trp Ile Gln
65                  70                  75                  80

Glu Tyr Leu Glu Lys Ala Leu Asn Lys Arg Phe Lys Met
                85                  90
```

<210> SEQ ID NO 12
<211> LENGTH: 327
<212> TYPE: PRT
<213> ORGANISM: Homo sapiens

<400> SEQUENCE: 12

```
Met Ala Ser Phe Lys Ala Val Phe Val Pro Val Ala Tyr Ser Leu Ile
1               5                   10                  15

Phe Leu Leu Gly Val Ile Gly Asn Val Leu Val Leu Val Ile Leu Glu
                20                  25                  30

Arg His Arg Gln Thr Arg Ser Ser Thr Glu Thr Phe Leu Phe His Leu
            35                  40                  45

Ala Val Ala Asp Leu Leu Leu Val Phe Ile Leu Pro Phe Ala Val Ala
        50                  55                  60

Glu Gly Ser Val Gly Trp Val Leu Gly Thr Phe Leu Cys Lys Thr Val
65                  70                  75                  80

Ile Ala Leu His Lys Val Asn Phe Tyr Cys Ser Ser Leu Leu Leu Ala
                85                  90                  95

Cys Ile Ala Val Asp Arg Tyr Leu Ala Ile Val His Ala Val His Ala
                100                 105                 110

Tyr Arg His Arg Arg Leu Leu Ser Ile His Ile Thr Cys Gly Thr Ile
            115                 120                 125

Trp Leu Val Gly Phe Leu Leu Ala Leu Pro Glu Ile Leu Phe Ala Lys
        130                 135                 140

Val Ser Gln Gly His His Asn Asn Ser Leu Pro Arg Cys Thr Phe Ser
145                 150                 155                 160

Gln Glu Asn Gln Ala Glu Thr His Ala Trp Phe Thr Ser Arg Phe Leu
```

```
                165                 170                 175
Tyr His Val Ala Gly Phe Leu Leu Pro Met Leu Val Met Gly Trp Cys
            180                 185                 190

Tyr Val Gly Val Val His Arg Leu Arg Gln Ala Gln Arg Arg Pro Gln
        195                 200                 205

Arg Gln Lys Ala Val Arg Val Ala Ile Leu Val Thr Ser Ile Phe Phe
    210                 215                 220

Leu Cys Trp Ser Pro Tyr His Ile Val Ile Phe Leu Asp Thr Leu Ala
225                 230                 235                 240

Arg Leu Lys Ala Val Asp Asn Thr Cys Lys Leu Asn Gly Ser Leu Pro
                245                 250                 255

Val Ala Ile Thr Met Cys Glu Phe Leu Gly Leu Ala His Cys Cys Leu
            260                 265                 270

Asn Pro Met Leu Tyr Thr Phe Ala Gly Val Lys Phe Arg Ser Asp Leu
        275                 280                 285

Ser Arg Leu Leu Thr Lys Leu Gly Cys Thr Gly Pro Ala Ser Leu Cys
    290                 295                 300

Gln Leu Phe Pro Ser Trp Arg Arg Ser Ser Leu Ser Glu Ser Glu Asn
305                 310                 315                 320

Ala Thr Ser Leu Thr Thr Phe
                325

<210> SEQ ID NO 13
<211> LENGTH: 372
<212> TYPE: PRT
<213> ORGANISM: Homo sapiens

<400> SEQUENCE: 13

Met Asn Tyr Pro Leu Thr Leu Glu Met Asp Leu Glu Asn Leu Glu Asp
1               5                   10                  15

Leu Phe Trp Glu Leu Asp Arg Leu Asp Asn Tyr Asn Asp Thr Ser Leu
            20                  25                  30

Val Glu Asn His Leu Cys Pro Ala Thr Glu Gly Pro Leu Met Ala Ser
        35                  40                  45

Phe Lys Ala Val Phe Val Pro Val Ala Tyr Ser Leu Ile Phe Leu Leu
    50                  55                  60

Gly Val Ile Gly Asn Val Leu Val Leu Val Ile Leu Glu Arg His Arg
65                  70                  75                  80

Gln Thr Arg Ser Ser Thr Glu Thr Phe Leu Phe His Leu Ala Val Ala
                85                  90                  95

Asp Leu Leu Leu Val Phe Ile Leu Pro Phe Ala Val Ala Glu Gly Ser
            100                 105                 110

Val Gly Trp Val Leu Gly Thr Phe Leu Cys Lys Thr Val Ile Ala Leu
        115                 120                 125

His Lys Val Asn Phe Tyr Cys Ser Ser Leu Leu Leu Ala Cys Ile Ala
    130                 135                 140

Val Asp Arg Tyr Leu Ala Ile Val His Ala Val His Ala Tyr Arg His
145                 150                 155                 160

Arg Arg Leu Leu Ser Ile His Ile Thr Cys Gly Thr Ile Trp Leu Val
                165                 170                 175

Gly Phe Leu Leu Ala Leu Pro Glu Ile Leu Phe Ala Lys Val Ser Gln
            180                 185                 190

Gly His His Asn Asn Ser Leu Pro Arg Cys Thr Phe Ser Gln Glu Asn
        195                 200                 205

Gln Ala Glu Thr His Ala Trp Phe Thr Ser Arg Phe Leu Tyr His Val
```

-continued

```
                210                 215                 220
Ala Gly Phe Leu Leu Pro Met Leu Val Met Gly Trp Cys Tyr Val Gly
225                 230                 235                 240

Val Val His Arg Leu Arg Gln Ala Gln Arg Pro Gln Arg Gln Lys
            245                 250                 255

Ala Val Arg Val Ala Ile Leu Val Thr Ser Ile Phe Phe Leu Cys Trp
                260                 265                 270

Ser Pro Tyr His Ile Val Ile Phe Leu Asp Thr Leu Ala Arg Leu Lys
            275                 280                 285

Ala Val Asp Asn Thr Cys Lys Leu Asn Gly Ser Leu Pro Val Ala Ile
            290                 295                 300

Thr Met Cys Glu Phe Leu Gly Leu Ala His Cys Cys Leu Asn Pro Met
305                 310                 315                 320

Leu Tyr Thr Phe Ala Gly Val Lys Phe Arg Ser Asp Leu Ser Arg Leu
                325                 330                 335

Leu Thr Lys Leu Gly Cys Thr Gly Pro Ala Ser Leu Cys Gln Leu Phe
            340                 345                 350

Pro Ser Trp Arg Arg Ser Ser Leu Ser Glu Ser Glu Asn Ala Thr Ser
            355                 360                 365

Leu Thr Thr Phe
370

<210> SEQ ID NO 14
<211> LENGTH: 109
<212> TYPE: PRT
<213> ORGANISM: Homo sapiens

<400> SEQUENCE: 14

Met Lys Phe Ile Ser Thr Ser Leu Leu Leu Met Leu Leu Val Ser Ser
1               5                   10                  15

Leu Ser Pro Val Gln Gly Val Leu Glu Val Tyr Tyr Thr Ser Leu Arg
            20                  25                  30

Cys Arg Cys Val Gln Glu Ser Ser Val Phe Ile Pro Arg Arg Phe Ile
        35                  40                  45

Asp Arg Ile Gln Ile Leu Pro Arg Gly Asn Gly Cys Pro Arg Lys Glu
    50                  55                  60

Ile Ile Val Trp Lys Lys Asn Lys Ser Ile Val Cys Val Asp Pro Gln
65                  70                  75                  80

Ala Glu Trp Ile Gln Arg Met Met Glu Val Leu Arg Lys Arg Ser Ser
                85                  90                  95

Ser Thr Leu Pro Val Pro Val Phe Lys Arg Lys Ile Pro
            100                 105

<210> SEQ ID NO 15
<211> LENGTH: 342
<212> TYPE: PRT
<213> ORGANISM: Homo sapiens

<400> SEQUENCE: 15

Met Ala Glu His Asp Tyr His Glu Asp Tyr Gly Phe Ser Ser Phe Asn
1               5                   10                  15

Asp Ser Ser Gln Glu Glu His Gln Asp Phe Leu Gln Phe Ser Lys Val
            20                  25                  30

Phe Leu Pro Cys Met Tyr Leu Val Val Phe Val Cys Gly Leu Val Gly
        35                  40                  45

Asn Ser Leu Val Leu Val Ile Ser Ile Phe Tyr His Lys Leu Gln Ser
    50                  55                  60
```

Leu Thr Asp Val Phe Leu Val Asn Leu Pro Leu Ala Asp Leu Val Phe
65                  70                  75                  80

Val Cys Thr Leu Pro Phe Trp Ala Tyr Ala Gly Ile His Glu Trp Val
                85                  90                  95

Phe Gly Gln Val Met Cys Lys Ser Leu Leu Gly Ile Tyr Thr Ile Asn
            100                 105                 110

Phe Tyr Thr Ser Met Leu Ile Leu Thr Cys Ile Thr Val Asp Arg Phe
            115                 120                 125

Ile Val Val Lys Ala Thr Lys Ala Tyr Asn Gln Gln Ala Lys Arg
130                 135                 140

Met Thr Trp Gly Lys Val Thr Ser Leu Leu Ile Trp Val Ile Ser Leu
145                 150                 155                 160

Leu Val Ser Leu Pro Gln Ile Ile Tyr Gly Asn Val Phe Asn Leu Asp
                165                 170                 175

Lys Leu Ile Cys Gly Tyr His Asp Glu Ala Ile Ser Thr Val Val Leu
            180                 185                 190

Ala Thr Gln Met Thr Leu Gly Phe Phe Leu Pro Leu Leu Thr Met Ile
            195                 200                 205

Val Cys Tyr Ser Val Ile Ile Lys Thr Leu Leu His Ala Gly Gly Phe
            210                 215                 220

Gln Lys His Arg Ser Leu Lys Ile Ile Phe Leu Val Met Ala Val Phe
225                 230                 235                 240

Leu Leu Thr Gln Met Pro Phe Asn Leu Met Lys Phe Ile Arg Ser Thr
                245                 250                 255

His Trp Glu Tyr Tyr Ala Met Thr Ser Phe His Tyr Thr Ile Met Val
            260                 265                 270

Thr Glu Ala Ile Ala Tyr Leu Arg Ala Cys Leu Asn Pro Val Leu Tyr
            275                 280                 285

Ala Phe Val Ser Leu Lys Phe Arg Lys Asn Phe Trp Lys Leu Val Lys
            290                 295                 300

Asp Ile Gly Cys Leu Pro Tyr Leu Gly Val Ser His Gln Trp Lys Ser
305                 310                 315                 320

Ser Glu Asp Asn Ser Lys Thr Phe Ser Ala Ser His Asn Val Glu Ala
                325                 330                 335

Thr Ser Met Phe Gln Leu
            340

<210> SEQ ID NO 16
<211> LENGTH: 120
<212> TYPE: PRT
<213> ORGANISM: Homo sapiens

<400> SEQUENCE: 16

Met Lys Val Ser Glu Ala Ala Leu Ser Leu Leu Val Leu Ile Leu Ile
1               5                   10                  15

Ile Thr Ser Ala Ser Arg Ser Gln Pro Lys Val Pro Glu Trp Val Asn
            20                  25                  30

Thr Pro Ser Thr Cys Cys Leu Lys Tyr Tyr Glu Lys Val Leu Pro Arg
            35                  40                  45

Arg Leu Val Val Gly Tyr Arg Lys Ala Leu Asn Cys His Leu Pro Ala
        50                  55                  60

Ile Ile Phe Val Thr Lys Arg Asn Arg Glu Val Cys Thr Asn Pro Asn
65                  70                  75                  80

Asp Asp Trp Val Gln Glu Tyr Ile Lys Asp Pro Asn Leu Pro Leu Leu
                85                  90                  95

```
Pro Thr Arg Asn Leu Ser Thr Val Lys Ile Ile Thr Ala Lys Asn Gly
            100                 105                 110

Gln Pro Gln Leu Leu Asn Ser Gln
            115                 120

<210> SEQ ID NO 17
<211> LENGTH: 120
<212> TYPE: PRT
<213> ORGANISM: Homo sapiens

<400> SEQUENCE: 17

Met Lys Val Ser Glu Ala Ala Leu Ser Leu Leu Val Leu Ile Leu Ile
  1               5                  10                  15

Ile Thr Ser Ala Ser Arg Ser Gln Pro Lys Val Pro Glu Trp Val Asn
             20                  25                  30

Thr Pro Ser Thr Cys Cys Leu Lys Tyr Tyr Glu Lys Val Leu Pro Arg
         35                  40                  45

Arg Leu Val Val Gly Tyr Arg Lys Ala Leu Asn Cys His Leu Pro Ala
     50                  55                  60

Ile Ile Phe Val Thr Lys Arg Asn Arg Glu Val Cys Thr Asn Pro Asn
 65                  70                  75                  80

Asp Asp Trp Val Gln Glu Tyr Ile Lys Asp Pro Asn Leu Pro Leu Leu
                 85                  90                  95

Pro Thr Arg Asn Leu Ser Thr Val Lys Ile Ile Thr Ala Lys Asn Gly
            100                 105                 110

Gln Pro Gln Leu Leu Asn Ser Gln
            115                 120

<210> SEQ ID NO 18
<211> LENGTH: 150
<212> TYPE: PRT
<213> ORGANISM: Homo sapiens

<400> SEQUENCE: 18

Met Asn Leu Trp Leu Leu Ala Cys Leu Val Ala Gly Phe Leu Gly Ala
  1               5                  10                  15

Trp Ala Pro Ala Val His Thr Gln Gly Val Phe Glu Asp Cys Cys Leu
             20                  25                  30

Ala Tyr His Tyr Pro Ile Gly Trp Ala Val Leu Arg Arg Ala Trp Thr
         35                  40                  45

Tyr Arg Ile Gln Glu Val Ser Gly Ser Cys Asn Leu Pro Ala Ala Ile
     50                  55                  60

Phe Tyr Leu Pro Lys Arg His Arg Lys Val Cys Gly Asn Pro Lys Ser
 65                  70                  75                  80

Arg Glu Val Gln Arg Ala Met Lys Leu Leu Asp Ala Arg Asn Lys Val
                 85                  90                  95

Phe Ala Lys Leu His His Asn Thr Gln Thr Phe Gln Ala Gly Pro His
            100                 105                 110

Ala Val Lys Lys Leu Ser Ser Gly Asn Ser Lys Leu Ser Ser Ser Lys
            115                 120                 125

Phe Ser Asn Pro Ile Ser Ser Ser Lys Arg Asn Val Ser Leu Leu Ile
            130                 135                 140

Ser Ala Asn Ser Gly Leu
145                 150

<210> SEQ ID NO 19
<211> LENGTH: 150
```

```
<212> TYPE: PRT
<213> ORGANISM: Homo sapiens

<400> SEQUENCE: 19

Met Asn Leu Trp Leu Leu Ala Cys Leu Val Ala Gly Phe Leu Gly Ala
1               5                   10                  15

Trp Ala Pro Ala Val His Thr Gln Gly Val Phe Glu Asp Cys Cys Leu
            20                  25                  30

Ala Tyr His Tyr Pro Ile Gly Trp Ala Val Leu Arg Arg Ala Trp Thr
        35                  40                  45

Tyr Arg Ile Gln Glu Val Ser Gly Ser Cys Asn Leu Pro Ala Ala Ile
50                  55                  60

Phe Tyr Leu Pro Lys Arg His Arg Lys Val Cys Gly Asn Pro Lys Ser
65                  70                  75                  80

Arg Glu Val Gln Arg Ala Met Lys Leu Leu Asp Ala Arg Asn Lys Val
                85                  90                  95

Phe Ala Lys Leu His His Asn Thr Gln Thr Phe Gln Ala Gly Pro His
            100                 105                 110

Ala Val Lys Lys Leu Ser Ser Gly Asn Ser Lys Leu Ser Ser Ser Lys
        115                 120                 125

Phe Ser Asn Pro Ile Ser Ser Ser Lys Arg Asn Val Ser Leu Leu Ile
130                 135                 140

Ser Ala Asn Ser Gly Leu
145                 150

<210> SEQ ID NO 20
<211> LENGTH: 84
<212> TYPE: PRT
<213> ORGANISM: Homo sapiens

<400> SEQUENCE: 20

Met Asn Leu Trp Leu Leu Ala Cys Leu Val Ala Gly Phe Leu Gly Ala
1               5                   10                  15

Trp Ala Pro Ala Val His Thr Gln Gly Val Phe Glu Asp Cys Cys Leu
            20                  25                  30

Ala Tyr His Tyr Pro Ile Gly Trp Ala Val Leu Arg Arg Ala Trp Thr
        35                  40                  45

Tyr Arg Ile Gln Glu Val Ser Gly Ser Cys Asn Leu Pro Ala Ala Ile
50                  55                  60

Arg Pro Ser Cys Cys Lys Glu Val Glu Phe Trp Lys Leu Gln Val Ile
65                  70                  75                  80

Ile Val Gln Val

<210> SEQ ID NO 21
<211> LENGTH: 355
<212> TYPE: PRT
<213> ORGANISM: Homo sapiens

<400> SEQUENCE: 21

Met Asp Gln Phe Pro Glu Ser Val Thr Glu Asn Phe Glu Tyr Asp Asp
1               5                   10                  15

Leu Ala Glu Ala Cys Tyr Ile Gly Asp Ile Val Val Phe Gly Thr Val
            20                  25                  30

Phe Leu Ser Ile Phe Tyr Ser Val Ile Phe Ala Ile Gly Leu Val Gly
        35                  40                  45

Asn Leu Leu Val Val Phe Ala Leu Thr Asn Ser Lys Lys Pro Lys Ser
50                  55                  60
```

Val Thr Asp Ile Tyr Leu Leu Asn Leu Ala Leu Ser Asp Leu Leu Phe
65                  70                  75                  80

Val Ala Thr Leu Pro Phe Trp Thr His Tyr Leu Ile Asn Glu Lys Gly
            85                  90                  95

Leu His Asn Ala Met Cys Lys Phe Thr Thr Ala Phe Phe Phe Ile Gly
            100                 105                 110

Phe Phe Gly Ser Ile Phe Phe Ile Thr Val Ile Ser Ile Asp Arg Tyr
        115                 120                 125

Leu Ala Ile Val Leu Ala Ala Asn Ser Met Asn Asn Arg Thr Val Gln
130                 135                 140

His Gly Val Thr Ile Ser Leu Gly Val Trp Ala Ala Ile Leu Val
145                 150                 155                 160

Ala Ala Pro Gln Phe Met Phe Thr Lys Gln Lys Glu Asn Glu Cys Leu
                165                 170                 175

Gly Asp Tyr Pro Glu Val Leu Gln Glu Ile Trp Pro Val Leu Arg Asn
            180                 185                 190

Val Glu Thr Asn Phe Leu Gly Phe Leu Leu Pro Leu Leu Ile Met Ser
            195                 200                 205

Tyr Cys Tyr Phe Arg Ile Ile Gln Thr Leu Phe Ser Cys Lys Asn His
210                 215                 220

Lys Lys Ala Lys Ala Ile Lys Leu Ile Leu Leu Val Val Ile Val Phe
225                 230                 235                 240

Phe Leu Phe Trp Thr Pro Tyr Asn Val Met Ile Phe Leu Glu Thr Leu
                245                 250                 255

Lys Leu Tyr Asp Phe Phe Pro Ser Cys Asp Met Arg Lys Asp Leu Arg
            260                 265                 270

Leu Ala Leu Ser Val Thr Glu Thr Val Ala Phe Ser His Cys Cys Leu
            275                 280                 285

Asn Pro Leu Ile Tyr Ala Phe Ala Gly Glu Lys Phe Arg Arg Tyr Leu
            290                 295                 300

Tyr His Leu Tyr Gly Lys Cys Leu Ala Val Leu Cys Gly Arg Ser Val
305                 310                 315                 320

His Val Asp Phe Ser Ser Glu Ser Gln Arg Ser Arg His Gly Ser
                325                 330                 335

Val Leu Ser Ser Asn Phe Thr Tyr His Thr Ser Asp Gly Asp Ala Leu
            340                 345                 350

Leu Leu Leu
        355

<210> SEQ ID NO 22
<211> LENGTH: 397
<212> TYPE: PRT
<213> ORGANISM: Homo sapiens

<400> SEQUENCE: 22

Met Ala Pro Ile Ser Leu Ser Trp Leu Leu Arg Leu Ala Thr Phe Cys
1               5                   10                  15

His Leu Thr Val Leu Leu Ala Gly Gln His His Gly Val Thr Lys Cys
            20                  25                  30

Asn Ile Thr Cys Ser Lys Met Thr Ser Lys Ile Pro Val Ala Leu Leu
        35                  40                  45

Ile His Tyr Gln Gln Asn Gln Ala Ser Cys Gly Lys Arg Ala Ile Ile
    50                  55                  60

Leu Glu Thr Arg Gln His Arg Leu Phe Cys Ala Asp Pro Lys Glu Gln
65                  70                  75                  80

```
Trp Val Lys Asp Ala Met Gln His Leu Asp Arg Gln Ala Ala Ala Leu
            85                  90                  95
Thr Arg Asn Gly Gly Thr Phe Glu Lys Gln Ile Gly Glu Val Lys Pro
        100                 105                 110
Arg Thr Thr Pro Ala Ala Gly Gly Met Asp Glu Ser Val Val Leu Glu
        115                 120                 125
Pro Glu Ala Thr Gly Glu Ser Ser Ser Leu Glu Pro Thr Pro Ser Ser
    130                 135                 140
Gln Glu Ala Gln Arg Ala Leu Gly Thr Ser Pro Glu Leu Pro Thr Gly
145                 150                 155                 160
Val Thr Gly Ser Ser Gly Thr Arg Leu Pro Pro Thr Pro Lys Ala Gln
                165                 170                 175
Asp Gly Gly Pro Val Gly Thr Glu Leu Phe Arg Val Pro Pro Val Ser
            180                 185                 190
Thr Ala Ala Thr Trp Gln Ser Ser Ala Pro His Gln Pro Gly Pro Ser
        195                 200                 205
Leu Trp Ala Glu Ala Lys Thr Ser Glu Ala Pro Ser Thr Gln Asp Pro
    210                 215                 220
Ser Thr Gln Ala Ser Thr Ala Ser Ser Pro Ala Pro Glu Glu Asn Ala
225                 230                 235                 240
Pro Ser Glu Gly Gln Arg Val Trp Gly Gln Gly Gln Ser Pro Arg Pro
                245                 250                 255
Glu Asn Ser Leu Glu Arg Glu Glu Met Gly Pro Val Pro Ala His Thr
            260                 265                 270
Asp Ala Phe Gln Asp Trp Gly Pro Gly Ser Met Ala His Val Ser Val
        275                 280                 285
Val Pro Val Ser Ser Glu Gly Thr Pro Ser Arg Glu Pro Val Ala Ser
    290                 295                 300
Gly Ser Trp Thr Pro Lys Ala Glu Glu Pro Ile His Ala Thr Met Asp
305                 310                 315                 320
Pro Gln Arg Leu Gly Val Leu Ile Thr Pro Val Pro Asp Ala Gln Ala
                325                 330                 335
Ala Thr Arg Arg Gln Ala Val Gly Leu Leu Ala Phe Leu Gly Leu Leu
            340                 345                 350
Phe Cys Leu Gly Val Ala Met Phe Thr Tyr Gln Ser Leu Gln Gly Cys
        355                 360                 365
Pro Arg Lys Met Ala Gly Glu Met Ala Glu Gly Leu Arg Tyr Ile Pro
    370                 375                 380
Arg Ser Cys Gly Ser Asn Ser Tyr Val Leu Val Pro Val
385                 390                 395

<210> SEQ ID NO 23
<211> LENGTH: 2502
<212> TYPE: DNA
<213> ORGANISM: Homo sapiens

<400> SEQUENCE: 23
tattcatcaa gtgccctcta gctgttaagt cactctgatc tctgactgca gctcctactg      60
ttggacacac ctggccggtg cttcagttag atcaaaccat tgctgaaact gaagaggaca     120
tgtcaaatat tacagatcca cagatgtggg attttgatga tctaaatttc actggcatgc     180
cacctgcaga tgaagattac agcccctgta tgctagaaac tgagacactc aacaagtatg     240
ttgtgatcat cgcctatgcc ctagtgttcc tgctgagcct gctgggaaac tccctggtga     300
tgctggtcat cttatacagc agggtcggcc gctccgtcac tgatgtctac ctgctgaacc     360
```

```
tggccttggc cgacctactc tttgccctga ccttgcccat ctgggccgcc tccaaggtga      420
atggctggat ttttggcaca ttcctgtgca aggtggtctc actcctgaag gaagtcaact      480
tctacagtgg catcctgctg ttggcctgca tcagtgtgga ccgttacctg gccattgtcc      540
atgccacacg cacactgacc cagaagcgtc acttggtcaa gtttgtttgt cttggctgct      600
ggggactgtc tatgaatctg tccctgccct tcttcctttt ccgccaggct taccatccaa      660
acaattccag tccagtttgc tatgaggtcc tgggaaatga cacagcaaaa tggcggatgg      720
tgttgcggat cctgcctcac acctttggct tcatcgtgcc gctgtttgtc atgctgttct      780
gctatggatt caccctgcgt acactgttta aggcccacat ggggcagaag caccgagcca      840
tgagggtcat ctttgctgtc gtcctcatct tcctgctttg ctggctgccc tacaacctgg      900
tcctgctggc agacaccctc atgaggaccc aggtgatcca ggagagctgt gagcgccgca      960
acaacatcgg ccgggccctg gatgccactg agattctggg atttctccat agctgcctca     1020
accccatcat ctacgccttc atcggccaaa attttcgcca tggattcctc aagatcctgg     1080
ctatgcatgg cctggtcagc aaggagttct tggcacgtca tcgtgttacc tcctacactt     1140
cttcgtctgt caatgtctct tccaacctct gaaaaccatc gatgaaggaa tatctcttct     1200
cagaaggaaa gaataaccaa caccctgagg ttgtgtgtgg aaggtgatct ggctctggac     1260
aggcactatc tgggttttgg ggggacgcta taggatgtgg ggaagttagg aactggtgtc     1320
ttcaggggcc acaccaacct tctgaggagc tgttgaggta cctccaagga ccggcctttg     1380
cacctccatg gaaacgaagc accatcattc ccgttgaacg tcacatcttt aacccactaa     1440
ctggctaatt agcatggcca catctgagcc ccgaatctga cattagatga gagaacaggg     1500
ctgaagctgt gtcctcatga gggctggatg ctctcgttga ccctcacagg agcatctcct     1560
caactctgag tgttaagcgt tgagccacca agctggtggc tctgtgtgct ctgatccgag     1620 ctcaggggg tggttttccc atctcaggtg tgttgcagtg tctgctggag acattgaggc     1680
aggcactgcc aaaacatcaa cctgccagct ggccttgtga ggagctggaa acacatgttc     1740
cccttggggg tggtggatga acaaagagaa agagggtttg gaagccagat ctatgccaca     1800
agaaccccct ttaccccat gaccaacatc gcagacacat gtgctggcca cctgctgagc     1860
cccaagtgga acgagacaag cagcccttag cccttcccct ctgcagcttc caggctggcg     1920
tgcagcatca gcatccctag aaagccatgt gcagccacca gtccattggg caggcagatg     1980
ttcctaataa agcttctgtt ccgtgcttgt ccctgtggaa gtatcttggt tgtgacagag     2040
tcaagggtgt gtgcagcatt gttggctgtt cctgcagtag aatgggggca gcacctccta     2100
agaaggcacc tctctgggtt gaagggcagt gttccctggg gctttaactc ctgctagaac     2160
agtctcttga ggcacagaaa ctcctgttca tgcccatacc cctggccaag gaagatccct     2220
ttgtccacaa gtaaaaggaa atgctcctcc agggagtctc agcttcaccc tgaggtgagc     2280
atcatcttct gggttaggcc ttgcctaggc atagccctgc ctcaagctat gtgagctcac     2340
cagtccctcc ccaaatgctt tccatgagtt gcagtttttt cctagtctgt tttccctcct     2400
tggagacagg gccctgtcgg tttattcact gtatgtcctt ggtgcctgga gcctactaaa     2460
tgctcaataa ataatgatca caggaaaaaa aaaaaaaaaa aa                        2502
```

<210> SEQ ID NO 24
<211> LENGTH: 2880
<212> TYPE: DNA
<213> ORGANISM: Homo sapiens

<400> SEQUENCE: 24

```
aggttcaaaa cattcagaga cagaaggtgg atagacaaat ctccaccttc agactggtag    60
gctcctccag aagccatcag acaggaagat gtgaaaatcc ccagcactca tcccagaatc   120
actaagtggc acctgtcctg ggccaaagtc ccaggacaga cctcattgtt cctctgtggg   180
aatacctccc caggagggca tcctggattt ccccttgca acccaggtca gaagtttcat    240
cgtcaaggtt gtttcatctt ttttttcctg tctaacagct ctgactacca cccaaccttg   300
aggcacagtg aagacatcgg tggccactcc aataacagca ggtcacagct gctcttctgg   360
aggtgtccta caggtgaaaa gcccagcgac ccagtcagga tttaagttta cctcaaaaat   420
ggaagatttt aacatggaga gtgacagctt tgaagatttc tggaaaggtg aagatcttag   480
taattacagt tacagctcta ccctgccccc ttttctacta gatgccgccc catgtgaacc   540
agaatccctg gaaatcaaca agtatttgt ggtcattatc tatgccctgg tattcctgct    600
gagcctgctg ggaaactccc tcgtgatgct ggtcatctta tacagcaggg tcggccgctc   660
cgtcactgat gtctacctgc tgaacctagc cttggccgac ctactctttg ccctgacctt   720
gcccatctgg gccgcctcca aggtgaatgg ctggattttt ggcacattcc tgtgcaaggt   780
ggtctcactc ctgaaggaag tcaacttcta tagtggcatc ctgctactgg cctgcatcag   840
tgtggaccgt tacctggcca ttgtccatgc cacacgcaca ctgacccaga agcgctactt   900
ggtcaaattc atatgtctca gcatctgggg tctgtccttg ctcctggccc tgcctgtctt   960
acttttccga aggaccgtct actcatccaa tgttagccca gcctgctatg aggacatggg  1020
caacaataca gcaaactggc ggatgctgtt acggatcctg ccccagtcct ttggcttcat  1080
cgtgccactg ctgatcatgc tgttctgcta cggattcacc ctgcgtacgc tgtttaaggc  1140
ccacatgggg cagaagcacc gggccatgcg ggtcatcttt gctgtcgtcc tcatcttcct  1200
gctctgctgg ctgccctaca acctggtcct gctggcagac accctcatga ggacccaggt  1260
gatccaggag acctgtgagc gccgcaatca catcgaccgg gctctggatg ccaccgagat  1320
tctgggcatc cttcacagct gcctcaaccc cctcatctac gccttcattg gccagaagtt  1380
tcgccatgga ctcctcaaga ttctagctat acatggcttg atcagcaagg actccctgcc  1440
caaagacagc aggccttcct tgttggctc ttcttcaggg cacacttcca ctactctcta   1500
agacctcctg cctaagtgca gccccgtggg gttcctccct tctcttcaca gtcacattcc  1560
aagcctcatg tccactggtt cttcttggtc tcagtgtcaa tgcagccccc attgtggtca  1620
caggaagtag aggaggccac gttcttacta gtttcccttg catggtttag aaagcttgcc  1680
ctggtgcctc accccttgcc ataattacta tgtcatttgc tggagctctg cccatcctgc  1740
ccctgagccc atggcactct atgttctaag aagtgaaaat ctacactcca gtgagacagc  1800
tctgcatact cattaggatg gctagtatca aagaaagaa atcaggctg gccaacgggg   1860 tgaaaccctg tctctactaa aaatacaaaa aaaaaaaaa attagccggg cgtggtggtg    1920
agtgcctgta atcacagcta cttgggaggc tgagatggga gaatcacttg aacccgggag  1980
gcagaggttg cagtgagccg agattgtgcc cctgcactcc agcctgagcg acagtgagac  2040
tctgtctcag tccatgaaga gtagaggag aaactggaac tctcgagcgt tgctggggggg 2100 gattgtaaaa tggtgtgacc actgcagaag acagtatggc agctttcctc aaaacttcag  2160
acatagaatt aacacatgat cctgcaattc cactttatagg aattgaccca caagaaatga  2220
aagcagggac ttgaacccat atttgtacac caatattcat agcagcttat tcacaagacc  2280
caaaaggcag aagcaaccca aatgttcatc aatgaatgaa tgaatggcta agcaaaatgt  2340
gatatgtacc taacgaagta tccttcagcc tgaaagagga atgaagtact catacatgtt  2400
```

| | | | | |
|---|---|---|---|---|
| acaacacgga | cgaaccttga | aaactttatg | ctaagtgaaa | taagccagac atcaacagat | 2460 |
| aaatagttta | tgattccacc | tacatgaggt | actgagagtg | aacaaattta cagagacaga | 2520 |
| aagcagaaca | gtgattacca | gggactgagg | ggaggggagc | atgggaagtg acggtttaat | 2580 |
| gggcacaggg | tttatgttta | ggatgttgaa | aaagttctgc | agataaacag tagtgatagt | 2640 |
| tgtaccgcaa | tgtgacttaa | tgccactaaa | ttgacactta | aaaatggttt aaatggtcaa | 2700 |
| ttttgttatg | tatattttat | atcaatttaa | aaaaaaacct | gagccccaaa aggtatttta | 2760 |
| atcaccaagg | ctgattaaac | caaggctaga | accacctgcc | tatatttttt gttaaatgat | 2820 |
| ttcattcaat | atctttttt | taataaacca | tttttacttg | ggtgtttata aaaaaaaaaa | 2880 |

<210> SEQ ID NO 25
<211> LENGTH: 1119
<212> TYPE: DNA
<213> ORGANISM: Homo sapiens

<400> SEQUENCE: 25

| | | | | |
|---|---|---|---|---|
| cacagagccc | gggccgcagg | cacctcctcg | ccagctcttc | cgctcctctc acagccgcca | 60 |
| gacccgcctg | ctgagcccca | tggccgcgc | tgctctctcc | gccgccccca gcaatccccg | 120 |
| gctcctgcga | gtggcactgc | tgctcctgct | cctggtagcc | gctggccggc gcgcagcagg | 180 |
| agcgtccgtg | gccactgaac | tgcgctgcca | gtgcttgcag | accctgcagg gaattcaccc | 240 |
| caagaacatc | caaagtgtga | acgtgaagtc | ccccggaccc | cactgcgccc aaaccgaagt | 300 |
| catagccaca | ctcaagaatg | gcggaaagc | ttgcctcaat | cctgcatccc ccatagttaa | 360 |
| gaaaatcatc | gaaaagatgc | tgaacagtga | caaatccaac | tgaccagaag ggaggaggaa | 420 |
| gctcactggt | ggctgttcct | gaaggaggcc | ctgcccttat | aggaacagaa gaggaaagag | 480 |
| agacacagct | gcagaggcca | cctggattgt | gcctaatgtg | tttgagcatc gcttaggaga | 540 |
| agtcttctat | ttatttattt | attcattagt | tttgaagatt | ctatgttaat atttaggtg | 600 |
| taaaataatt | aagggtatga | ttaactctac | ctgcacactg | tcctattata ttcattcttt | 660 |
| ttgaaatgtc | aaccccaagt | tagttcaatc | tggattcata | tttaatttga aggtagaatg | 720 |
| ttttcaaatg | ttctccagtc | attatgttaa | tatttctgag | gagcctgcaa catgccagcc | 780 |
| actgtgatag | aggctggcgg | atccaagcaa | atggccaatg | agatcattgt gaaggcaggg | 840 |
| gaatgtatgt | gcacatctgt | tttgtaactg | tttagatgaa | tgtcagttgt tatttattga | 900 |
| aatgatttca | cagtgtgtgg | tcaacatttc | tcatgttgaa | actttaagaa ctaaaatgtt | 960 |
| ctaaatatcc | cttggacatt | ttatgtcttt | cttgtaaggc | atactgcctt gtttaatggt | 1020 |
| agttttacag | tgtttctggc | ttagaacaaa | ggggcttaat | tattgatgtt tcatagaga | 1080 |
| atataaaaat | aaagcactta | tagaaaaaaa | aaaaaaaa | | 1119 |

<210> SEQ ID NO 26
<211> LENGTH: 1234
<212> TYPE: DNA
<213> ORGANISM: Homo sapiens

<400> SEQUENCE: 26

| | | | | |
|---|---|---|---|---|
| gagctccggg | aatttccctg | gcccgggact | ccgggctttc | cagccccaac catgcataaa | 60 |
| aggggttcgc | cgttctcgga | gagccacaga | gcccgggcca | caggcagctc cttgccagct | 120 |
| ctcctcctcg | cacagccgct | cgaaccgcct | gctgagcccc | atggcccgcg ccacgctctc | 180 |
| cgccgccccc | agcaatcccc | ggctcctgcg | ggtggcgctg | ctgctcctgc tcctggtggc | 240 |
| cgccagccgg | cgcgcagcag | gagcgcccct | ggccactgaa | ctgcgctgcc agtgcttgca | 300 |

```
gaccctgcag ggaattcacc tcaagaacat ccaaagtgtg aaggtgaagt cccccggacc    360
ccactgcgcc caaaccgaag tcatagccac actcaagaat gggcagaaag cttgtctcaa    420
ccccgcatcg cccatggtta agaaaatcat cgaaaagatg ctgaaaaatg caaatccaa     480
ctgaccagaa ggaaggagga agcttattgg tggctgttcc tgaaggaggc cctgccctta    540
caggaacaga agaggaaaga gagacacagc tgcagaggcc acctggattg cgcctaatgt    600
gtttgagcat cacttaggag aagtcttcta tttatttatt tatttattta tttgtttgtt    660
ttagaagatt ctatgttaat attttatgtg taaaataagg ttatgattga atctacttgc    720
acactctccc attatattta ttgtttattt taggtcaaac ccaagttagt tcaatcctga    780
ttcatattta atttgaagat agaaggtttg cagatattct ctagtcattt gttaatattt    840
cttcgtgatg acatatcaca tgtcagccac tgtgatagag gctgaggaat ccaagaaaat    900
ggccagtgag atcaatgtga cggcagggaa atgtatgtgt gtctattttg taactgtaaa    960
gatgaatgtc agttgttatt tattgaaatg atttcacagt gtgtggtcaa catttctcat   1020
gttgaagctt taagaactaa aatgttctaa atatcccttg acattttat gtctttcttg    1080
taaggcatac tgccttgttt aatgttaatt atgcagtgtt tccctctgtg ttagagcaga   1140
gaggtttcga tatttattga tgttttcaca aagaacagga aaataaaata tttaaaaata   1200
taaaaaaaaa aaaaaaaaaa aaaaaaaaaa aaaa                                1234
```

<210> SEQ ID NO 27
<211> LENGTH: 1166
<212> TYPE: DNA
<213> ORGANISM: Homo sapiens

<400> SEQUENCE: 27

```
gctccgggaa tttccctggc ccggccgctc cgggctttcc agtctcaacc atgcataaaa     60
agggttcgcc gatcttgggg agccacacag cccgggtcgc aggcacctcc ccgccagctc    120
tcccgcttct cgcacagctt cccgacgcgt ctgctgagcc ccatggccca cgccacgctc    180
tccgccgccc ccagcaatcc ccggctcctg cgggtggcgc tgctgctcct gctcctggtg    240
gccgccagcc ggcgcgcagc aggagcgtcc gtggtcactg aactgcgctg ccagtgcttg    300
cagacactgc agggaattca cctcaagaac atccaaagtg tgaatgtaag gtcccccgga    360
ccccactgcg cccaaaccga gtcatagcc acactcaaga atgggaagaa agcttgtctc    420
aaccccgcat ccccccatggt tcagaaaatc atcgaaaaga tactgaacaa ggggagcacc    480
aactgacaga agaagtaa gaagcttatc agcgtatcat tgacacttcc tgcagggtgg    540
tccctgccct taccagagct gaaaatgaaa agagaacag cagctttcta gggacagctg    600
gaaaggactt aatgtgtttg actatttctt acgagggttc tacttattta tgtatttatt    660
tttgaaagct tgtatttta tattttacat gctgttattt aaagatgtga gtgtgtttca    720
tcaaacatag ctcagtcctg attatttaat tggaatatga tgggtttaa atgtgtcatt    780
aaactaatat ttagtgggag accataatgt gtcagccacc ttgataaatg acagggtggg    840
gaactggagg gtgggggat tgaaatgcaa gcaattagtg gatcactgtt agggtaaggg    900
aatgtatgta cacatctatt ttttatactt ttttttaaa aaagaatgt cagttgttat    960
ttattcaaat tatctcacat tatgtgttca acatttttat gctgaagttt cccttagaca   1020
ttttatgtct tgcttgtagg gcataatgcc ttgtttaatg tccattctgc agcgtttctc   1080
tttcccttgg aaaagagaat ttatcattac tgttacattt gtacaaatga catgataata   1140
aaagttttat gaaaaaaaaa aaaaaa                                         1166
```

<210> SEQ ID NO 28
<211> LENGTH: 2475
<212> TYPE: DNA
<213> ORGANISM: Homo sapiens

<400> SEQUENCE: 28

| | | | | | |
|---|---|---|---|---|---|
| gtgcagaagg | cacgaggaag | ccacagtgct | ccggatcctc | caatcttcgc | tcctccaatc | 60 |
| tccgctcctc | cacccagttc | aggaacccgc | gaccgctcgc | agcgctctct | tgaccactat | 120 |
| gagcctcctg | tccagccgcg | cggcccgtgt | ccccggtcct | tcgagctcct | tgtgcgcgct | 180 |
| gttggtgctg | ctgctgctgc | tgacgcagcc | agggcccatc | gccagcgctg | gtcctgccgc | 240 |
| tgctgtgttg | agagagctgc | gttgcgtttg | tttacagacc | acgcaaggag | ttcatcccaa | 300 |
| aatgatcagt | aatctgcaag | tgttcgccat | aggcccacag | tgctccaagg | tggaagtggt | 360 |
| agcctccctg | aagaacggga | aggaaatttg | tcttgatcca | gaagcccctt | ttctaaagaa | 420 |
| agtcatccag | aaaattttgg | acggtggaaa | caaggaaaac | tgattaagag | aaatgagcac | 480 |
| gcatggaaaa | gtttcccagt | cttcagcaga | gaagttttct | ggaggtctct | gaacccaggg | 540 |
| aagacaagaa | ggaaagattt | tgttgttgtt | tgtttatttg | tttttccagt | agttagcttt | 600 |
| cttcctggat | tcctcacttt | gaagagtgtg | aggaaaacct | atgtttgccg | cttaagcttt | 660 |
| cagctcagct | aatgaagtgt | ttagcatagt | acctctgcta | tttgctgtta | ttttatctgc | 720 |
| tatgctattg | aagttttggc | aattgactat | agtgtgagcc | aggaatcact | ggctgttaat | 780 |
| cttttcaaagt | gtcttgaatt | gtaggtgact | attatatttc | caagaaatat | tccttaagat | 840 |
| attaactgag | aaggctgtgg | atttaatgtg | gaaatgatgt | ttcataagaa | ttctgttgat | 900 |
| ggaaatacac | tgttatcttc | acttttataa | gaaataggaa | atattttaat | gtttcttggg | 960 |
| gaatatgtta | gagaatttcc | ttactcttga | ttgtgggata | ctatttaatt | atttcacttt | 1020 |
| agaaagctga | gtgttttcaca | ccttatctat | gtagaatata | tttccttatt | cagaatttct | 1080 |
| aaaagtttaa | gttctatgag | ggctaatatc | ttatcttcct | ataatttag | acattcttta | 1140 |
| tcttttttagt | atggcaaact | gccatcattt | actttttaaac | tttgatttta | tatgctatt | 1200 |
| attaagtatt | ttattaggag | taccataatt | ctggtagcta | aatatatatt | ttagatagat | 1260 |
| gaagaagcta | gaaaacaggc | aaattcctga | ctgctagttt | atatagaaat | gtattctttt | 1320 |
| agttttaaa | gtaaaggcaa | acttaacaat | gacttgtact | ctgaaagttt | tggaaacgta | 1380 |
| ttcaaacaat | ttgaatataa | atttatcatt | tagttataaa | aatatatagc | gacatcctcg | 1440 |
| aggccctagc | atttctcctt | ggataggga | ccagagagag | cttggaatgt | taaaaacaaa | 1500 |
| acaaaacaaa | aaaaacaag | gagaagttgt | ccaagggatg | tcaatttttt | atccctctgt | 1560 |
| atgggttaga | ttttccaaaa | tcataatttg | aagaaggcca | gcatttatgg | tagaatatat | 1620 |
| aattatatat | aaggtggcca | cgctggggca | agttccctcc | ccactcacag | ctttggcccc | 1680 |
| tttcacagag | tagaacctgg | gttagaggat | tgcagaagac | gagcggcagc | ggggagggca | 1740 |
| gggaagatgc | ctgtcgggtt | tttagcacag | ttcatttcac | tgggattttg | aagcatttct | 1800 |
| gtctgaatgt | aaagcctgtt | ctagtcctgg | tgggacacac | tggggttggg | ggtgggggaa | 1860 |
| gatgcggtaa | tgaaaccggt | tagtcagtgt | tgtcttaata | tccttgataa | tgctgtaaag | 1920 |
| tttatttta | caaatatttc | tgtttaagct | atttcacctt | tgtttggaaa | tccttcccctt | 1980 |
| ttaaagagaa | aatgtgacac | ttgtgaaaag | gcttgtagga | aagctcctcc | cttttttttct | 2040 |
| ttaaaccttt | aaatgacaaa | cctaggtaat | taatggttgt | gaattctat | ttttgctttg | 2100 |
| ttttttaatga | acatttgtct | ttcagaatag | gattctgtga | taatatttaa | atggcaaaaa | 2160 |

-continued

| | |
|---|---|
| caaaacataa ttttgtgcaa ttaacaaagc tactgcaaga aaaataaaac atttcttggt | 2220 |
| aaaaacgtat gtatttatat attatatatt tatatataat atatattata tatttagcat | 2280 |
| tgctgagctt tttagatgcc tattgtgtat cttttaaagg ttttgaccat tttgttatga | 2340 |
| gtaattacat atatattaca ttcactatat taaaattgta cttttttact atgtgtctca | 2400 |
| ttggttcata gtctttattt tgtcctttga ataaacatta aaagatttct aaacttcaaa | 2460 |
| aaaaaaaaaa aaaaa | 2475 |

<210> SEQ ID NO 29
<211> LENGTH: 1677
<212> TYPE: DNA
<213> ORGANISM: Homo sapiens

<400> SEQUENCE: 29

| | |
|---|---|
| acccettctt tccacactgc ccctgagtt cagggaattt ccccagcatc ccaaagcttg | 60 |
| agtttcctgc cagtcgggag ggatgaatgc agataaaggg agtgcagaag gcacgaggaa | 120 |
| accaaagtgc tctgtatcct ccagtctccg cgcctccacc cagctcagga acccgcgaac | 180 |
| cctctcttga ccactatgag cctcccgtcc agccgcgcgg cccgtgtccc gggtccttcg | 240 |
| ggctccttgt gcgcgctgct cgcgctgctg ctcctgctga cgccgccggg gccctcgcc | 300 |
| agcgctggtc ctgtctctgc tgtgctgaca gagctgcgtt gcacttgttt acgcgttacg | 360 |
| ctgagagtaa accccaaaac gattggtaaa ctgcaggtgt tccccgcagg cccgcagtgc | 420 |
| tccaaggtgg aagtggtagc ctccctgaag aacgggaagc aagtttgtct ggacccggaa | 480 |
| gccccttttc taagaaagt catccagaaa attttggaca gtggaaacaa gaaaaactga | 540 |
| gtaacaaaaa agaccatgca tcataaaatt gcccagtctt cagcggagca gttttctgga | 600 |
| gatccctgga cccagtaaga ataagaagga agggttggtt ttttccatt ttctacatgg | 660 |
| attccctact ttgaagagtg tgggggaaag cctacgcttc tccctgaagt ttacagctca | 720 |
| gctaatgaag tactaatata gtatttccac tatttactgt tattttacct gataagttat | 780 |
| tgaacccttt ggcaattgac catattgtga gcaaagaatc actggttatt agtctttcaa | 840 |
| tgaatattga attgaagata actattgtat ttctatcata cattccttaa agtcttaccg | 900 |
| aaaaggctgt ggatttcgta tggaaataat gttttattag tgtgctgttg agggaggtat | 960 |
| cctgttgttc ttactcactc ttctcataaa ataggaaata ttttagttct gtttcttggg | 1020 |
| gaatatgtta ctctttaccc taggatgcta tttaagttgt actgtattag aacactgggt | 1080 |
| gtgtcatacc gttatctgtg cagaatatat ttccttattc agaatttcta aaaatttaag | 1140 |
| ttctgtaagg gctaatatat tctcttccta tggttttaga cgtttgatgt cttcttagta | 1200 |
| tggcataatg tcatgattta ctcattaaac tttgattttg tatgctattt tttcactata | 1260 |
| ggatgactat aattctggtc actaaatata cactttagat agatgaagaa gcccaaaaac | 1320 |
| agataaattc ctgattgcta atttacatag aaatgtattc tcttggtttt ttaaataaaa | 1380 |
| gcaaaattaa caatgatctg tgctctgaaa gttttgaaaa tatatttgaa caatttgaat | 1440 |
| ataaattcat catttagtcc tcaaaatata tatagcattg ctaagatttt cagatatcta | 1500 |
| ttgtggatct tttaaaggtt ttgaccattt tgttatgagg aattatacat gtatcacatt | 1560 |
| cactatatta aaaattgcact tttatttttt cctgtgtgtc atgttggttt ttggtacttg | 1620 |
| tattgtcatt tggagaaaca ataaaagatt tctaaaccaa aaaaaaaaa aaaaaaa | 1677 |

<210> SEQ ID NO 30
<211> LENGTH: 1307
<212> TYPE: DNA

<213> ORGANISM: Homo sapiens

<400> SEQUENCE: 30

```
acttatctgc agacttgtag gcagcaactc accctcactc agaggtcttc tggttctgga      60
aacaactcta gctcagcctt ctccaccatg agcctcagac ttgataccac cccttcctgt     120
aacagtgcga gaccacttca tgccttgcag gtgctgctgc ttctgtcatt gctgctgact     180
gctctggctt cctccaccaa aggacaaact aagagaaact ggcgaaagg caaagaggaa      240
agtctagaca gtgacttgta tgctgaactc cgctgcatgt gtataaagac aacctctgga     300
attcatccca aaaacatcca aagtttggaa gtgatcggga aaggaaccca ttgcaaccaa     360
gtcgaagtga tagccacact gaaggatggg aggaaaatct gcctggaccc agatgctccc     420
agaatcaaga aaattgtaca gaaaaaattg gcaggtgatg aatctgctga ttaatttgtt     480
ctgtttctgc caaacttctt taactcccag gaagggtaga attttgaaac cttgattttc     540
tagagttctc atttattcag gatacctatt cttactgtat aaaatttgg atatgtgttt      600
cattctgtct caaaaatcac attttattct gagaaggttg gttaaaagat ggcagaaaga     660
agatgaaaat aaataagcct ggtttcaacc ctctaattct tgcctaaaca ttggactgta     720
ctttgcattt ttttctttaa aaatttctat tctaacacaa cttggttgat ttttcctggt     780
ctactttatg gttattagac atactcatgg gtattattag atttcataat ggtcaatgat     840
aataggaatt acatggagcc caacagagaa tatttgctca atacattttt gttaatatat     900
ttaggaactt aatggagtct ctcagtgtct tagtcctagg atgtcttatt taaaatactc     960
cctgaaagtt tattctgatg tttatttag ccatcaaaca ctaaaataat aaattggtga     1020
atatgaatct tataaactgt ggttagctgg tttaaagtga atatatttgc cactagtaga     1080
acaaaaatag atgatgaaaa tgaattaaca tatctacata gttataattc tatcattaga     1140
atgagcctta taaataagta caatatagga cttcaacctt actagactcc taattctaaa     1200
ttctactttt ttcatcaaca gaactttcat tcattttta aaccctaaaa cttatacccca     1260
cactattctt acaaaaatat tcacatgaaa taaaaatttg ctattga                  1307
```

<210> SEQ ID NO 31
<211> LENGTH: 1718
<212> TYPE: DNA
<213> ORGANISM: Homo sapiens

<400> SEQUENCE: 31

```
gagggtgcat aagttctcta gtagggtgat gatataaaaa gccaccggag cactccataa      60
ggcacaaact ttcagagaca gcagagcaca caagcttcta ggacaagagc caggaagaaa     120
ccaccggaag gaaccatctc actgtgtgta aacatgactt ccaagctggc cgtggctctc     180
ttggcagcct tcctgatttc tgcagctctg tgtgaaggtg cagttttgcc aaggagtgct     240
aaagaactta gatgtcagtg cataaagaca tactccaaac ctttccaccc caaatttatc     300
aaagaactga gagtgattga gagtggacca cactgcgcca acacagaaat tattgtaaag     360
ctttctgatg gaagagagct ctgtctggac cccaaggaaa actgggtgca gagggttgtg     420
gagaagtttt tgaagagggc tgagaattca taaaaaaatt cattctctgt ggtatccaag     480
aatcagtgaa gatgccagtg aaacttcaag caaatctact tcaacacttc atgtattgtg     540
tgggtctgtt gtagggttgc cagatgcaat acaagattcc tggttaaatt tgaatttcag     600
taaacaatga atagttttc attgtaccat gaaatatcca gaacatactt atatgtaaag     660
tattatttat ttgaatctac aaaaaacaac aaataatttt taaatataag gattttccta     720
```

-continued

| | | |
|---|---|---|
| gatattgcac gggagaatat acaaatagca aaattgaggc caagggccaa gagaatatcc | 780 |
| gaactttaat ttcaggaatt gaatgggttt gctagaatgt gatatttgaa gcatcacata | 840 |
| aaaatgatgg gacaataaat tttgccataa agtcaaattt agctggaaat cctggatttt | 900 |
| tttctgttaa atctggcaac cctagtctgc tagccaggat ccacaagtcc ttgttccact | 960 |
| gtgccttggt ttctccttta tttctaagtg gaaaaagtat tagccaccat cttacctcac | 1020 |
| agtgatgttg tgaggacatg tggaagcact ttaagttttt tcatcataac ataaattatt | 1080 |
| ttcaagtgta acttattaac ctatttatta tttatgtatt tatttaagca tcaaatattt | 1140 |
| gtgcaagaat ttggaaaaat agaagatgaa tcattgattg aatagttata agatgttat | 1200 |
| agtaaattta ttttatttta gatattaaat gatgttttat tagataaatt tcaatcaggg | 1260 |
| tttttagatt aaacaaacaa acaattgggt acccagttaa attttcattt cagataaaca | 1320 |
| acaaataatt ttttagtata agtacattat tgtttatctg aaattttaat tgaactaaca | 1380 |
| atcctagttt gatactccca gtcttgtcat tgccagctgt gttggtagtg ctgtgttgaa | 1440 |
| ttacggaata atgagttaga actattaaaa cagccaaaac tccacagtca atattagtaa | 1500 |
| tttcttgctg gttgaaactt gtttattatg tacaaataga ttcttataat attatttaaa | 1560 |
| tgactgcatt tttaaataca aggctttata tttttaactt taagatgttt ttatgtgctc | 1620 |
| tccaaatttt ttttactgtt tctgattgta tggaaatata aaagtaaata tgaaacattt | 1680 |
| aaaatataat ttgttgtcaa agtaaaaaaa aaaaaaaa | 1718 |

<210> SEQ ID NO 32
<211> LENGTH: 1691
<212> TYPE: DNA
<213> ORGANISM: Homo sapiens

<400> SEQUENCE: 32

| | | |
|---|---|---|
| aacttcagtt tgttggctgc ggcagcaggt agcaaagtga cgccgagggc ctgagtgctc | 60 |
| cagtagccac cgcatctgga gaaccagcgg ttaccatgga ggggatcagt atatacactt | 120 |
| cagataacta caccgaggaa atgggctcag gggactatga ctccatgaag gaaccctgtt | 180 |
| tccgtgaaga aaatgctaat ttcaataaaa tcttcctgcc caccatctac tccatcatct | 240 |
| tcttaactgg cattgtgggc aatggattgg tcatcctggt catgggttac cagaagaaac | 300 |
| tgagaagcat gacggacaag tacaggctgc acctgtcagt ggccgacctc ctctttgtca | 360 |
| tcacgcttcc cttctgggca gttgatgccg tggcaaactg gtactttggg aacttcctat | 420 |
| gcaaggcagt ccatgtcatc tacacagtca acctctacag cagtgtcctc atcctggcct | 480 |
| tcatcagtct ggaccgctac ctggccatcg tccacgccac caacagtcag aggccaagga | 540 |
| agctgttggc tgaaaaggtg gtctatgttg gcgtctggat ccctgccctc ctgctgacta | 600 |
| ttcccgactt catctttgcc aacgtcagtg aggcagatga cagatatatc tgtgaccgct | 660 |
| tctaccccaa tgacttgtgg gtggttgtgt tccagtttca gcacatcatg gttggcctta | 720 |
| tcctgcctgg tattgtcatc ctgtcctgct attgcattat catctccaag ctgtcacact | 780 |
| ccaagggcca ccagaagcgc aaggccctca gaccacagt catcctcatc ctggctttct | 840 |
| tcgcctgttg gctgccttac tacattggga tcagcatcga ctccttcatc ctcctggaaa | 900 |
| tcatcaagca agggtgtgag tttgagaaca ctgtgcacaa gtggatttcc atcaccgagg | 960 |
| ccctagcttt cttccactgt gtgtctgaac ccatcctcta tgctttcctt ggagccaaat | 1020 |
| ttaaaacctc tgcccagcac gcactcacct ctgtgagcag agggtccagc ctcaagatcc | 1080 |
| tctccaaagg aaagcgaggt ggacattcat ctgtttccac tgagtctgag tcttcaagtt | 1140 |

```
ttcactccag ctaacacaga tgtaaaagac ttttttttat acgataaata actttttttt      1200
aagttacaca ttttcagat ataaaagact gaccaatatt gtacagtttt tattgcttgt       1260 tggattttg tcttgtgttt ctttagtttt tgtgaagttt aattgactta tttatataaa       1320 tttttttgt ttcatattga tgtgtgtcta ggcaggacct gtggccaagt tcttagttgc       1380
tgtatgtctc gtggtaggac tgtagaaaag ggaactgaac attccagagc gtgtagtgaa      1440
tcacgtaaag ctagaaatga tccccagctg tttatgcata gataatctct ccattcccgt      1500
ggaacgtttt tcctgttctt aagacgtgat tttgctgtag aagatggcac ttataaccaa      1560
agcccaaagt ggtatagaaa tgctggtttt tcagttttca ggagtgggtt gatttcagca      1620
cctacagtgt acagtcttgt attaagttgt taataaaagt acatgttaaa cttaaaaaaa      1680
aaaaaaaaaa a                                                           1691

<210> SEQ ID NO 33
<211> LENGTH: 3545
<212> TYPE: DNA
<213> ORGANISM: Homo sapiens

<400> SEQUENCE: 33
gccgcacttt cactctccgt cagccgcatt gcccgctcgg cgtccggccc ccgacccgcg        60
ctcgtccgcc cgcccgcccg cccgcccgcg ccatgaacgc caaggtcgtg gtcgtgctgg       120
tcctcgtgct gaccgcgctc tgcctcagcg acggaagcc cgtcagcctg agctacagat       180
gcccatgccg attcttcgaa agccatgttg ccagagccaa cgtcaagcat ctcaaaattc       240
tcaacactcc aaactgtgcc cttcagattg tagcccggct gaagaacaac aacagacaag       300
tgtgcattga cccgaagcta agtggattca aggagtacct ggagaaagct ttaaacaaga       360
ggttcaagat gtgagagggt cagacgcctg aggaacccct tacagtaggag cccagctctg       420 aaaccagtgt tagggaaggg cctgccacag cctcccctgc cagggcaggg ccccaggcat       480
tgccaagggc tttgttttgc cacactttgcc atattttcac catttgatta tgtagcaaaa       540
tacatgacat ttatttttca tttagtttga ttattcagtg tcactggcga cacgtagcag       600
cttagactaa ggccattatt gtacttgcct tattagagtg tctttccacg gagccactcc       660
tctgactcag ggctcctggg ttttgtattc tctgagctgt gcaggtgggg agactgggct       720
gagggagcct ggccccatgg tcagccctag ggtggagagc caccaagagg gacgcctggg       780
ggtgccagga ccagtcaacc tgggcaaagc ctagtgaagg cttctctctg tgggatggga       840
tggtggaggg ccacatggga ggctcacccc cttctccatc cacatgggag ccgggtctgc       900
ctcttctggg agggcagcag ggctaccctg agctgaggca gcagtgtgag gccagggcag       960
agtgagaccc agccctcatc ccgagcacct ccacatcctc cacgttctgc tcatcattct      1020
ctgtctcatc catcatcatg tgtgtccacg actgtctcca tggccccgca aaaggactct      1080
caggaccaaa gctttcatgt aaactgtgca ccaagcagga aatgaaaatg tcttgtgtta      1140
cctgaaaaca ctgtgcacat ctgtgtcttg tttggaatat tgtccattgt ccaatcctat      1200 gttttttgttc aaagccagcg tcctcctctg tgaccaatgt cttgatgcat gcactgttcc      1260
ccctgtgcag ccgctgagcg aggagatgct ccttgggccc tttgagtgca gtcctgatca      1320
gagccgtggc cctttgggt gaactacctt ggttccccca ctgatcacaa aaacatggtg      1380
ggtccatggg cagagcccaa gggaattcgg tgtgcaccag ggttgacccc agaggattgc      1440
tgccccatca gtgctccctc acatgtcagt accttcaaac tagggccaag cccagcactg      1500
cttgaggaaa acaagcattc acaacttgtt tttggttttt aaaacccagt ccacaaaata      1560
```

| | |
|---|---|
| accaatcctg gacatgaaga ttctttccca attcacatct aacctcatct tcttcaccat | 1620 |
| ttggcaatgc catcatctcc tgccttcctc ctgggccctc tctgctctgc gtgtcacctg | 1680 |
| tgcttcgggc ccttcccaca ggacatttct ctaagagaac aatgtgctat gtgaagagta | 1740 |
| agtcaacctg cctgacattt ggagtgttcc ccttccactg agggcagtcg atagagctgt | 1800 |
| attaagccac ttaaaatgtt cacttttgac aaaggcaagc acttgtgggt ttttgttttg | 1860 |
| tttttcattc agtcttacga atacttttgc cctttgatta aagactccag ttaaaaaaaa | 1920 |
| ttttaatgaa gaaagtggaa acaaggaag tcaaagcaag gaaactatgt aacatgtagg | 1980 |
| aagtaggaag taaattatag tgatgtaatc ttgaattgta actgttcttg aatttaataa | 2040 |
| tctgtagggt aattagtaac atgtgttaag tattttcata agtatttcaa attggagctt | 2100 |
| catggcagaa ggcaaaccca tcaacaaaaa ttgtcccttaa aacaaaaatt aaaatcctca | 2160 |
| atccagctat gttatattga aaaatagag cctgagggat ctttactagt tataaagata | 2220 |
| cagaactctt tcaaaacctt ttgaaattaa cctctcacta taccagtata attgagtttt | 2280 |
| cagtggggca gtcattatcc aggtaatcca agatatttta aaatctgtca cgtagaactt | 2340 |
| ggatgtacct gcccccaatc catgaaccaa gaccattgaa ttcttggttg aggaaacaaa | 2400 |
| catgacccta aatcttgact acagtcagga aaggaatcat ttctatttct cctccatggg | 2460 |
| agaaaataga taagagtaga aactgcaggg aaaattattt gcataacaat tcctctacta | 2520 |
| acaatcagct ccttcctgga gactgcccag ctaaagcaat atgcatttaa atacagtctt | 2580 |
| ccatttgcaa gggaaaagtc tcttgtaatc cgaatctctt tttgctttcg aactgctagt | 2640 |
| caagtgcgtc cacgagctgt ttactaggga tccctcatct gtccctccgg gacctggtgc | 2700 |
| tgcctctacc tgacactccc ttgggctccc tgtaacctct tcagaggccc tcgctgccag | 2760 |
| ctctgtatca ggacccagag gaagggggcca gaggctcgtt gactggctgt gtgttgggat | 2820 |
| tgagtctgtg ccacgtgttt tgtctgtggt gtgtcccct ctgtccaggc actgagatac | 2880 |
| cagcgaggag gctccagagg gcactctgct tgttattaga gattacctcc tgagaaaaaa | 2940 |
| ggttccgctt ggagcagagg ggctgaatag cagaaggttg cacctccccc aaccttagat | 3000 |
| gttctaagtc tttccattgg atctcattgg acccttccat ggtgtgatcg tctgactggt | 3060 |
| gttatcaccg tgggctccct gactgggagt tgatcgcctt tcccaggtgc tacacccttt | 3120 |
| tccagctgga tgagaatttg agtgctctga tccctctaca gagcttccct gactcattct | 3180 |
| gaaggagccc cattcctggg aaatattccc tagaaacttc caaatcccct aagcagacca | 3240 |
| ctgataaaac catgtagaaa atttgttatt ttgcaacctc gctggactct cagtctctga | 3300 |
| gcagtgaatg attcagtgtt aaatgtgatg aatactgtat tttgtattgt ttcaattgca | 3360 |
| tctcccagat aatgtgaaaa tggtccagga gaaggccaat tcctatacgc agcgtgcttt | 3420 |
| aaaaaataaa taagaaacaa ctctttgaga aacaacaatt tctactttga agtcatacca | 3480 |
| atgaaaaaat gtatatgcac ttataatttt cctaataaag ttctgtactc aaatgtagcc | 3540 |
| accaa | 3545 |

<210> SEQ ID NO 34
<211> LENGTH: 2896
<212> TYPE: DNA
<213> ORGANISM: Homo sapiens

<400> SEQUENCE: 34

| | |
|---|---|
| ccactctaag gaatgcggtc cctttgacag gcgaaaaact gaagttggaa aagacaaagt | 60 |
| gatttgttca aaattgaaat ttgaaacttg acatttggtc agtgggccct atgtaggaaa | 120 |

```
aaacctccaa gagagctagg gttcctctca gagaggaaag acaggtcctt aggtcctcac    180
cctcccgtct ccttgccctt gcagttctgg gaactggaca gattggacaa ctataacgac    240
acctccctgg tggaaaatca tctctgccct gccacagagg ggcccctcat ggcctccttc    300
aaggccgtgt tcgtgcccgt ggcctacagc ctcatcttcc tcctgggcgt gatcggcaac    360
gtcctggtgc tggtgatcct ggagcggcac cggcagacac gcagttccac ggagaccttc    420
ctgttccacc tggccgtggc cgacctcctg ctggtcttca tcttgccctt tgccgtggcc    480
gagggctctg tgggctgggt cctggggacc ttcctctgca aaactgtgat tgccctgcac    540
aaagtcaact tctactgcag cagcctgctc ctggcctgca tcgccgtgga ccgctacctg    600
gccattgtcc acgccgtcca tgcctaccgc caccgccgcc tcctctccat ccacatcacc    660
tgtgggacca tctggctggt gggcttcctc cttgccttgc cagagattct cttcgccaaa    720
gtcagccaag gccatcacaa caactccctg ccacgttgca ccttctccca agagaaccaa    780
gcagaaacgc atgcctggtt cacctcccga ttcctctacc atgtggcggg attcctgctg    840
cccatgctgg tgatgggctg tgtgctacgtg ggggtagtgc acaggttgcg ccaggcccag    900
cggcgccctc agcggcagaa ggcagtcagg gtggccatcc tggtgacaag catcttcttc    960
ctctgctggt caccctacca catcgtcatc ttcctggaca ccctggcgag gctgaaggcc   1020
gtggacaata cctgcaagct gaatggctct ctccccgtgg ccatcaccat gtgtgagttc   1080
ctgggcctgg cccactgctg cctcaacccc atgctctaca cttttcgccgg cgtgaagttc   1140 cgcagtgacc tgtcgcggct cctgacgaag ctgggctgta ccggccctgc ctccctgtgc   1200
cagctcttcc ctagctggcg caggagcagt ctctctgagt cagagaatgc cacctctctc   1260
accacgttct aggtcccagt gtccccttttt attgctgctt ttccttgggg caggcagtga   1320
tgctggatgc tccttccaac aggagctggg atcctaaggg ctcaccgtgg ctaagagtgt   1380
cctaggagta tcctcatttg gggtagctag aggaaccaac ccccatttct agaacatccc   1440
tgccagctct tctgccggcc ctgggctag gctggagccc agggagcgga aagcagctca   1500
aaggcacagt gaaggctgtc cttacccatc tgcaccccc tgggctgaga gaacctcacg   1560
cacctcccat cctaatcatc caatgctcaa gaaacaactt ctacttctgc ccttgccaac   1620
ggagagcgcc tgcccctccc agaacacact ccatcagctt aggggctgct gacctccaca   1680 gcttccccte tctcctcctg cccacctgtc aaacaaagcc agaagctgag caccagggga   1740
tgagtggagg ttaaggctga ggaaaggcca gctggcagca gagtgtggcc ttcggacaac   1800
tcagtcccta aaaacacaga cattctgcca ggccccaag cctgcagtca tcttgaccaa   1860
gcaggaagct cagactggtt gagttcaggt agctgcccct ggctctgacc gaaacagcgc   1920
tgggtccacc ccatgtcacc ggatcctggg tggtctgcag gcagggctga ctctaggtgc   1980
ccttggaggc cagccagtga cctgaggaag cgtgaaggcc gagaagcaag aaagaaaccc   2040
gacagaggga agaaaagagc tttcttcccg aaccccaagg agggagatgg atcaatcaaa   2100
cccggcggtc ccctccgcca ggcgagatgg ggtggggtgg agaactccta gggtggctgg   2160
gtccagggga tgggaggttg tgggcattga tgggaagga ggctggcttg tccctcctc   2220 actcccttcc cataagctat agacccgagg aaactcagag tcggaacgga gaaaggtgga   2280
ctggaagggg cccgtgggag tcatctcaac catcccctcc gtggcatcac cttaggcagg   2340
gaagtgtaag aaacacactg aggcagggaa gtccccaggc ccaggaagc cgtgccctgc   2400 ccccgtgagg atgtcactca gatggaaccg caggaagctg ctccgtgctt gtttgctcac   2460
ctggggtgtg ggaggcccgt ccggcagttc tgggtgctcc ctaccacctc cccagccttt   2520
```

-continued

```
gatcaggtgg ggagtcaggg accccctgccc ttgtcccact caagccaagc agccaagctc    2580
cttgggaggc cccactgggg aaataacagc tgtggctcac gtgagagtgt cttcacggca    2640
ggacaacgag gaagccctaa gacgtccctt ttttctctga gtatctcctc gcaagctggg    2700
taatcgatgg gggagtctga agcagatgca aagaggcaag aggctggatt ttgaattttc    2760
tttttaataa aaaggcacct ataaaacagg tcaatacagt acaggcagca cagagacccc    2820
cggaacaagc ctaaaaattg tttcaaaata aaaaccaaga agatgtcttc acatattgta    2880
aaaaaaaaaa aaaaaa                                                    2896
```

<210> SEQ ID NO 35
<211> LENGTH: 2919
<212> TYPE: DNA
<213> ORGANISM: Homo sapiens

<400> SEQUENCE: 35

```
aaaaaaaaaa agtgatgagt tgtgaggcag gtcgcggccc tactgcctca ggagacgatg      60
cgcagctcat ttgcttaaat ttgcagctga cggctgccac ctctctagag gcacctggcg     120
gggagcctct caacataaga cagtgaccag tctggtgact cacagccggc acagccatga     180
actacccgct aacgctggaa atggacctcg agaacctgga ggaccctgttc tgggaactgg     240 acagattgga caactataac gacacctccc tggtggaaaa tcatctctgc cctgccacag     300
aggggcccct catggcctcc ttcaaggccg tgttcgtgcc cgtggcctac agcctcatct     360
tcctcctggg cgtgatcggc aacgtcctgg tgctggtgat cctggagcgg caccggcaga     420
cacgcagttc cacggagacc ttcctgttcc acctggccgt ggccgacctc ctgctggtct     480
tcatcttgcc ctttgccgtg gccgagggct ctgtgggctg ggtcctgggg accttcctct     540
gcaaaactgt gattgccctg cacaaagtca acttctactg cagcagcctg ctcctggcct     600
gcatcgccgt ggaccgctac ctggccattg ccacgccgt ccatgcctac cgccaccgcc     660
gcctcctctc catccacatc acctgtggga ccatctggct ggtgggcttc ctccttgcct     720
tgccagagat tctcttcgcc aaagtcagcc aaggccatca caacaactcc ctgccacgtt     780
gcaccttctc ccaagagaac caagcagaaa cgcatgcctg gttcacctcc cgattcctct     840
accatgtggc gggattcctg ctgcccatgc tggtgatggg ctggtgctac gtgggggtag     900
tgcacaggtt gcgccaggcc cagcggcgcc ctcagcggca aaggcagtc agggtggcca     960 tcctggtgac aagcatcttc ttcctctgct ggtcaccctta ccacatcgtc atcttcctgg    1020 acacccctggc gaggctgaag gccgtggaca ataacctgcaa gctgaatggc tctctccccg    1080
tggccatcac catgtgtgag ttcctgggcc tggcccactg ctgcctcaac cccatgctct    1140
acactttcgc cggcgtgaag ttccgcagtg acctgtcgcg gctcctgacg aagctgggct    1200
gtaccggccc tgcctccctg tgccagctct tccctagctg gcgcaggagc agtctctctg    1260
agtcagagaa tgccacctct ctcaccacgt tctaggtccc agtgtcccct tttattgctg    1320
cttttccttg gggcaggcag tgatgctgga tgctccttcc aacaggagct gggatcctaa    1380
gggctcaccg tggctaagag tgtcctagga gtatcctcat ttgggtagc tagaggaacc    1440 aaccccccatt tctagaacat ccctgccagc tcttctgccg gccctgggc taggctggag    1500 cccagggagc ggaaagcagc tcaaaggcac agtgaaggct gtccttaccc atctgcaccc    1560
ccctgggctg agagaacctc acgcacctcc catcctaatc atccaatgct caagaaacaa    1620
cttctacttc tgcccttgcc aacggagagc gcctgcccct cccagaacac actccatcag    1680
cttaggggct gctgacctcc acagcttccc ctctctcctc ctgcccacct gtcaaacaaa    1740
```

-continued

| | |
|---|---|
| gccagaagct gagcaccagg ggatgagtgg aggttaaggc tgaggaaagg ccagctggca | 1800 |
| gcagagtgtg gccttcggac aactcagtcc ctaaaaacac agacattctg ccaggccccc | 1860 |
| aagcctgcag tcatcttgac caagcaggaa gctcagactg gttgagttca ggtagctgcc | 1920 |
| cctggctctg accgaaacag cgctgggtcc accccatgtc accggatcct gggtggtctg | 1980 |
| caggcagggc tgactctagg tgcccttgga ggccagccag tgacctgagg aagcgtgaag | 2040 |
| gccgagaagc aagaaagaaa cccgacagag ggaagaaaag agctttcttc ccgaacccca | 2100 |
| aggagggaga tggatcaatc aaacccggcg gtccctccg ccaggcgaga tggggtgggg | 2160 |
| tggagaactc ctagggtggc tgggtccagg ggatgggagg ttgtgggcat tgatggggaa | 2220 |
| ggaggctggc ttgtcccctc ctcactccct tcccataagc tatagacccg aggaaactca | 2280 |
| gagtcggaac ggagaaaggt ggactggaag gggcccgtgg gagtcatctc aaccatcccc | 2340 |
| tccgtggcat caccttaggc agggaagtgt aagaaacaca ctgaggcagg gaagtcccca | 2400 |
| ggccccagga agccgtgccc tgcccccgtg aggatgtcac tcagatggaa ccgcaggaag | 2460 |
| ctgctccgtg cttgtttgct cacctggggt gtgggaggcc cgtccggcag ttctgggtgc | 2520 |
| tccctaccac ctccccagcc tttgatcagg tggggagtca gggacccctg cccttgtccc | 2580 |
| actcaagcca agcagccaag ctccttggga ggccccactg gggaaataac agctgtggct | 2640 |
| cacgtgagag tgtcttcacg gcaggacaac gaggaagccc taagacgtcc cttttttctc | 2700 |
| tgagtatctc ctcgcaagct gggtaatcga tgggggagtc tgaagcagat gcaaagaggc | 2760 |
| aagaggctgg attttgaatt ttcttttttaa taaaaaggca cctataaaac aggtcaatac | 2820 |
| agtacaggca gcacagagac ccccggaaca agcctaaaaa ttgtttcaaa ataaaaacca | 2880 |
| agaagatgtc ttcacatatt gtaaaaaaaa aaaaaaaa | 2919 |

<210> SEQ ID NO 36
<211> LENGTH: 1219
<212> TYPE: DNA
<213> ORGANISM: Homo sapiens

<400> SEQUENCE: 36

| | |
|---|---|
| gagaagatgt ttgaaaaaac tgactctgct aatgagcctg gactcagagc tcaagtctga | 60 |
| actctacctc cagacagaat gaagttcatc tcgacatctc tgcttctcat gctgctggtc | 120 |
| agcagcctct ctccagtcca aggtgttctg gaggtctatt acacaagctt gaggtgtaga | 180 |
| tgtgtccaag agagctcagt ctttatccct agacgcttca ttgatcgaat tcaaatcttg | 240 |
| ccccgtggga atggttgtcc aagaaaagaa atcatagtct ggaagaagaa caagtcaatt | 300 |
| gtgtgtgtgg accctcaagc tgaatggata caaagaatga tggaagtatt gagaaaaaga | 360 |
| agttcttcaa ctctaccagt tccagtgttt aagagaaaga ttccctgatg ctgatatttc | 420 |
| cactaagaac acctgcattc ttcccttatc cctgctctgg attttagttt tgtgcttagt | 480 |
| taaatctttt ccaggaaaaa gaacttcccc atacaaataa gcatgagact atgtaaaaat | 540 |
| aaccttgcag aagctgatgg ggcaaactca agcttcttca ctcacagcac cctatataca | 600 |
| cttggagttt gcattcttat tcatcaggga ggaaagtttc tttgaaaata gttattcagt | 660 |
| tataagtaat acaggattat tttgattata tacttgttgt ttaatgttta aaatttctta | 720 |
| gaaacaatg gaatgagaat ttaagcctca aattgaaca tgtggcttga attaagaaga | 780 |
| aaattatggc atatattaaa agcaggcttc tatgaaagac tcaaaagct gcctgggagg | 840 |
| cagatggaac ttgagcctgt caagaggcaa aggaatccat gtagtagata tcctctgctt | 900 |
| aaaaactcac tacggaggag aattaagtcc tactttaaa gaatttcttt ataaaattta | 960 |

| | |
|---|---|
| ctgtctaaga ttaatagcat tcgaagatcc ccagacttca tagaatactc agggaaagca | 1020 |
| tttaaagggt gatgtacaca tgtatccttt cacacatttg ccttgacaaa cttctttcac | 1080 |
| tcacatcttt ttcactgact ttttttgtgg ggggcggggc cggggggact ctggtatcta | 1140 |
| attcttaat gattcctata aatctaatga cattcaataa agttgagcaa acattttact | 1200 |
| taaaaaaaaa aaaaaaaaa | 1219 |

<210> SEQ ID NO 37
<211> LENGTH: 1953
<212> TYPE: DNA
<213> ORGANISM: Homo sapiens

<400> SEQUENCE: 37

| | |
|---|---|
| gcagaccttg cttcatgagc aagctcatct ctggaacaaa ctggcaaagc atctctgctg | 60 |
| gtgttcatca gaacagacac catggcagag catgattacc atgaagacta tgggttcagc | 120 |
| agtttcaatg acagcagcca ggaggagcat caagacttcc tgcagttcag caaggtcttt | 180 |
| ctgccctgca tgtacctggt ggtgtttgtc tgtggtctgg tggggaactc tctggtgctg | 240 |
| gtcatatcca tcttctacca taagttgcag agcctgacgg atgtgttcct ggtgaaccta | 300 |
| cccctggctg acctggtgtt tgtctgcact ctgcccttct gggcctatgc aggcatccat | 360 |
| gaatgggtgt ttggccaggt catgtgcaag agcctactgg catctacac tattaacttc | 420 |
| tacacgtcca tgctcatcct cacctgcatc actgtggatc gtttcattgt agtggttaag | 480 |
| gccaccaagg cctacaacca gcaagccaag aggatgacct gggcaaggt caccagcttg | 540 |
| ctcatctggg tgatatccct gctggtttcc ttgccccaaa ttatctatgg caatgtcttt | 600 |
| aatctcgaca agctcatatg tggttaccat gacgaggcaa tttccactgt ggttcttgcc | 660 |
| acccagatga cactggggtt cttcttgcca ctgctcacca tgattgtctg ctattcagtc | 720 |
| ataatcaaaa cactgcttca tgctggaggc ttccagaagc acagatctct aaagatcatc | 780 |
| ttcctggtga tggctgtgtt cctgctgacc cagatgccct tcaacctcat gaagttcatc | 840 |
| cgcagcacac actgggaata ctatgccatg accagctttc actacaccat catggtgaca | 900 |
| gaggccatcg catacctgag gccctgcctt aaccctgtgc tctatgcctt tgtcagcctg | 960 |
| aagtttcgaa agaacttctg gaaacttgtg aaggacattg gttgcctccc ttaccttggg | 1020 |
| gtctcacatc aatggaaatc ttctgaggac aattccaaga cttttctgc ctcccacaat | 1080 |
| gtggaggcca ccagcatgtt ccagttatag gccttgccag ggtttcgaga agctgctctg | 1140 |
| gaatttgcaa gtcatggctg tgccctcttg atgtggtgag gcaggctttg tttatagctt | 1200 |
| gcgcattctc atggagaagt tatcagacac tctggctggt ttggaatgct tcttctcagg | 1260 |
| catgaacatg tactgttctc ttcttgaaca ctcatgctga aagcccaagt agggggtcta | 1320 |
| aaattttaa ggactttcct tcctccatct ccaagaatgc tgaaaccaag ggggatgaca | 1380 |
| tgtgactcct atgatctcag gttctccttg attgggactg gggctgaagg ttgaagaggt | 1440 |
| gagcacggcc aacaaagctg ttgatggtag gtggcacact gggtgcccaa gctcagaagg | 1500 |
| ctcttctgac tactgggcaa agagtgtaga tcagagcagc agtgaaaaca agtgctggca | 1560 |
| ccaccaggca cctcacagaa atgagatcag gctctgcctc accttggggc ttgactttg | 1620 |
| tataggtaga tgttcagatt gctttgatta atccagaata actagcacca gggactatga | 1680 |
| atgggcaaaa ctgaattata agaggctgat aattccagtg gtccatggaa tgcttgaaaa | 1740 |
| atgtgcaaaa cagcgtttaa gactgtaatg aatctaagca gcatttctga agtggactct | 1800 |
| ttggtggctt tgcatttaa aaatgaaatt ttccaatgtc tgccacacaa acgtatgtaa | 1860 |

| | |
|---|---:|
| atgtatatac ccacacacat acacacatat gtcatatatt actagcatat gagtttcata | 1920 |
| gctaagaaat aaaactgtta aagtctccaa act | 1953 |

<210> SEQ ID NO 38
<211> LENGTH: 2344
<212> TYPE: DNA
<213> ORGANISM: Homo sapiens

<400> SEQUENCE: 38

| | |
|---|---:|
| ggtgcgtccg cgggtggctg ccccgcaggt gcgcgcggcc ggggctggcg gcgactctct | 60 |
| ccaccgggcc gcccgggagg ctcatgcagc gcggctgggt cccgcggcgc ccggatcggg | 120 |
| gaagtgaaag tgcctcggag gaggagggcc ggtccggcag tgcagccgcc tcacaggtcg | 180 |
| gcggacgggc caggcgggcg gcctcctgaa ccgaaccgaa tcggctcctc gggccgtcgt | 240 |
| cctcccgccc ctcctcgccc gccgccggag tttctttcg gtttcttcca agattcctgg | 300 |
| ccttccctcg acgagccgg gcccagtgcg ggggcgcagg gcgcgggagc tccacctcct | 360 |
| cggctttccc tgcgtccaga ggctggcatg gcgcgggccg agtactgagc gcacggtcgg | 420 |
| ggcacagcag ggccgggggg tgcagctggc tcgcgcctcc tctccggccg ccgtctcctc | 480 |
| cggtccccgg cgaaagccat tgagacacca gctggacgtc acgcgccgga gcatgtctgg | 540 |
| gagtcagagc gaggtggctc catccccgca gagtccgcgg agcccgaga tgggacggga | 600 |
| cttgcggccc gggtcccgcg tgctcctgct cctgcttctg ctcctgctgg tgtacctgac | 660 |
| tcagccaggc aatggcaacg agggcagcgt cactggaagt tgttattgtg gtaaaagaat | 720 |
| ttcttccgac tccccgccat cggttcagtt catgaatcgt ctccggaaac acctgagagc | 780 |
| ttaccatcgg tgtctatact acacgaggtt ccagctcctt tcctggagcg tgtgtggggg | 840 |
| caacaaggac ccatgggttc aggaattgat gagctgtctt gatctcaaag aatgtggaca | 900 |
| tgcttactcg gggattgtgg cccaccagaa gcatttactt cctaccagcc ccccaatttc | 960 |
| tcaggcctca gaggggcat cttcagatat ccacaccct gcccagatgc tcctgtccac | 1020 |
| cttgcagtcc actcagcgcc ccaccctccc agtaggatca ctgtcctcgg acaaagagct | 1080 |
| cactcgtccc aatgaaacca ccattcacac tgcgggccac agtctggcag ctgggcctga | 1140 |
| ggctggggag aaccagaagc agccggaaaa aaatgctggt cccacagcca ggacatcagc | 1200 |
| cacagtgcca gtcctgtgcc tcctggccat catcttcatc ctcaccgcag ccctttccta | 1260 |
| tgtgctgtgc aagaggagga gggggcagtc accgcagtcc tctccagatc tgccggttca | 1320 |
| ttatatacct gtggcacctg actctaatac ctgagccaag aatggaagct tgtgaggaga | 1380 |
| cggactctat gttgcccagg ctgttatgga actcctgagt caagtgatcc tcccaccttg | 1440 |
| gcctctgaag gtgcgaggat tataggcgtc acctaccaca tccagcctac acgtatttgt | 1500 |
| taatatctaa cataggacta accagccact gccctctctt aggcccctca tttaaaaacg | 1560 |
| gttatactat aaaatctgct tttcacactg ggtgataata acttggacaa attctatgtg | 1620 |
| tattttgttt tgttttgctt tgctttgttt tgagacggag tctcgctctg tcatccaggc | 1680 |
| tggagtgcag tggcatgatc tcggctcact gcaaccccca tctcccaggt tcaagcgatt | 1740 |
| ctcctgcctc ctcctgagta gctgggacta caggtgctca ccaccacacc cggctaattt | 1800 |
| tttgtatttt tagtagagac ggggtttcac catgttgacc aggctggtct cgaactcctg | 1860 |
| acctggtgat ctgcccaccc aggcctccca aagtgctggg attaaaggtg tgagccacca | 1920 |
| tgcctggccc tatgtgtgtt ttttaactac taaaaattat ttttgtaatg attgagtctt | 1980 |
| ctttatggaa acaactggcc tcagcccttg cgcccttact gtgattcctg gcttcatttt | 2040 |

```
ttgctgatgg ttcccctcg tcccaaatct ctctcccagt acaccagttg ttcctccccc    2100
acctcagccc tctcctgcat cctcctgtac ccgcaacgaa ggcctgggct ttcccaccct    2160
ccctccttag caggtgccgt gctgggacac catacgggtt ggtttcacct cctcagtccc    2220
ttgcctaccc cagtgagagt ctgatcttgt tttattgtt attgctttta ttattattgc     2280
ttttattatc attaaaactc tagttcttgt tttgtctctc cgaaaaaaaa aaaaaaaaaa    2340
aaaa                                                                 2344

<210> SEQ ID NO 39
<211> LENGTH: 1497
<212> TYPE: DNA
<213> ORGANISM: Homo sapiens

<400> SEQUENCE: 39
cggaccacca gcaacagaca acatcttcat tcggctctcc ctgaagctgt actgcctcgc      60
tgagaggatg aaggtctccg aggctgccct gtctctcctt gtcctcatcc ttatcattac     120
ttcggcttct cgcagccagc caaaagttcc tgagtgggtg aacacccccat ccacctgctg    180 cctgaagtat tatgagaaag tgttgccaag gagactagtg gtgggataca gaaaggccct    240
caactgtcac ctgccagcaa tcatcttcgt caccaagagg aaccgagaag tctgcaccaa    300
ccccaatgac gactgggtcc aagagtacat caaggatccc aacctacctt tgctgcctac    360
caggaacttg tccacggtta aaattattac agcaaagaat ggtcaacccc agctcctcaa    420
ctcccagtga tgaccaggct ttagtggaag cccttgttta cagaagagag gggtaaacct    480
atgaaaacag gggaagcctt attaggctga aactagccag tcacattgag agaagcagaa    540
caatgatcaa aataaaggag aagtatttcg aatattttct caatcttagg aggaaatacc    600
aaagttaagg gacgtgggca gaggtacgct ctttttatttt tatatttata ttttttatttt   660 tttgagatag ggtcttactc tgtcacccag gctggagtgc agtggtgtga tcttggctca     720
cttgatcttg gctcactgta acctccacct cccaggctca agtgatcctc ccaccccagc    780
ctcctgagta gctgggacta caggcttgcg ccaccacacc tggctaattt ttgtatttttt    840 ggtagagacg ggattctacc atgttgccca ggctggtctc aaactcgtgt gcccaagcaa    900
tccacctgcc tcagccttcc aaaagtgctg ggattacagg cgtgagccac cacatccggc    960
cagtgcactc ttaatacaca gaaaaatata tttcacatcc ttctcctgct ctctttcaat    1020
tcctcacttc acaccagtac acaagccatt ctaaatactt agccagtttc cagccttcca   1080
gatgatcttt gccctctggg tcttgaccca ttaagagccc catagaactc ttgatttttc    1140
ctgtccatct ttatggattt ttctggatct atatttctt caattattct ttcatttttat    1200 aatgcaactt tttcatagga agtccggatg gaatattca cattaatcat ttttgcagag    1260
actttgctag atcctctcat attttgtctt cctcagggtg gcaggggtac agagagtgcc    1320
tgattggaaa aaaaaaaaa agagagagag agaagaaag aagaagaaga gacacaaatc    1380
tctacctccc atgttaagct ttgcaggaca gggaagaaa gggtatgaga cacggctagg    1440
ggtaaactct tagtccaaaa cccaagcatg caataaataa aactcccctta tttgaca      1497

<210> SEQ ID NO 40
<211> LENGTH: 1002
<212> TYPE: DNA
<213> ORGANISM: Homo sapiens

<400> SEQUENCE: 40
agatgggaca gcttggccta cagcccggcg ggcatcagct cccttgaccc agtggatatc      60
```

| | |
|---|---|
| ggtggcccg ttattcgtcc aggtgcccag ggaggaggac ccgcctgcag catgaacctg | 120 |
| tggctcctgg cctgcctggt ggccggcttc ctgggagcct gggcccccgc tgtccacacc | 180 |
| caaggtgtct ttgaggactg ctgcctggcc taccactacc ccattgggtg gctgtgctc | 240 |
| cggcgcgcct ggacttaccg gatccaggag gtgagcggga gctgcaatct gcctgctgcg | 300 |
| atattctacc tccccaagag acacaggaag gtgtgtggga accccaaaag cagggaggtg | 360 |
| cagagagcca tgaagctcct ggatgctcga aataaggttt ttgcaaagct ccaccacaac | 420 |
| acgcagacct tccaagcagg ccctcatgct gtaaagaagt tgagttctgg aaactccaag | 480 |
| ttatcatcgt ccaagtttag caatcccatc agcagcagta agaggaatgt ctccctcctg | 540 |
| atatcagcta attcaggact gtgagccggc tcatttctgg gctccatcgg cacaggaggg | 600 |
| gccggatctt tctccgataa aaccgtcgcc ctacagaccc agctgtcccc acgcctctgt | 660 |
| cttttgggtc aagtcttaat ccctgcacct gagttggtcc tccctctgca cccccaccac | 720 |
| ctcctgcccg tctggcaact ggaaagaggg agttggcctg atttttaagcc ttttgccgct | 780 |
| ccggggacca gcagcaatcc tgggcagcca gtggctcttg tagagaagac ttaggatacc | 840 |
| tctctcactt tctgttttctt gccgtccacc ccgggccatg ccagtgtgtc cctctgggtc | 900 |
| cctccaaaac tctggtcagt tcaaggatgc ccctcccagg ctatgctttt ctataacttt | 960 |
| taaataaacc ttgggggggtg atggagtcat tcctgcctgt ta | 1002 |

<210> SEQ ID NO 41
<211> LENGTH: 1002
<212> TYPE: DNA
<213> ORGANISM: Homo sapiens

<400> SEQUENCE: 41

| | |
|---|---|
| agatgggaca gcttggccta cagcccggcg ggcatcagct cccttgaccc agtggatatc | 60 |
| ggtggcccg ttattcgtcc aggtgcccag ggaggaggac ccgcctgcag catgaacctg | 120 |
| tggctcctgg cctgcctggt ggccggcttc ctgggagcct gggcccccgc tgtccacacc | 180 |
| caaggtgtct ttgaggactg ctgcctggcc taccactacc ccattgggtg gctgtgctc | 240 |
| cggcgcgcct ggacttaccg gatccaggag gtgagcggga gctgcaatct gcctgctgcg | 300 |
| atattctacc tccccaagag acacaggaag gtgtgtggga accccaaaag cagggaggtg | 360 |
| cagagagcca tgaagctcct ggatgctcga aataaggttt ttgcaaagct ccaccacaac | 420 |
| acgcagacct tccaagcagg ccctcatgct gtaaagaagt tgagttctgg aaactccaag | 480 |
| ttatcatcgt ccaagtttag caatcccatc agcagcagta agaggaatgt ctccctcctg | 540 |
| atatcagcta attcaggact gtgagccggc tcatttctgg gctccatcgg cacaggaggg | 600 |
| gccggatctt tctccgataa aaccgtcgcc ctacagaccc agctgtcccc acgcctctgt | 660 |
| cttttgggtc aagtcttaat ccctgcacct gagttggtcc tccctctgca cccccaccac | 720 |
| ctcctgcccg tctggcaact ggaaagaggg agttggcctg atttttaagcc ttttgccgct | 780 |
| ccggggacca gcagcaatcc tgggcagcca gtggctcttg tagagaagac ttaggatacc | 840 |
| tctctcactt tctgttttctt gccgtccacc ccgggccatg ccagtgtgtc cctctgggtc | 900 |
| cctccaaaac tctggtcagt tcaaggatgc ccctcccagg ctatgctttt ctataacttt | 960 |
| taaataaacc ttgggggggtg atggagtcat tcctgcctgt ta | 1002 |

<210> SEQ ID NO 42
<211> LENGTH: 744
<212> TYPE: DNA
<213> ORGANISM: Homo sapiens

```
<400> SEQUENCE: 42
atgaacctgt ggctcctggc ctgcctggtg gccggcttcc tgggagcctg ggccccgct      60 gtccacaccc aagtgtgtct tgaggactgc tgcctggcct accactaccc cattgggtgg    120
gctgtgctcc ggcgcgcctg gacttaccgg atccaggagg tgagcgggag ctgcaatctg    180
cctgctgcga tcaggccctc atgctgtaaa gaagttgagt tctggaaact ccaagttatc    240
atcgtccaag tttagcaatc ccatcagcag cagtaagagg aatgtctccc tcctgatatc    300
agctaattca ggactgtgag ccggctcatt tctgggctcc atcggcacag gaggggccgg    360
atctttctcc gataaaaccg tcgccctaca gacccagctg tccccacgcc tctgtctttt    420
gggtcaagtc ttaatccctg cacctgagtt ggtcctccct ctgcacccec accacctcct    480 gcccgtctgg caactggaaa gagggagttg gcctgatttt aagccttttg ccgctccggg    540
gaccagcagc aatcctgggc agccagtggc tcttgtagag aagacttagg atacctctct    600
cactttctgt ttcttgccgt ccaccccggg ccatgccagt gtgtccctct gggtccctcc    660
aaaactctgg tcagttcaag gatgcccctc ccaggctatg cttttctata acttttaaat    720
aaaccttggg gggtgatgga gtca                                           744

<210> SEQ ID NO 43
<211> LENGTH: 3108
<212> TYPE: DNA
<213> ORGANISM: Homo sapiens

<400> SEQUENCE: 43
gaaatactcg tctctggtaa agtctgagca ggacagggtg gctgactggc agatccagag     60
gttcccttgg cagtccacgc caggccttca ccatggatca gttccctgaa tcagtgacag    120
aaaactttga gtacgatgat ttggctgagg cctgttatat tggggacatc gtggtctttg    180
ggactgtgtt cctgtccata ttctactccg tcatctttgc cattggcctg gtgggaaatt    240
tgttggtagt gtttgccctc accaacagca agaagcccaa gagtgtcacc gacatttacc    300
tcctgaacct ggccttgtct gatctgctgt ttgtagccac tttgcccttc tggactcact    360
atttgataaa tgaaagggc ctccacaatg ccatgtgcaa attcactacc gccttcttct    420
tcatcggctt ttttggaagc atattcttca tcaccgtcat cagcattgat aggtacctgg    480
ccatcgtcct ggccgccaac tccatgaaca accggaccgt gcagcatggc gtcaccatca    540
gcctaggcgt ctgggcagca gccatttggg tggcagcacc ccagttcatg ttcacaaagc    600
agaaagaaaa tgaatgcctt ggtgactacc ccgaggtcct ccaggaaatc tggcccgtgc    660
tccgcaatgt ggaaacaaat tttcttggct tcctactccc cctgctcatt atgagttatt    720
gctacttcag aatcatccag acgctgtttt cctgcaagaa ccacaagaaa gccaaagcca    780
ttaaactgat ccttctggtg gtcatcgtgt ttttcctctt ctggacaccc tacaacgtta    840
tgattttcct ggagacgctt aagctctatg acttctttcc cagttgtgac atgaggaagg    900
atctgaggct ggccctcagt gtgactgaga cggttgcatt tagccattgt gcctgaatc     960 ctctcatcta tgcatttgct ggggagaagt tcagaagata cctttaccac ctgtatgga   1020 aatgcctggc tgtcctgtgt gggcgctcag tccacgttga tttctcctca tctgaatcac   1080
aaaggagcag gcatggaagt gttctgagca gcaattttac ttaccacacg agtgatggag   1140
atgcattgct ccttctctga agggaatccc aaagccttgt gtctacagag aacctggagt   1200
tcctgaacct gatgctgact agtgaggaaa gattttgtt gttatttctt acaggcacaa   1260
aatgatggac ccaatgcaca caaaacaacc ctagagtgtt gttgagaatt gtgctcaaaa  1320
```

-continued

| | |
|---|---|
| tttgaagaat gaacaaattg aactctttga atgacaaaga gtagacattt ctcttactgc | 1380 |
| aaatgtcatc agaacttttt ggtttgcaga tgacaaaaat tcaactcaga ctagtttagt | 1440 |
| taaatgaggg tggtgaatat tgttcatatt gtggcacaag caaaagggtg tctgagccct | 1500 |
| caaagtgagg ggaaaccagg gcctgagcca agctagaatt ccctctctct gactctcaaa | 1560 |
| tcttttagtc attatagatc ccccagactt tacatgacac agctttatca ccagagaggg | 1620 |
| actgacaccc atgtttctct ggccccaagg gcaaaattcc agggaagtg tctctgatagg | 1680 |
| ccaagtttgt atcaggtgcc catccctgga aggtgctgtt atccatgggg aagggatata | 1740 |
| taagatggaa gcttccagtc caatctcatg gagaagcaga aatacatatt tccaagaagt | 1800 |
| tggatgggtg ggtactattc tgattacaca aaacaaatgc cacacatcac ccttaccatg | 1860 |
| tgcctgatcc agcctctccc ctgattacac cagcctcgtc ttcattaagc cctcttccat | 1920 |
| catgtcccca acctgcaag gctccccac tgcctactgc atcgagtcaa aactcaaatg | 1980 |
| cttggcttct catacgtcca ccatgggtc ctaccaatag attccccatt gcctcctcct | 2040 |
| tcccaaagga ctccacccat cctatcagcc tgtctcttcc atatgacctc atgcatctcc | 2100 |
| acctgctccc aggccagtaa gggaaataga aaaccctgc ccccaaataa gaagggatgg | 2160 |
| attccaaccc caactccagt agcttgggac aaatcaagct tcagtttcct ggtctgtaga | 2220 |
| agagggataa ggtacctttc acatagagat catcctttcc agcatgagga actagccacc | 2280 |
| aactcttgca ggtctcaacc cttttgtctg cctcttagac ttctgctttc cacacctggc | 2340 |
| actgctgtgc tgtgcccaag ttgtggtgct gacaaagctt ggaagagcct gcaggtgctg | 2400 |
| ctgcgtggca tagcccagac acagaagagg ctggttctta cgatggcacc cagtgagcac | 2460 |
| tcccaagtct acagagtgat agccttccgt aacccaactc tcctggactg ccttgaatat | 2520 |
| cccctcccag tcaccttgtg gcaagcccct gcccatctgg gaaaataccc catcattcat | 2580 |
| gctactgcca acctggggag ccagggctat gggagcagct ttttttttccc ccctagaaac | 2640 |
| gtttggaaca atctaaaagt ttaaagctcg aaaacaattg taataatgct aaagaaaaag | 2700 |
| tcatccaatc taaccacatc aatattgtca ttcctgtatt cacccgtcca gaccttgttc | 2760 |
| acactctcac atgtttagag ttgcaatcgt aatgtacaga tggttttata atctgatttg | 2820 |
| ttttcctctt aacgttagac cacaaatagt gctcgctttc tatgtagttt ggtaattatc | 2880 |
| attttagaag actctaccag actgtgtatt cattgaagtc agatgtggta actgttaaat | 2940 |
| tgctgtgtat ctgatagctc tttggcagtc tatatgtttg tataatgaat gagagaataa | 3000 |
| gtcatgttcc ttcaagatca tgtaccccaa tttacttgcc attactcaat tgataaacat | 3060 |
| ttaacttgtt tccaatgttt agcaaataca tattttatag aacttcca | 3108 |

<210> SEQ ID NO 44
<211> LENGTH: 3304
<212> TYPE: DNA
<213> ORGANISM: Homo sapiens

<400> SEQUENCE: 44

| | |
|---|---|
| ctgagctctg ccgcctggct ctagccgcct gcctggcccc cgccgggact cttgcccacc | 60 |
| ctcagccatg gctccgatat ctctgtcgtg gctgctccgc ttggccacct tctgccatct | 120 |
| gactgtcctg ctggctggac agcaccacgg tgtgacgaaa tgcaacatca cgtgcagcaa | 180 |
| gatgacatca aagataccctg tagctttgct catccactat caacagaacc aggcatcatg | 240 |
| cggcaaacgc gcaatcatct tggagacgag acagcacagg ctgttctgtg ccgacccgaa | 300 |
| ggagcaatgg gtcaaggacg cgatgcagca tctggaccgc caggctgctg ccctaactcg | 360 |

```
aaatggcggc accttcgaga agcagatcgg cgaggtgaag cccaggacca cccctgccgc    420
cgggggaatg gacgagtctg tggtcctgga gcccgaagcc acaggcgaaa gcagtagcct    480
ggagccgact ccttcttccc aggaagcaca gagggccctg ggacctccc  cagagctgcc    540 gacgggcgtg actggttcct cagggaccag gctcccccg  acgccaaagg ctcaggatgg    600
agggcctgtg ggcacggagc ttttccgagt gcctcccgtc tccactgccg ccacgtggca    660
gagttctgct ccccaccaac ctgggcccag cctctgggct gaggcaaaga cctctgaggc    720
cccgtccacc caggacccct ccacccaggc ctccactgcg tcctcccag  ccccagagga    780 gaatgctccg tctgaaggcc agcgtgtgtg gggtcaggga cagagcccca ggccagagaa    840
ctctctggag cgggaggaga tgggtcccgt gccagcgcac acggatgcct tccaggactg    900
ggggcctggc agcatggccc acgtctctgt ggtccctgtc tcctcagaag gaccccccag    960
cagggagcca gtggcttcag gcagctggac ccctaaggct gaggaaccca tccatgccac   1020
catggacccc cagaggctgg gcgtccttat cactcctgtc cctgacgccc aggctgccac   1080
ccggaggcag gcggtggggc tgctggcctt ccttggcctc ctcttctgcc tgggggtggc   1140
catgttcacc taccagagcc tccagggctg ccctcgaaag atggcaggag agatggcgga   1200
gggccttcgc tacatccccc ggagctgtgg tagtaattca tatgtcctgg tgcccgtgtg   1260
aactcctctg gcctgtgtct agttgtttga ttcagacagc tgcctgggat ccctcatcct   1320
catacccacc cccacccaag ggcctggcct gagctgggat gattggaggg gggaggtggg   1380 atcctcagg  tgcacaagct ccaagctccc aggcattccc caggaggcca gccttgacca   1440
ttctccacct tccagggaca gaggggggtgg cctcccaact caccccagcc ccaaaactct   1500
cctctgctgc tggctggtta gaggttccct ttgacgccat cccagcccca atgaacaatt   1560
atttattaaa tgcccagccc cttctgaccc atgctgccct gtgagtacta cagtcctccc   1620
atctcacaca tgagcatcag gccaggccct ctgccactc  cctgcaacct gattgtgtct   1680
cttggtcctg ctgcagttgc cagtcacccc ggccacctgc ggtgctatct cccccagccc   1740
catcctctgt acagagccca cgccccact  ggtgacatgt ctttcttgc  atgaggctag   1800 tgtggtgttt cctggcactg cttccagtga ggctctgccc ttggttaggc attgtgggaa   1860
ggggagataa gggtatctgg tgactttcct cttggtcta  cactgtgctg agtctgaagg   1920
ctgggttctg atcctagttc caccatcaag ccaccaacat actcccatct gtgaaaggaa   1980
agagggaggt aaggaatacc tgtcccctg  acaacactca ttgacctgag gcccttctct   2040
ccagcccctg gatgcagcct cacagtcctt accagcagag caccttagac agtccctgcc   2100
aatggactaa cttgtctttg gaccctgagg cccagagggc ctgcaaggga gtgagttgat   2160
agcacagacc ctgccctgtg gcccccaaa  tggaaatggg cagagcagag accatccctg   2220
aaggccccgc ccaggcttag tcactgagac agcccgggct ctgcctccca tcaccgcta   2280 agagggaggg agggctccag acacatgtcc aagaagccca ggaaaggctc caggagcagc   2340
cacattcctg atgcttcttc agagactcct gcaggcagcc aggccacaag accttgtgg   2400 tcccacccca cacgccag  attctttcct gaggctgggc tcccttccca cctctctcac   2460
tccttgaaaa cactgttctc tgccctccaa gaccttctcc ttcacctttg tccccaccgc   2520
agacaggacc agggatttcc atgatgtttt ccatgagtcc cctgtttgtt tctgaaaggg   2580
acgctacccg ggaagggggc tgggacatgg gaaagggaa  gttgtaggca taaagtcagg   2640
ggttcccttt tttggctgct gaaggctcga gcatgcctgg atgggctgc  accggctggc   2700 ctggcccctc agggtccctg gtggcagctc acctctccct tggattgtcc ccgacccttg   2760
```

```
ccgtctacct gaggggcctc ttatgggctg ggttctaccc aggtgctagg aacactcctt    2820
cacagatggg tgcttggagg aaggaaaccc agctctggtc catagagagc aagacgctgt    2880
gctgccctgc ccacctggcc tctgcactcc cctgctgggt gtggcgcagc atattcagga    2940
agctcagggc ctggctcagg tggggtcact ctggcagctc agagagggtg ggagtgggtc    3000
caatgcactt tgttctggct cttccaggct gggagagcct ttcaggggtg ggacaccctg    3060
tgatggggcc ctgcctcctt tgtgaggaag ccgctgggc cagttggtcc cccttccatg     3120
gactttgtta gtttctccaa gcaggacatg gacaaggatg atctaggaag actttggaaa    3180
gagtaggaag actttggaaa gacttttcca accctcatca ccaacgtctg tgccattttg    3240
tattttacta ataaaattta aaagtcttgt gaaaaaaaaa aaaaaaaaaa aaaaaaaaaa    3300
aaaa                                                                3304
```

<210> SEQ ID NO 45
<211> LENGTH: 16
<212> TYPE: PRT
<213> ORGANISM: Homo sapiens

<400> SEQUENCE: 45

```
Arg Ser Ser Ser Thr Leu Pro Val Pro Val Phe Lys Arg Lys Ile Pro
1               5                   10                  15
```

<210> SEQ ID NO 46
<211> LENGTH: 16
<212> TYPE: PRT
<213> ORGANISM: Homo sapiens

<400> SEQUENCE: 46

```
Pro Arg Gly Asn Gly Cys Pro Arg Lys Glu Ile Ile Val Trp Lys Lys
1               5                   10                  15
```

<210> SEQ ID NO 47
<211> LENGTH: 16
<212> TYPE: PRT
<213> ORGANISM: Homo sapiens

<400> SEQUENCE: 47

```
Leu Pro Arg Gly Asn Gly Cys Pro Arg Lys Glu Ile Ile Val Trp Lys
1               5                   10                  15
```

<210> SEQ ID NO 48
<211> LENGTH: 16
<212> TYPE: PRT
<213> ORGANISM: Homo sapiens

<400> SEQUENCE: 48

```
Gln Ile Leu Pro Arg Gly Asn Gly Cys Pro Arg Lys Glu Ile Ile Val
1               5                   10                  15
```

<210> SEQ ID NO 49
<211> LENGTH: 16
<212> TYPE: PRT
<213> ORGANISM: Homo sapiens

<400> SEQUENCE: 49

```
Ile Leu Pro Arg Gly Asn Gly Cys Pro Arg Lys Glu Ile Ile Val Trp
1               5                   10                  15
```

<210> SEQ ID NO 50
<211> LENGTH: 16
<212> TYPE: PRT
<213> ORGANISM: Homo sapiens

```
<400> SEQUENCE: 50

Arg Ile Gln Ile Leu Pro Arg Gly Asn Gly Cys Pro Arg Lys Glu Ile
1               5                   10                  15

<210> SEQ ID NO 51
<211> LENGTH: 16
<212> TYPE: PRT
<213> ORGANISM: Homo sapiens

<400> SEQUENCE: 51

Arg Gly Asn Gly Cys Pro Arg Lys Glu Ile Ile Val Trp Lys Lys Asn
1               5                   10                  15

<210> SEQ ID NO 52
<211> LENGTH: 16
<212> TYPE: PRT
<213> ORGANISM: Homo sapiens

<400> SEQUENCE: 52

Lys Arg Ser Ser Ser Thr Leu Pro Val Pro Val Phe Lys Arg Lys Ile
1               5                   10                  15

<210> SEQ ID NO 53
<211> LENGTH: 16
<212> TYPE: PRT
<213> ORGANISM: Homo sapiens

<400> SEQUENCE: 53

Ile Gln Ile Leu Pro Arg Gly Asn Gly Cys Pro Arg Lys Glu Ile Ile
1               5                   10                  15

<210> SEQ ID NO 54
<211> LENGTH: 16
<212> TYPE: PRT
<213> ORGANISM: Homo sapiens

<400> SEQUENCE: 54

Asp Arg Ile Gln Ile Leu Pro Arg Gly Asn Gly Cys Pro Arg Lys Glu
1               5                   10                  15

<210> SEQ ID NO 55
<211> LENGTH: 16
<212> TYPE: PRT
<213> ORGANISM: Homo sapiens

<400> SEQUENCE: 55

Arg Lys Arg Ser Ser Ser Thr Leu Pro Val Pro Val Phe Lys Arg Lys
1               5                   10                  15

<210> SEQ ID NO 56
<211> LENGTH: 16
<212> TYPE: PRT
<213> ORGANISM: Homo sapiens

<400> SEQUENCE: 56

Arg Cys Arg Cys Val Gln Glu Ser Ser Val Phe Ile Pro Arg Arg Phe
1               5                   10                  15

<210> SEQ ID NO 57
<211> LENGTH: 16
<212> TYPE: PRT
<213> ORGANISM: Homo sapiens

<400> SEQUENCE: 57
```

```
Gly Asn Gly Cys Pro Arg Lys Glu Ile Ile Val Trp Lys Lys Asn Lys
1               5                   10                  15
```

<210> SEQ ID NO 58
<211> LENGTH: 16
<212> TYPE: PRT
<213> ORGANISM: Homo sapiens

<400> SEQUENCE: 58

```
Cys Val Gln Glu Ser Ser Val Phe Ile Pro Arg Arg Phe Ile Asp Arg
1               5                   10                  15
```

<210> SEQ ID NO 59
<211> LENGTH: 16
<212> TYPE: PRT
<213> ORGANISM: Homo sapiens

<400> SEQUENCE: 59

```
Ile Asp Arg Ile Gln Ile Leu Pro Arg Gly Asn Gly Cys Pro Arg Lys
1               5                   10                  15
```

<210> SEQ ID NO 60
<211> LENGTH: 16
<212> TYPE: PRT
<213> ORGANISM: Homo sapiens

<400> SEQUENCE: 60

```
Leu Arg Cys Arg Cys Val Gln Glu Ser Ser Val Phe Ile Pro Arg Arg
1               5                   10                  15
```

<210> SEQ ID NO 61
<211> LENGTH: 16
<212> TYPE: PRT
<213> ORGANISM: Homo sapiens

<400> SEQUENCE: 61

```
Phe Ile Asp Arg Ile Gln Ile Leu Pro Arg Gly Asn Gly Cys Pro Arg
1               5                   10                  15
```

<210> SEQ ID NO 62
<211> LENGTH: 16
<212> TYPE: PRT
<213> ORGANISM: Homo sapiens

<400> SEQUENCE: 62

```
Arg Cys Val Gln Glu Ser Ser Val Phe Ile Pro Arg Arg Phe Ile Asp
1               5                   10                  15
```

<210> SEQ ID NO 63
<211> LENGTH: 16
<212> TYPE: PRT
<213> ORGANISM: Homo sapiens

<400> SEQUENCE: 63

```
Cys Arg Cys Val Gln Glu Ser Ser Val Phe Ile Pro Arg Arg Phe Ile
1               5                   10                  15
```

<210> SEQ ID NO 64
<211> LENGTH: 16
<212> TYPE: PRT
<213> ORGANISM: Homo sapiens

<400> SEQUENCE: 64

```
Gln Glu Ser Ser Val Phe Ile Pro Arg Arg Phe Ile Asp Arg Ile Gln
1               5                   10                  15
```

<210> SEQ ID NO 65
<211> LENGTH: 16
<212> TYPE: PRT
<213> ORGANISM: Homo sapiens

<400> SEQUENCE: 65

Arg Phe Ile Asp Arg Ile Gln Ile Leu Pro Arg Gly Asn Gly Cys Pro
1               5                   10                  15

<210> SEQ ID NO 66
<211> LENGTH: 16
<212> TYPE: PRT
<213> ORGANISM: Homo sapiens

<400> SEQUENCE: 66

Val Gln Glu Ser Ser Val Phe Ile Pro Arg Arg Phe Ile Asp Arg Ile
1               5                   10                  15

<210> SEQ ID NO 67
<211> LENGTH: 16
<212> TYPE: PRT
<213> ORGANISM: Homo sapiens

<400> SEQUENCE: 67

Glu Ser Ser Val Phe Ile Pro Arg Arg Phe Ile Asp Arg Ile Gln Ile
1               5                   10                  15

<210> SEQ ID NO 68
<211> LENGTH: 16
<212> TYPE: PRT
<213> ORGANISM: Homo sapiens

<400> SEQUENCE: 68

Ser Leu Arg Cys Arg Cys Val Gln Glu Ser Ser Val Phe Ile Pro Arg
1               5                   10                  15

<210> SEQ ID NO 69
<211> LENGTH: 16
<212> TYPE: PRT
<213> ORGANISM: Homo sapiens

<400> SEQUENCE: 69

Asn Gly Cys Pro Arg Lys Glu Ile Ile Val Trp Lys Lys Asn Lys Ser
1               5                   10                  15

<210> SEQ ID NO 70
<211> LENGTH: 16
<212> TYPE: PRT
<213> ORGANISM: Homo sapiens

<400> SEQUENCE: 70

Pro Gln Ala Glu Trp Ile Gln Arg Met Met Glu Val Leu Arg Lys Arg
1               5                   10                  15

<210> SEQ ID NO 71
<211> LENGTH: 16
<212> TYPE: PRT
<213> ORGANISM: Homo sapiens

<400> SEQUENCE: 71

Arg Arg Phe Ile Asp Arg Ile Gln Ile Leu Pro Arg Gly Asn Gly Cys
1               5                   10                  15

<210> SEQ ID NO 72
<211> LENGTH: 16

```
<212> TYPE: PRT
<213> ORGANISM: Homo sapiens

<400> SEQUENCE: 72

Leu Arg Lys Arg Ser Ser Ser Thr Leu Pro Val Pro Val Phe Lys Arg
1               5                   10                  15

<210> SEQ ID NO 73
<211> LENGTH: 11
<212> TYPE: PRT
<213> ORGANISM: Homo sapiens

<400> SEQUENCE: 73

Val Gln Glu Ser Ser Val Phe Ile Pro Arg Arg
1               5                   10

<210> SEQ ID NO 74
<211> LENGTH: 26
<212> TYPE: PRT
<213> ORGANISM: Homo sapiens

<400> SEQUENCE: 74

Glu Trp Ile Gln Arg Met Met Glu Val Leu Arg Lys Arg Ser Ser Ser
1               5                   10                  15

Thr Leu Pro Val Pro Val Phe Lys Arg Lys
            20                  25

<210> SEQ ID NO 75
<211> LENGTH: 4
<212> TYPE: PRT
<213> ORGANISM: Homo sapiens

<400> SEQUENCE: 75

Lys Lys Asn Lys
1

<210> SEQ ID NO 76
<211> LENGTH: 6
<212> TYPE: PRT
<213> ORGANISM: Homo sapiens

<400> SEQUENCE: 76

Arg Lys Arg Ser Ser Ser
1               5

<210> SEQ ID NO 77
<211> LENGTH: 6
<212> TYPE: PRT
<213> ORGANISM: Homo sapiens

<400> SEQUENCE: 77

Arg Gly Asn Gly Cys Pro
1               5

<210> SEQ ID NO 78
<211> LENGTH: 21
<212> TYPE: PRT
<213> ORGANISM: Homo sapiens

<400> SEQUENCE: 78

Val Tyr Tyr Thr Ser Leu Arg Cys Arg Cys Val Gln Glu Ser Ser Val
1               5                   10                  15

Phe Ile Pro Arg Arg
            20
```

```
<210> SEQ ID NO 79
<211> LENGTH: 7
<212> TYPE: PRT
<213> ORGANISM: Homo sapiens

<400> SEQUENCE: 79

Asp Arg Ile Gln Ile Leu Pro
1               5

<210> SEQ ID NO 80
<211> LENGTH: 7
<212> TYPE: PRT
<213> ORGANISM: Homo sapiens

<400> SEQUENCE: 80

Arg Lys Glu Ile Ile Val Trp
1               5

<210> SEQ ID NO 81
<211> LENGTH: 9
<212> TYPE: PRT
<213> ORGANISM: Homo sapiens

<400> SEQUENCE: 81

Lys Ser Ile Val Cys Val Asp Pro Gln
1               5

<210> SEQ ID NO 82
<211> LENGTH: 13
<212> TYPE: PRT
<213> ORGANISM: Homo sapiens

<400> SEQUENCE: 82

Thr Ser Leu Val Glu Asn His Leu Cys Pro Ala Thr Glu
1               5                   10

<210> SEQ ID NO 83
<211> LENGTH: 15
<212> TYPE: PRT
<213> ORGANISM: Homo sapiens

<400> SEQUENCE: 83

Glu Gly Ser Val Gly Trp Val Leu Gly Thr Phe Leu Cys Lys Thr
1               5                   10                  15

<210> SEQ ID NO 84
<211> LENGTH: 7
<212> TYPE: PRT
<213> ORGANISM: Homo sapiens

<400> SEQUENCE: 84

Leu Pro Arg Cys Thr Phe Ser
1               5

<210> SEQ ID NO 85
<211> LENGTH: 10
<212> TYPE: PRT
<213> ORGANISM: Homo sapiens

<400> SEQUENCE: 85

Leu Ala Arg Leu Lys Ala Val Asp Asn Thr
1               5                   10

<210> SEQ ID NO 86
<211> LENGTH: 10
```

```
<212> TYPE: PRT
<213> ORGANISM: Homo sapiens

<400> SEQUENCE: 86

Met Ala Ser Phe Lys Ala Val Phe Val Pro
1               5                   10

<210> SEQ ID NO 87
<211> LENGTH: 16
<212> TYPE: PRT
<213> ORGANISM: Homo sapiens

<400> SEQUENCE: 87

Ala Ala Gly Pro Glu Ala Gly Glu Asn Gln Lys Gln Pro Glu Lys Asn
1               5                   10                  15

<210> SEQ ID NO 88
<211> LENGTH: 16
<212> TYPE: PRT
<213> ORGANISM: Homo sapiens

<400> SEQUENCE: 88

Ser Gln Ala Ser Glu Gly Ala Ser Ser Asp Ile His Thr Pro Ala Gln
1               5                   10                  15

<210> SEQ ID NO 89
<211> LENGTH: 16
<212> TYPE: PRT
<213> ORGANISM: Homo sapiens

<400> SEQUENCE: 89

Ser Thr Leu Gln Ser Thr Gln Arg Pro Thr Leu Pro Val Gly Ser Leu
1               5                   10                  15

<210> SEQ ID NO 90
<211> LENGTH: 16
<212> TYPE: PRT
<213> ORGANISM: Homo sapiens

<400> SEQUENCE: 90

Ser Trp Ser Val Cys Gly Gly Asn Lys Asp Pro Trp Val Gln Glu Leu
1               5                   10                  15

<210> SEQ ID NO 91
<211> LENGTH: 16
<212> TYPE: PRT
<213> ORGANISM: Homo sapiens

<400> SEQUENCE: 91

Gly Pro Thr Ala Arg Thr Ser Ala Thr Val Pro Val Leu Cys Leu Leu
1               5                   10                  15

<210> SEQ ID NO 92
<211> LENGTH: 16
<212> TYPE: PRT
<213> ORGANISM: Homo sapiens

<400> SEQUENCE: 92

Ser Gly Ile Val Ala His Gln Lys His Leu Leu Pro Thr Ser Pro Pro
1               5                   10                  15

<210> SEQ ID NO 93
<211> LENGTH: 6
<212> TYPE: PRT
<213> ORGANISM: Homo sapiens
```

```
<400> SEQUENCE: 93

Arg Leu Arg Lys His Leu
1               5

<210> SEQ ID NO 94
<211> LENGTH: 7
<212> TYPE: PRT
<213> ORGANISM: Homo sapiens

<400> SEQUENCE: 94

Leu Gln Ser Thr Gln Arg Pro
1               5

<210> SEQ ID NO 95
<211> LENGTH: 13
<212> TYPE: PRT
<213> ORGANISM: Homo sapiens

<400> SEQUENCE: 95

Ser Ser Asp Lys Glu Leu Thr Arg Pro Asn Glu Thr Thr
1               5                   10

<210> SEQ ID NO 96
<211> LENGTH: 12
<212> TYPE: PRT
<213> ORGANISM: Homo sapiens

<400> SEQUENCE: 96

Ala Gly Glu Asn Gln Lys Gln Pro Glu Lys Asn Ala
1               5                   10

<210> SEQ ID NO 97
<211> LENGTH: 6
<212> TYPE: PRT
<213> ORGANISM: Homo sapiens

<400> SEQUENCE: 97

Asn Glu Gly Ser Val Thr
1               5

<210> SEQ ID NO 98
<211> LENGTH: 9
<212> TYPE: PRT
<213> ORGANISM: Homo sapiens

<400> SEQUENCE: 98

Ile Ser Ser Asp Ser Pro Pro Ser Val
1               5

<210> SEQ ID NO 99
<211> LENGTH: 8
<212> TYPE: PRT
<213> ORGANISM: Homo sapiens

<400> SEQUENCE: 99

Cys Gly Gly Asn Lys Asp Pro Trp
1               5

<210> SEQ ID NO 100
<211> LENGTH: 21
<212> TYPE: PRT
<213> ORGANISM: Homo sapiens

<400> SEQUENCE: 100

Leu Leu Pro Thr Ser Pro Pro Ile Ser Gln Ala Ser Glu Gly Ala Ser
```

Ser Asp Ile His Thr
            20

<210> SEQ ID NO 101
<211> LENGTH: 28
<212> TYPE: PRT
<213> ORGANISM: Homo sapiens

<400> SEQUENCE: 101

Ser Thr Gln Arg Pro Thr Leu Pro Val Gly Ser Leu Ser Ser Asp Lys
1               5                   10                  15

Glu Leu Thr Arg Pro Asn Glu Thr Thr Ile His Thr
            20                  25

<210> SEQ ID NO 102
<211> LENGTH: 27
<212> TYPE: PRT
<213> ORGANISM: Homo sapiens

<400> SEQUENCE: 102

Ser Leu Ala Ala Gly Pro Glu Ala Gly Glu Asn Gln Lys Gln Pro Glu
1               5                   10                  15

Lys Asn Ala Gly Pro Thr Ala Arg Thr Ser Ala
            20                  25

<210> SEQ ID NO 103
<211> LENGTH: 9
<212> TYPE: PRT
<213> ORGANISM: Homo sapiens

<400> SEQUENCE: 103

Thr Gly Ser Cys Tyr Cys Gly Lys Arg
1               5

<210> SEQ ID NO 104
<211> LENGTH: 7
<212> TYPE: PRT
<213> ORGANISM: Homo sapiens

<400> SEQUENCE: 104

Asp Ser Pro Pro Ser Val Gln
1               5

<210> SEQ ID NO 105
<211> LENGTH: 26
<212> TYPE: PRT
<213> ORGANISM: Homo sapiens

<400> SEQUENCE: 105

Arg Lys His Leu Arg Ala Tyr His Arg Cys Leu Tyr Tyr Thr Arg Phe
1               5                   10                  15

Gln Leu Leu Ser Trp Ser Val Cys Gly Gly
            20                  25

<210> SEQ ID NO 106
<211> LENGTH: 37
<212> TYPE: PRT
<213> ORGANISM: Homo sapiens

<400> SEQUENCE: 106

Trp Val Gln Glu Leu Met Ser Cys Leu Asp Leu Lys Glu Cys Gly His
1               5                   10                  15

Ala Tyr Ser Gly Ile Val Ala His Gln Lys His Leu Leu Pro Thr Ser
            20                  25                  30

Pro Pro Ile Ser Gln
            35

<210> SEQ ID NO 107
<211> LENGTH: 15
<212> TYPE: PRT
<213> ORGANISM: Homo sapiens

<400> SEQUENCE: 107

Ser Asp Ile His Thr Pro Ala Gln Met Leu Leu Ser Thr Leu Gln
1               5                   10                  15

<210> SEQ ID NO 108
<211> LENGTH: 9
<212> TYPE: PRT
<213> ORGANISM: Homo sapiens

<400> SEQUENCE: 108

Arg Pro Thr Leu Pro Val Gly Ser Leu
1               5

<210> SEQ ID NO 109
<211> LENGTH: 9
<212> TYPE: PRT
<213> ORGANISM: Homo sapiens

<400> SEQUENCE: 109

Thr Ala Gly His Ser Leu Ala Ala Gly
1               5

<210> SEQ ID NO 110
<211> LENGTH: 13
<212> TYPE: PRT
<213> ORGANISM: Homo sapiens

<400> SEQUENCE: 110

Gly Lys Arg Ile Ser Ser Asp Ser Pro Pro Ser Val Gln
1               5                   10

<210> SEQ ID NO 111
<211> LENGTH: 30
<212> TYPE: PRT
<213> ORGANISM: Homo sapiens

<400> SEQUENCE: 111

Lys Asp Pro Trp Val Gln Glu Leu Met Ser Cys Leu Asp Leu Lys Glu
1               5                   10                  15

Cys Gly His Ala Tyr Ser Gly Ile Val Ala His Gln Lys His
            20                  25                  30

<210> SEQ ID NO 112
<211> LENGTH: 10
<212> TYPE: PRT
<213> ORGANISM: Homo sapiens

<400> SEQUENCE: 112

His Gln Asp Phe Leu Gln Phe Ser Lys Val
1               5                   10

<210> SEQ ID NO 113
<211> LENGTH: 14
<212> TYPE: PRT
<213> ORGANISM: Homo sapiens

```
<400> SEQUENCE: 113

Ala Gly Ile His Glu Trp Val Phe Gly Gln Val Met Cys Lys
1               5                   10

<210> SEQ ID NO 114
<211> LENGTH: 23
<212> TYPE: PRT
<213> ORGANISM: Homo sapiens

<400> SEQUENCE: 114

Pro Gln Ile Ile Tyr Gly Asn Val Phe Asn Leu Asp Lys Leu Ile Cys
1               5                   10                  15

Gly Tyr His Asp Glu Ala Ile
            20

<210> SEQ ID NO 115
<211> LENGTH: 16
<212> TYPE: PRT
<213> ORGANISM: Homo sapiens

<400> SEQUENCE: 115

Tyr Tyr Ala Met Thr Ser Phe His Tyr Thr Ile Met Val Thr Glu Ala
1               5                   10                  15
```

ANTI-CXCL13 AND ANTI-CXCR5 ANTIBODIES FOR THE PREVENTION AND TREATMENT OF CANCER AND CANCER CELL MIGRATION This application is a Continuation-In-Part of U.S. patent application Ser. No. 13/233,769, filed on Sep. 15, 2011, which is a Continuation-In-Part of U.S. patent application Ser. No. 12/967,273, filed Dec. 14, 2010, which is a continuation of U.S. patent application Ser. No. 10/712,398, filed on Nov. 14, 2003, now U.S. Pat. No. 7,919,083, which claims priority of U.S. Provisional Patent Application No. 60/426,347, filed Nov. 15, 2002. The entirety of all of the aforementioned applications is incorporated herein by reference.

FIELD

This application generally relates to the prevention and treatment of cancer. In particular, the invention relates to the use of anti-chemokine and/or anti-chemokine receptor antibodies for the inhibition or prevention of the growth and/or migration of cancer cells.

BACKGROUND

Despite recent advances in cancer research, the development of cell-specific therapies for the treatment of malignancies remain elusive. The many and complex factors that enable malignant cells to undergo mutations, evade immune protection and promote angiogenesis to deliver nutrients to the rapidly growing cells complicate the development of targeted treatment modalities. Current therapies have multiple untoward side effects. For example, chemotherapy results in multiple painful and sometimes lethal side effects. Advances in biotechnology have promoted the development of targeted biologicals with fewer side effects.

Host cells have surface receptors that associate with ligands to signal and cause host cell activities. The epidermal growth factor receptor helps control cell growth and metastasis. Many tumor cells express higher numbers of epidermal growth factor receptors than normal cells. A new treatment designated IMC-225 was specifically designed to target and block epidermal growth factor receptors, thus preventing cell division and repair. Recently, trastuzumab, which is a HER-2-specific monoclonal antibody, has proven effective at treating metastatic breast cancers. This antibody blocks interactions on cancer cells that inhibit cell growth. HER-2, however, is only found on about 25 to 30 percent of breast cancer cells.

Chemokines are a superfamily of small, cytokine-like proteins that are resistant to hydrolysis, promote neovascularization or endothelial cell growth inhibition, induce cytoskeletal rearrangement, activate or inactivate lymphocytes, and mediate chemotaxis through interactions with G-protein coupled receptors. Chemokines can mediate the growth and migration of host cells that express their receptors.

CXCL13 is a small cytokine belonging to the CXC chemokine family. As its name suggests, this chemokine is selectively chemotactic for B cells belonging to both the B-1 and B-2 subsets, and elicits its effects by interacting with chemokine receptor CXCR5. CXCL13 and CXCR5 control the organization of B cells within follicles of lymphoid tissues. CXCR5 is expressed highly in the liver, spleen, lymph nodes, and gut of humans. CXCR5 plays an essential role in B cell migration.

In T-lymphocytes, CXCL13 expression may reflect a germinal center origin of the T-cell. Hence, expression of CXCL13 in T-cell lymphomas, such as Angioimmunoblastic T-cell Lymphoma, is thought to reflect a germinal center origin of the neoplastic T-cells.

SUMMARY

One aspect of the present invention relates to a method for treating melanoma, sarcoma, blastoma, carcinoma, lymphoma, myeloma or leukemia in a subject. In one embodiment, the method comprises the step of administering to the subject a therapeutically effective amount of an anti-CXCL13 antibody, or an anti-CXCR5 antibody, or a combination thereof. In another embodiment, the method comprises the step of immunizing the subject with an effective amount of CXCL13 and/or CXCR5 immunogen(s) as protein, peptide or encoded gene to induce antibodies that inhibit the biological activity of CXCL13 and/or CXCR5. In another embodiment, the method comprises the step of administering to the subject an expression vector that expresses an anti-CXCL13 antibody, or an anti-CXCR5 antibody, or a combination thereof in said subject. In another embodiment, the method comprises the step of administering to the subject an effective amount of an expression vector that expresses an agent capable of (1) inhibiting the expression of CXCL13 and/or CXCR5, (2) inhibiting the interaction between CXCL13 and CXCR5, or (3) inhibiting a biological activity of CXCL13 and/or CXCR5.

Another aspect of the present invention relates to a method for prevention or inhibition of the migration or metastasis of cancer cells with elevated expression of CXCL13 and/or CXCR5 in a subject. In one embodiment, the method comprises the step of administering to the subject a therapeutically effective amount of an anti-CXCL13 antibody, an anti-CXCR5 antibody, or a combination thereof. In another embodiment, the method comprises the step of immunizing the subject with an effective amount of CXCL13 and/or CXCR5 immunogen(s) as protein, peptide or encoded gene to induce antibodies that inhibit the biological activity of CXCL13 and/or CXCR5. In another embodiment, the method comprises the step of administering to the subject an expression vector that expresses an anti-CXCL13 antibody, or an anti-CXCR5 antibody, or a combination thereof in said subject. In another embodiment, the method comprises the step of administering to the subject an effective amount of an expression vector that expresses an agent capable of (1) inhibiting the expression of CXCL13 and/or CXCR5, (2) inhibiting the interaction between CXCL13 and CXCR5, or (3) inhibiting a biological activity of CXCL13 and/or CXCR5.

Another aspect of the present invention relates to a method for treating cancer in a subject. The method comprises the steps of detecting a level of CXCL13 expression and/or CXCR5 expression in a biological sample from said subject and, if an elevated level of CXCL13 expression and/or CXCR5 expression is detected in said biological sample, administering to the subject (1) a therapeutically effective amount of an antibody to CXCL13 and/or an antibody to CXCR5 or (2) an expression vector that expresses an anti-CXCL13 antibody, or an anti-CXCR5 antibody, or a combination thereof in said subject. In another embodiment, the method comprises the steps of detecting a level of CXCL13 expression and/or CXCR5 expression in a biological sample from said subject and, if an elevated level of CXCL13 and/or CXCR3 expression is detected in said biological sample, immunizing the subject with an effective amount of CXCL13 and/or CXCR5 immunogen to elicit an antibody response to inhibit the biological activity of CXCL13 and/or CXCR5. In another embodiment, the method comprises the step of detecting a level of CXCL13 expression and/or CXCR5 expression in a biological sample from said subject and, if an elevated level of CXCL13 expression and/or CXCR5 expression is detected in said biological sample, administering to the subject an effective amount of an expression vector that expresses an agent capable of (1) inhibiting the expression of CXCL13 and/or CXCR5, or (2) inhibiting the interaction between CXCL13 and CXCR5, or (3) inhibiting a biological activity of CXCL13 and/or CXCR5.

Another aspect of the present invention relates to a method for enhancing the effect of chemotherapy. The method comprises administering to a subject who is under chemotherapy for a cancer, an effective amount of an anti-CXCL13 antibody, or an anti-CXCR5 antibody, or a combination thereof. In another embodiment, the method comprises the step of immunizing the subject+who is under chemotherapy for a cancer with an effective amount of CXCL13 and/or CXCR5 immunogen(s) as protein, peptide or encoded gene to induce antibodies that inhibit the biological activity of CXCL13 and/or CXCR5. In another embodiment, the method comprises the step of administering to the subject who is under chemotherapy for a cancer an expression vector that expresses an anti-CXCL13 antibody, or an anti-CXCR5 antibody, or a combination thereof. In another embodiment, the method comprises the step of administering to the subject an effective amount of an expression vector that expresses an agent capable of (1) inhibiting the expression of CXCL13 and/or CXCR5, or (2) inhibiting the interaction between CXCL13 and CXCR5, or (3) inhibiting a biological activity of CXCL13 and/or CXCR5

Another aspect of the present invention relates to a method for treating cancer in a subject by immunizing the subject with an effective amount of one or more of CXCL13 and CXCR5 immunogens and an effective amount of one or more of CXCL16 and CXCR6 immunogens, wherein said cancer is melanoma, lymphoma, leukemia, sarcoma, blastoma, or carcinoma.

Another aspect of the present invention relates to a method for treating cancer in a subject by immunizing the subject with an effective amount of a CXCL16 immunogen and/or a CXCR6 immunogen to induce antibodies that inhibit the biological activity of CXCL16 and/or CXCR6, wherein the cancer is melanoma, lymphoma, leukemia, sarcoma, blastoma, or carcinoma, wherein the CXCL16 immunogen is a peptide comprising one or more sequences selected from the group consisting of AAGPEAGENQKQPEKN (SEQ ID NO:87), SQASEGASSDIHTPAQ (SEQ ID NO:88), STLQSTQRPTLPVGSL (SEQ ID NO:89), SWSVCGGNKDPWVQEL (SEQ ID NO:90), GPTARTSATVPVLCLL (SEQ ID NO:91), SGIVAHQKHLLPTSPP (SEQ ID NO:92), RLRKHL (SEQ ID NO:93), LQSTQRP (SEQ ID NO:94), SSDKELTRPNETT (SEQ ID NO:95), AGENQKQPEKNA (SEQ ID NO:96), NEGSVT (SEQ ID NO:97), ISSDSPPSV (SEQ ID NO:98), CGGNKDPW (SEQ ID NO:99), LLPTSPPISQASEGASSDIHT (SEQ ID NO:100), STQRPTLPVGSLSSDKELTRPNETTIHT (SEQ ID NO:101), SLAAGPEAGENQKQPEKNAGPTARTSA (SEQ ID NO:102), TGSCYCGKR (SEQ ID NO:103), DSPPSVQ (SEQ ID NO:104), RKHLRAYHRCLYYTRFQLLSWSVCGG (SEQ ID NO:105), WVQELMSCLDLKECGHAYSGIVAHQKHLLPTSPPISQ (SEQ ID NO:106), SDIHTPAQMLLSTLQ (SEQ ID NO:107), RPTLPVGSL (SEQ ID NO:108), TAGHSLAAG (SEQ ID NO:109), GKRISSDSPPSVQ (SEQ ID NO:110) and KDPWVQELMSCLDLKECGHAYSGIVAHQKH (SEQ ID NO:111), and wherein the CXCR6 immunogen is a peptide comprising one or more sequences selected from the group consisting of HQDFLQF-SKV (SEQ ID NO:112), AGIHEWVFGQVMCK (SEQ ID NO:113), PQIIYGNVFNLDKLICGYHDEAI (SEQ ID NO:114) and YYAMTSFHYTIMVTEA (SEQ ID NO:115).

DETAILED DESCRIPTION

Figure 1:
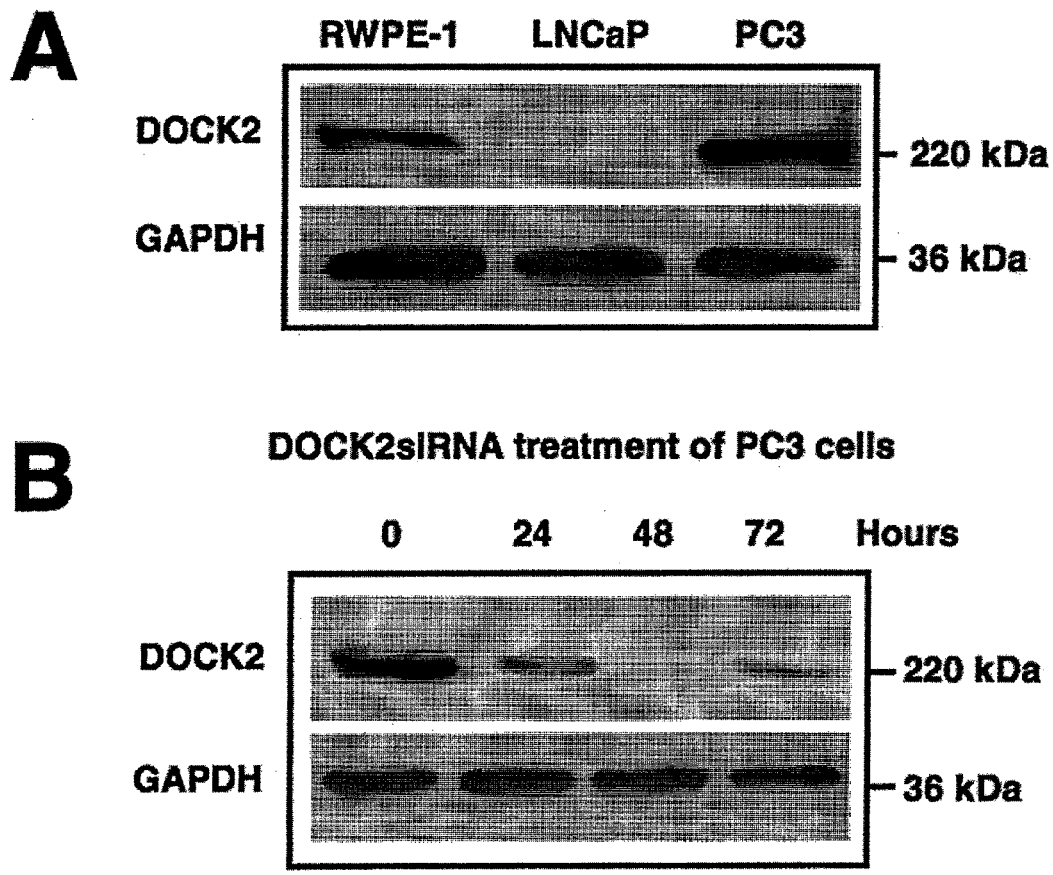
FIGS. 1A-B show expression of DOCK2 by prostate cancer (PCa) cell lines.

The following detailed description is presented to enable any person skilled in the art to make and use the invention. For purposes of explanation, specific nomenclature is set forth to provide a thorough understanding of the present invention. However, it will be apparent to one skilled in the art that these specific details are not required to practice the invention. Descriptions of specific applications are provided only as representative examples. The present invention is not intended to be limited to the embodiments shown, but is to be accorded the widest possible scope consistent with the principles and features disclosed herein.

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular.

Definitions

As used herein, the following terms shall have the following meanings:

The terms "treat," "treating" or "treatment" as used herein, refers to a method of alleviating or abrogating a disorder and/or its attendant symptoms. The terms "prevent", "preventing" or "prevention," as used herein, refer to a method of barring a subject from acquiring a disorder and/or its attendant symptoms. In certain embodiments, the terms "prevent," "preventing" or "prevention" refer to a method of reducing the risk of acquiring a disorder and/or its attendant symptoms.

As used herein, the term "antibody" refers to immunoglobulin molecules and immunologically active portions of immunoglobulin (Ig) molecules, i.e., molecules that contain an antigen binding site that specifically binds (immunoreacts with) an antigen. The term "antibody" is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity. By "specifically bind" or "immunoreacts with" is meant that the antibody reacts with one or more antigenic determinants of the desired antigen and does not react (i.e., bind) with other polypeptides or binds at much lower affinity with other polypeptides. The term "antibody" also includes antibody fragments that comprise a portion of a full length antibody, generally the antigen binding or variable region thereof. Examples of antibody fragments include Fab, Fab', F(ab')2, and Fv fragments; diabodies; linear antibodies; single-chain antibody (scFv) molecules; and multispecific antibodies formed from antibody fragments. In certain embodiments of the invention, it may be desirable to use an antibody fragment, rather than an intact antibody, to increase tumor penetration, for example. In this case, it may be desirable to use an antibody fragment that has been modified by any means known in the art in order to increase its serum half life.

The term "monoclonal antibody" as used herein refers to an antibody obtained from a population of substantially homogeneous antibodies, i.e., the individual antibodies comprising the population are identical except for possible naturally occurring mutations that may be present in minor amounts. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. Natl. Acad. Sci. USA* 81:6851-6855 (1984)).

"Humanized" forms of non-human antibodies are chimeric antibodies which contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and/or capacity. Methods for making humanized and other chimeric antibodies are known in the art.

"Bispecific antibodies" are antibodies that have binding specificities for at least two different antigens. In the present case, one of the binding specificities is for CXCL16 or CXCR6. The second binding target is any other antigen, and advantageously is a cell-surface protein or receptor or receptor subunit. Methods for making bispecific antibodies are known in the art.

The use of "heteroconjugate antibodies" is also within the scope of the present invention. Heteroconjugate antibodies are composed of two covalently joined antibodies. Such antibodies have, for example, been proposed to target immune system cells to unwanted cells (U.S. Pat. No. 4,676,980). It is contemplated that the antibodies can be prepared in vitro using known methods in synthetic protein chemistry, including those involving crosslinking agents.

The present invention also contemplates the use of "immunoconjugates" comprising an antibody conjugated to a cytotoxic agent such as a toxin (e.g., an enzymatically active toxin of bacterial, fungal, plant, or animal origin, or fragments thereof), or a radioactive isotope (i.e., a radioconjugate). Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin, and the tricothecenes. A variety of radionuclides are available for the production of radioconjugated antibodies. Examples include 212Bi, 131I, 131In, 90Y, and 186Re.

In a pharmacological sense, in the context of the present invention, a "therapeutically effective amount" of an antibody refers to an amount effective in the prevention or treatment of a disorder for the treatment of which the antibody is effective. A "disorder" is any condition that would benefit from treatment with the antibody, including carcinoma and chemoresistance. This includes chronic and acute disorders or diseases including those pathological conditions which predispose the mammal to the disorder in question.

The term "tumor" as used herein refers to a neoplasm or a solid lesion formed by an abnormal growth of cells. A tumor can be benign, pre-malignant or malignant.

The term "cancer" is defined as a malignant neoplasm or malignant tumor and is a class of diseases in which a group of cells display uncontrolled growth, invasion that intrudes upon and destroys adjacent tissues, and sometimes metastasis, or spreading to other locations in the body via lymph or blood. These three malignant properties of cancers differentiate them from benign tumors, which do not invade or metastasize. Exemplary cancers include: carcinoma, melanoma, sarcoma, lymphoma, leukemia, germ cell tumor, and blastoma.

The term "carcinoma" as used herein refers to an invasive malignant tumor consisting of transformed epithelial cells or transformed cells of unknown histogenesis, but which possess specific molecular or histological characteristics that are associated with epithelial cells, such as the production of cytokeratins or intercellular bridges. Exemplary carcinomas of the present invention include ovarian cancer, vaginal cancer, cervical cancer, uterine cancer, prostate cancer, anal cancer, rectal cancer, colon cancer, stomach cancer, pancreatic cancer, insulinoma, adenocarcinoma, adenosquamous carcinoma, neuroendocrine tumor, breast cancer, lung cancer, esophageal cancer, oral cancer, brain cancer, medulloblastoma, neuroectodermal tumor, glioma, pituitary cancer, and bone cancer.

The term "lymphoma" as used herein is a cancer of lymphatic cells of the immune system. Lymphomas typically present as a solid tumor. Exemplary lymphomas include: small lymphocytic lymphoma, lymphoplasmacytic lymphoma, Waldenström macroglobulinemia, splenic marginal zone lymphoma, plasmacytoma, extranodal marginal zone B cell lymphoma, MALT lymphoma, nodal marginal zone B cell lymphoma (NMZL), follicular lymphoma, mantle cell lymphoma, diffuse large B cell lymphoma, mediastinal (thymic) large B cell lymphoma, intravascular large B cell lymphoma, primary effusion lymphoma, Burkitt lymphoma, B cell chronic lymphocytic lymphoma, classical Hodgkin lymphoma, nodular lymphocyte-predominant Hodgkin lymphoma, adult T cell lymphoma, nasal type extranodal NK/T cell lymphoma, enteropathy-type T cell lymphoma, hepatosplenic T cell lymphoma, blastic NK cell lymphoma, mycosis fungoide, Sezary syndrome, primary cutaneous CD30-positive T cell lympho-proliferative disorders, primary cutaneous anaplastic large cell lymphoma, lymphomatoid papulosis, angioimmunoblastic T cell lymphoma, unspecified peripheral T cell lymphoma, and anaplastic large cell lymphoma. Exemplary forms of classical Hodgkin lymphoma including: nodular sclerosis, mixed cellularity, lymphocyte-rich, and lymphocyte-depleted or not depleted The term "sarcoma" as used herein is a cancer that arises from transformed cells in one of a number of tissues that develop from embryonic mesoderm. Thus, sarcomas include tumors of bone, cartilage, fat, muscle, vascular, and hematopoietic tissues. For example, osteosarcoma arises from bone, chondrosarcoma arises from cartilage, liposarcoma arises from fat, and leiomyosarcoma arises from smooth muscle. Exemplary sarcomas include: Askin's tumor, botryodies, chondrosarcoma, Ewing's-PNET, malignant Hemangioendothelioma, malignant Schwannoma, osteosarcoma, soft tissue sarcomas. Subclases of soft tissue sarcomas include: alveolar soft part sarcoma, angiosarcoma, cystosarcoma phyllodes, dermatofibrosarcomadesmoid tumor, desmoplastic small round cell tumor, epithelioid sarcomaextraskeletal chondrosarcoma, extraskeletal osteosarcoma, fibrosarcoma, hemangiopericytoma, hemangiosarcoma, Kaposi's sarcoma, leiomyosarcoma, liposarcoma, lymphangiosarcomal, lymphosarcoma, malignant fibrous histiocytoma, neurofibrosarcoma, rhabdomyosarcoma, and synovial sarcoma.

The term "leukemia" as used herein is a cancer of the blood or bone marrow characterized by an abnormal increase of white blood cells. Leukemia is a broad term covering a spectrum of diseases. In turn, it is part of the even broader group of diseases called hematological neoplasms. Leukemia is subdivided into a variety of large groups; the first division is between acute and chronic forms of leukemia. Acute leukemia is characterized by a rapid increase in the numbers of immature blood cells. Crowding due to such cells makes the bone marrow unable to produce healthy blood cells. Chronic leukemia is characterized by the excessive build up of relatively mature, but still abnormal, white blood cells. Typically taking months or years to progress, the cells are produced at a much higher rate than normal cells, resulting in many abnormal white blood cells in the blood. Leukemia is also subdivided by the blood cells affected. This split divides leukemias into lymphoblastic or lymphocytic leukemias and myeloid or myelogenous leukemias. In lymphoblastic or lymphocytic leukemias, the cancerous change takes place in a type of marrow cell that normally goes on to form lymphocytes. In myeloid or myelogenous leukemias, the cancerous change takes place in a type of marrow cell that normally goes on to form red blood cells, some other types of white cells, and platelets. Combining these two classifications provides a total of four main categories. Within each of these four main categories, there are typically several subcategories. There are also rare types outside of this classification scheme. Exemplary leukemias include: acute lymphoblastic leukemia (ALL), chronic lymphocytic leukemia (CLL), acute myelogenous leukemia (AML), chronic myelogenous leukemia (CML), hairy cell leukemia (HCL), T-cell prolymphocytic leukemia, large granular lymphocytic leukemia, juvenile myelomonocytic leukemia, B-cell prolymphocytic leukemia, Burkitt leukemia, and adult T-cell leukemia.

The term "melanoma" as used herein is a cancer or malignant tumor of melanocytes. Melanocytes are cells that produce the dark pigment, melanin, which is responsible for the color of skin. They predominantly occur in skin, but are also found in other parts of the body, including the bowel and the eye. Melanoma is divided into the following stereotypes and subtypes: lentigo maligna, lentigo maligna melanoma, superficial spreading melanoma, acral lentiginous melanoma, mucosal melanoma, nodular melanoma, polypoid melanoma, desmoplastic melanoma, amelanotic melanoma, soft-tissue melanoma, melanoma with small nevus-like cells, melanoma with features of a Spitz nevus, and uveal melanoma.

The term "germ cell tumor (GCT)" as used herein is a neoplasm derived from germ cells. Germ cell tumors can be cancerous or non-cancerous tumors. Germ cells normally occur inside the gonads (ovary and testis). Germ cell tumors that originate outside the gonads may be birth defects resulting from errors during development of the embryo. Germ cell tumors are broadly divided in two classes: germinomatous or seminomatous and nongerminomatous or nonseminomatous germ cell tumors. Exemplary germinomatous or seminomatous germ cell tumors include: germinoma, dysgerminoma, and seminoma. Exemplary nongerminomatous or nonseminomatous germ cell tumors include: Embryonal carcinoma, endodermal sinus tumor or yolk sac tumor (EST, YST), choriocarcinoma, mature teratoma, dermoid cyst, immature teratoma, teratoma with malignant transformation, polyembryoma, gonadoblastoma, and mixed GCT.

The term "metastasis" as used herein refers to the spread of a cancer or carcinoma from one organ or part to another non-adjacent organ or part.

"Mammal" for purposes of treatment refers to any animal classified as a mammal, including humans, non-human primates, domestic and farm animals, and zoo, sports, or pet animals, such as dogs, horses, cats, cows, etc. Preferably, the mammal is human.

The term "inhibits" is a relative tem, an agent inhibits a response or condition if the response or condition is quantitatively diminished following administration of the agent, or if it is diminished following administration of the agent, as compared to a reference agent. Similarly, the term "prevents" does not necessarily mean that an agent completely eliminates the response or condition, so long as at least one characteristic of the response or condition is eliminated. Thus, a composition that reduces or prevents an infection or a response, such as a pathological response, can, but does not necessarily completely eliminate such an infection or response, so long as the infection or response is measurably diminished, for example, by at least about 50%, such as by at least about 70%, or about 80%, or even by about 90% of (that is to 10% or less than) the infection or response in the absence of the agent, or in comparison to a reference agent.

The term "increased level" refers to a level that is higher than a normal or control level customarily defined or used in the relevant art. For example, an increased level of immunostaining in a tissue is a level of immunostaining that would be considered higher than the level of immunostaining in a control tissue by a person of ordinary skill in the art.

The term "CXCL13 immunogen" and "CXCR5 immunogen" refers to an immunogenic composition comprising (1) an immunogenic peptide derived from CXCL13 or CXCR5 and/or (2) an expression vector that encodes, and is capable of expressing, an immunogenic peptide derived from CXCL13 or CXCR5. The immunogenic peptide derived from CXCL13 or CXCR5 may be fused to another moiety to enhance its immunogenicity. Examples of the CXCL13 immunogenic peptides include, but are not limited to, peptides consisting of, or comprising, one or more sequences selected from the group consisting of RSSSTLPVPVFKRKIP (SEQ ID NO:45), PRGNGCPRKEIIVWKK (SEQ ID NO:46), LPRGNGCPRKEIIVWK (SEQ ID NO:47), QILPRGNGCPRKEIIV (SEQ ID NO:48), ILPRGNGCPRKEIIVW (SEQ ID NO:49), RIQILPRGNGCPRKEI (SEQ ID NO:50), RGNGCPRKEIIVWKKN (SEQ ID NO:51), KRSSSTLPVPVFKRKI (SEQ ID NO:52), IQILPRGNGCPRKEII (SEQ ID NO:53), DRIQILPRGNGCPRKE (SEQ ID NO:54), RKRSSSTLPVPVFKRK (SEQ ID NO:55), RCRCVQESSVFIPRRF (SEQ ID NO:56), GNGCPRKEIIVWKKNK (SEQ ID NO:57), CVQESSVFIPRRFIDR (SEQ ID NO:58), IDRIQILPRGNGCPRK (SEQ ID NO:59), LRCRCVQESSVFIPRR (SEQ ID NO:60), FIDRIQILPRGNGCPR (SEQ ID NO:61), RCVQESSVFIPRRFID (SEQ ID NO:62), CRCVQESSVFIPRRFI (SEQ ID NO:63), QESSVFIPRRFIDRIQ (SEQ ID NO:64), RFIDRIQILPRGNGCP (SEQ ID NO:65), VQESSVFIPRRFIDRI (SEQ ID NO:66), ESSVFIPRRFIDRIQI (SEQ ID NO:67), SLRCRCVQESSVFIPR (SEQ ID NO:68), NGCPRKEIIVWKKNKS (SEQ ID NO:69), PQAEWIQRMMEVLRKR (SEQ ID NO:70), RRFIDRIQILPRGNGC (SEQ ID NO:71), LRKRSSSTLPVPVFKR (SEQ ID NO:72), VQESSVFIPRR (SEQ ID NO:73), EWIQRMMEVLRKRSSSTLPVPVFKRK (SEQ ID NO:74), KKNK (SEQ ID NO:75), RKRSSS (SEQ ID NO:76), RGNGCP (SEQ ID NO:77), VYYTSLRCRCVQESSVFIPRR (SEQ ID NO:78), DRIQILP (SEQ ID NO:79), RKEIIVW (SEQ ID NO:80) and KSIVCVDPQ (SEQ ID NO:81). Examples of the CXCR5 immunogenic peptides include, but are not limited to, peptides consisting of, or comprising, one or more sequences selected from the group consisting of TSLVENHLCPATE (SEQ ID NO:82), EGSVGWVLGTFLCKT (SEQ ID NO:83), LPRCTFS (SEQ ID NO:84), LARLKAVDNT (SEQ ID NO:85) and MASFKAVFVP (SEQ ID NO:86).

The term "CXCL16 immunogen" and "CXCR6 immunogen" refers to an immunogenic composition comprising (1) an immunogenic peptide derived from CXCL16 or CXCR6 and/or (2) an expression vector that encodes, and is capable of expressing, an immunogenic peptide derived from CXCL16 or CXCR6. The immunogenic peptide derived from CXCL16 or CXCR6 may be in the form of a fusion protein to enhance its immunogenicity. Examples of the CXCL16 immunogenic peptides include, but are not limited to, peptides consisting of, or comprising, one or more sequences selected from the group consisting of AAGPEAGENQKQPEKN (SEQ ID NO:87), SQASEGASSDIHTPAQ (SEQ ID NO:88), STLQSTQRPTLPVGSL (SEQ ID NO:89), SWSVCGGNKDPWVQEL (SEQ ID NO:90), GPTARTSATVPVLCLL (SEQ ID NO:91), SGIVAHQKHLLPTSPP (SEQ ID NO:92), RLRKHL (SEQ ID NO:93), LQSTQRP (SEQ ID NO:94), SSDKELTRPNETT (SEQ ID NO:95), AGENQKQPEKNA (SEQ ID NO:96), NEGSVT (SEQ ID NO:97), ISSDSPPSV (SEQ ID NO:98), CGGNKDPW (SEQ ID NO:99), LLPTSPPISQASEGASSDIHT (SEQ ID NO:100), STQRPTLPVGSLSSDKELTRPNETTIHT (SEQ ID NO:101), SLAAGPEAGENQKQPEKNAGPTARTSA (SEQ ID NO:102), TGSCYCGKR (SEQ ID NO:103), DSPPSVQ (SEQ ID NO:104), RKHLRAYHRCLYYTRFQLLSWSVCGG (SEQ ID NO:105), WVQELMSCLDLKECGHAYSGIVAHQKHLLPTSPPISQ (SEQ ID NO:106), SDIHTPAQMLLSTLQ (SEQ ID NO:107), RPTLPVGSL (SEQ ID NO:108), TAGHSLAAG (SEQ ID NO:109), GKRISSDSPPSVQ (SEQ ID NO:110), KDPWVQELMSCLDLKECGHAYSGIVAHQKH (SEQ ID NO:111). Examples of the CXCR6 immunogenic peptides include, but are not limited to, peptides consisting of, or comprising, one or more sequences selected from the group consisting of HQDFLQFSKV (SEQ ID NO:112), AGIHEWVFGQVMCK (SEQ ID NO:113), PQIIYGNVFNLDKLICGYHDEAI (SEQ ID NO:114) and YYAMTSFHYTIMVTEA (SEQ ID NO:115).

The term "biological sample," as used herein, refers to material of a biological origin, which may be a body fluid or body product such as blood, plasma, urine, saliva, spinal fluid, stool, sweat or breath. Biological sample also includes tissue samples and cell samples.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed.

CXCL13-CXCR5 Binding Mediates DOCK2-Dependent Chemotaxis

CXCL13, also known as B lymphocyte chemoattractant (BLC), is a ligand for the CXCR5 chemokine receptor. Both the chemokine and the receptor appear to play a role in the regulation of metastasis and invasion of cancer. Both CXCL13 and CXCR5 are locally up-regulated in multiple carcinoma tissue types compared to normal tissues, including ovarian, lung, breast, prostate, bone and pancreatic cancers. CXCL13 levels are also increased in the serum of patients with those cancers. Additionally, soluble CXCL13 chemokine enhances both in vivo and in vitro proliferation and migration of cancer cells.

CXCR5 (CD185), also known as Burkett lymphoma receptor 1 (BLR1) is a member of the chemokine receptor family of G protein coupled receptors (GPCRs) that may have a diverse role in cancer cell survival that presumably supports protection against chemotherapeutic drugs. Interaction of CXCR5 with CXCL13 activates DOCK2 (Dedicator of cytokenesis 2), which binds to the DOCK-binding protein ELMO1 (Engulfment and cell motility protein 1), allowing DOCK2-mediated Rae (Ras-related C3 botulinum toxin substrate proteins, a family of signaling G proteins that is a subfamily of the Rho family of GTPases) activation in lymphocytes. DOCK2 binds both the Rac1 and Rac2 isoforms and DOCK2-dependent Rac activation regulates neutrophil NADPH oxidase and is important for chemotaxis in neutrophils. In the present invention, the term "CXCR5" is inclusive of the transcription variants of CXCR5, such as CXCR5a (CXCR5 transcription variant 2) and CXCR5b (CXCR5 transcription variant 1).

Methods for Treating or Preventing Cancer Using Anti-CXCL13, Anti-CXCR5, Anti-CXCL16 and/or Anti-CXCR6 Antibodies One aspect of the present invention relates to methods for treating or preventing cancer using an anti-CXCL13 antibody and/or an anti-CXCR5 antibody. The method comprises administering to a subject in need of such treatment, a therapeutically effective amount of an anti-CXCL13 antibody, an anti-CXCR5 antibody, or a combination thereof. In one embodiment, the cancer is melanoma, lymphoma, myeloma, leukemia, sarcoma, blastoma or a carcinoma. Examples of carcinoma include, but are not limited to, acinic cell carcinoma, adenoid cystic carcinoma, adenocarcinoma, adenosquamous carcinoma, adrenocortical adenoma, adrenocortical carcinoma, anaplastic carcinoma, apudoma, basal cell carcinoma, carcinoid, carcinosarcoma, clear cell carcinoma, cylindroma, cystadenocarcinoma, ductal carcinoma, gastrinoma, giant cell carcinoma, glioma, glucagonoma, Hurthle cell carcinoma, insulinoma, large cell carcinoma, lobular carcinoma, medulloblastoma, medullary carcinoma, mucinous cystadenoma, mucoepidermoid carcinoma, neuroectodermal tumor, oncocytoma, papillary hidradenoma, papilloma, pleomorphic carcinoma, pulmonary blastoma, sarcomatoid carcinoma, serous cystadenoma, Signet ring cell carcinoma, small cell carcinoma, somatostatinoma, spindle cell carcinoma, squamous cell carcinoma, thymoma, verrucous carcinoma, and of organs or tissues that line the inner or outer surfaces of the body originating from endodermal, extodermal, or epithelial cells. These organs and tissues include, but are not limited to: bone, breast, central nervous system, cervix, colon, endometrium, esophagus, fallopian tube, gastrointestinal tract, kidney, lung, lymphoid, mammary gland, oral cavity, ovary, pancreas, pituitary gland, prostate, rectum, reproductive tract, respiratory tract, stomach, sweat gland, thymus, thyroid, uterus, vagina.

In another embodiment, the subject is diagnosed with a cancer that results in elevated CXCL13 and/or CXCR5 expression in the cancer cells. Examples of such cancer include, but are not limited to, melanoma, lymphoma, myeloma, leukemia, sarcoma, blastoma and carcinoma. In one embodiment, the subject is diagnosed with brain cancer. In another embodiment, the subject is diagnosed with prostate cancer. In another embodiment, the method comprises the step of immunizing the subject with an effective amount of CXCL13 and/or CXCR5 immunogen(s) as protein, peptide or encoded gene to induce antibodies that inhibit the biological activity of CXCL13 and/or CXCR5. In another embodiment, the subject is diagnosed with bone cancer. In another embodiment, the subject is diagnosed with pituitary cancer. In yet another embodiment, the subject is diagnosed with ovarian cancer. In another embodiment, the subject is diagnosed with lung cancer. In another embodiment, the subject is diagnosed with breast cancer. In another embodiment, the subject is diagnosed with colon cancer. In another embodiment, the subject is diagnosed with lymphoma or myeloma. In another embodiment, the subject is diagnosed with leukemia.

In another embodiment, the method comprises the step of immunizing the subject with an effective amount of CXCL16 and/or CXCR6 immunogen(s) as protein, peptide or encoded gene to induce antibodies that inhibit the biological activity of CXCL16 and/or CXCR6.

In another embodiment, the method comprises the step of immunizing the subject with an effective amount of one or more of CXCL13 and CXCR5 immunogens and an effective amount of one or more of CXCL16 and CXCR6 immunogens.

Another aspect of the present invention relates to methods for inhibiting or preventing metastasis of a cancer by treatment of a subject in need thereof with an anti-CXCL13 antibody and/or an anti-CXCR5 antibody. In one embodiment, an anti-CXCL13 antibody and/or an anti-CXCR5 antibody inhibits or prevents invasion of a tissue by a cancer. In another embodiment, the method comprises the step of immunizing the subject with an effective amount of CXCL13 and/or CXCR5 immunogen(s) as protein, peptide or encoded gene to induce antibodies that inhibit the biological activity of CXCL13 and/or CXCR5. In some embodiments, the cancer is prostate cancer. In other embodiments, the cancer is melanoma. In some embodiments, said tissue is bone.

Another aspect of the present invention relates to methods for treatment of a subject in need thereof with an anti-CXCL13 antibody and/or an anti-CXCR5 antibody causing regression of an established tumor. In certain embodiments, the method comprises the step of immunizing the subject with an effective amount of CXCL13 and/or CXCR5 immunogen(s) as protein, peptide or encoded gene to induce antibodies that inhibit the biological activity of CXCL13 and/or CXCR5. In particular embodiments, the established tumor is an advanced tumor. In some embodiments, the established tumor is a metastatic tumor.

Another aspect of the present invention relates to methods for treatment of a subject in need thereof with an anti-CXCL13 antibody and/or an anti-CXCR5 antibody to prevent or inhibit osteolytic growth of a tumor in bone. In some embodiment, the method comprises the step of immunizing the subject with an effective amount of CXCL13 and/or CXCR5 immunogen(s) as protein, peptide or encoded gene to induce antibodies that inhibit the biological activity of CXCL13 and/or CXCR5. In some other embodiments, the tumor is a melanoma, lymphoma, sarcoma, blastoma or carcinoma. In some embodiments, the tumor is a carcinoma. In a particular embodiment, the tumor is prostate cancer. In some embodiments, the treatment with an anti-CXCL13 antibody and/or an anti-CXCR5 antibody prevents osteolysis or bone resorption by a tumor.

In another embodiment, the method further comprises determining the level of CXCL13 and/or CXCR5 expression in a tissue from the subject, and, if an increased level of CXCL13 and/or CXCR5 is detected, administering to the subject a therapeutically effective amount of an anti-CXCL13 antibody, an anti-CXCR5 antibody, or a combination thereof. In another embodiment, the method comprises the step of immunizing the subject with an effective amount of CXCL13 and/or CXCR5 immunogen(s) as protein, peptide or encoded gene to induce antibodies that inhibit the biological activity of CXCL13 and/or CXCR5.

A preferred antibody of the present invention is one which binds to human CXCL13 and preferably blocks (partially or completely) the ability of CXCL13 to bind to a receptor, including, but not limited to, CXCR5. Another preferred antibody of the present invention is one which binds to human CXCR5 and preferably blocks (partially or completely) the ability of a cell, such as a tumor or carcinoma cell, expressing the CXCR5 chemokine receptor at its cell surface to bind to a ligand, including, but not limited to, CXCL13. Yet another preferred antibody of the present invention is one which binds to human CXCR5 and preferably blocks (partially or completely) the ability of soluble CXCR5 chemokine receptor to bind to a ligand, including, but not limited to, CXCL13.

In one embodiment, the anti-CXCL13 antibody and/or anti-CXCR5 antibody is a monoclonal antibody. In another embodiment, the anti-CXCL13 antibody and/or anti-CXCR5 antibody is a humanized antibody. In another embodiment, the anti-CXCL13 antibody and/or anti-CXCR6 antibody is a humanized antibody fragment.

In particular embodiments of the present invention, treatment of a subject with an anti-CXCL13 and/or anti-CXCR5 antibody is in conjunction with the treatment of the subject beforehand, at the same time, or afterward with a therapeutically effective amount of at least one other antibody that is specific for another antigen. In one embodiment, the another antigen is another chemokine or chemokine receptor, such as CXCL1, CXCL2, CXCL3, CXCL4, CXCL5, CXCL6, CXCL7, CXCL8, CXCL9, CXCL10, CXCL11, CXCL12, CXCL14, CXCL15, CXCL16, CXCR1, CXCR2, CXCR3, CXCR4, CXCR5a, CXCR5b, CXCR6, CXCR7, CCL1, CCL2, CCL3, CCL4, CCL5, CCL6, CCL7, CCL8, CCL9, CCL10, CCL11, CCL12, CCL13, CCL14, CCL15, CCL16, CCL17, CCL18, CCL19, CCL20, CCL21, CCL22, CCL24, CCL25, CCL25-1, CCL25-2, CCL27, CCL28, CCR1, CCR2, CCR3, CCR4, CCR5, CCR6, CCR7, CCR8, CCR9, CCR10, CCR11, XCL1, XCL2, XCR1, CX3CR1, or CX3CL1.

In another embodiment, the another antigen is a chemokine or chemokine receptor associated with a carcinoma and selected from the group consisting of CCL1, CCL2, CCL4, CCL17, CCL19, CCL21, CCL22, CCL25, CXCL12, CXCL16, CCR2, CCR7, CCR8, CCR9, CXCR4, CXCR6, CXCR7, CX3CL1 and CX3CR1.

In another embodiment, the another antigen is a chemokine or chemokine receptor associated with a melanoma and selected from the group consisting of CCL25, CCL27, CXCL1, CXCL2, CXCL3, CXCL5, CXCL6, CXCL7, CXCL8, CXCL12, CXCL16, CX3CL1, CCR2, CCR9, CCR10, CXCR1, CXCR2, CXCR4, CXCR6, CXCR7 and CX3CR1.

In another embodiment, the another antigen is a chemokine or chemokine receptor associated with a lymphoma and selected from the group consisting of CXCL12, CXCR4, CXCR7, CCR2.

In another embodiment, the another antigen is a chemokine or chemokine receptor associated with a myeloma or leukemia.

In another embodiment, the another antigen is selected from the polypeptides recited in Table 1 and/or Table 2, and fragments of any of said polypeptides.

Other exemplary antigens include molecules such as renin; a growth hormone, including human growth hormone and bovine growth hormone; growth hormone releasing factor; parathyroid hormone; thyroid stimulating hormone; lipoproteins; a-1-antitrypsin; insulin A-chain; insulin B-chain; proinsulin; follicle stimulating hormone; calcitonin; luteinizing hormone; glucagon; clotting factors such as factor VIII, factor IX, tissue factor, and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-□ and -β; enkephalinase; a serum albumin such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; vascular endothelial growth factor (VEGF); receptors for hormones or growth factors; protein A or D; rheumatoid factors; a neurotrophic factor such as bone-derived neurotrophic factor (BDNF), neurotrophin-3, -4, -5, or -6 (NT-3, NT4, NT-5, or NT-6), or a nerve growth factor such as NGF-β; platelet-derived growth factor (PDGF); fibroblast growth factor such as aFGF and bFGF; epidermal growth factor (EGF); members of the ErbB receptor family such as the EGF receptor; transforming growth factor (TGF) such as TGF-α and TGF-β, including TGF-β1, TGF-β2, TGF-β3, TGF-β4, or TGF-β5; insulin-like growth factor-I and -II (IGF-I and IGF-II); des(1-3)-IGF-I (brain IGF-I), insulin-like growth factor binding proteins; CD proteins such as CD3, CD4, CD8, CD19, CD20 and CD34; erythropoietin; osteoinductive factors; immunotoxins; a bone morphogenetic protein (BMP); an interferon such as interferon-α, -β, and -γ; colony stimulating factors (CSFs), e.g., M-CSF, GM-CSF, and G-CSF; interleukins (ILs), e.g., IL-1, IL-2, IL-3, IL-4, IL-5, IL-6, IL-7, IL-8, IL-9 and/or IL-10; superoxide dismutase; T-cell receptors; surface membrane proteins; decay accelerating factor; viral antigen such as, for example, a portion of the AIDS envelope; transport proteins; homing receptors; addressins; regulatory proteins; αv/β3 integrin including either a or b subunits thereof, such as CD11a, CD11b, CD11c, CD18, an ICAM, VLA-4 and VCAM; prostate specific antigen (PSA); a tumor associated antigen such as carcinoembryonic antigen (CEA), CK2, CA125, TA90, HER2, HER3 or HER4 receptor; blood group antigens; flk2/flt3 receptor; obesity (OB) receptor; mp1 receptor; CTLA-4; protein C; any one of the proteins from the classical, lectin or alternative complement pathways; and fragments of any of the above-listed polypeptides.

The antibody may be administered to the subject with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes. In certain embodiments, the antibody is administered directly to a tumor or cancer tissue, including administration directly to the tumor bed during invasive procedures. The antibody may also be placed on a solid support such as a sponge or gauze for administration against the target chemokine to the affected tissues.

Antibodies of the invention can be administered in the usually accepted pharmaceutically acceptable carriers. Acceptable carriers include, but are not limited to, saline, buffered saline, and glucose in saline. Solid supports, liposomes, nanoparticles, microparticles, nanospheres or microspheres may also be used as carriers for administration of the antibodies.

The appropriate dosage ("therapeutically effective amount") of the antibody will depend, for example, on the condition to be treated, the severity and course of the condition, whether the antibody is administered for preventive or therapeutic purposes, previous therapy, the patient's clinical history and response to the antibody, the type of antibody used, and the discretion of the attending physician. The antibody is suitably administered to the patent at one time or over a series of treatments and may be administered to the patient at any time from diagnosis onwards. The antibody may be administered as the sole treatment or in conjunction with other drugs or therapies useful in treating the condition in question.

As a general proposition, the therapeutically effective amount of the antibody administered will be in the range of about 1 ng/kg body weight/day to about 100 mg/kg body weight/day whether by one or more administrations. In a particular embodiments, the range of antibody administered is from about 1 ng/kg body weight/day to about 1 µg/kg body weight/day, 1 ng/kg body weight/day to about 100 ng/kg body weight/day, 1 ng/kg body weight/day to about 10 ng/kg body weight/day, 10 ng/kg body weight/day to about 1 µg/kg body weight/day, 10 ng/kg body weight/day to about 100 ng/kg body weight/day, 100 ng/kg body weight/day to about 1 µg/kg body weight/day, 100 ng/kg body weight/day to about 10 µg/kg body weight/day, 1 µg/kg body weight/day to about 10 µg/kg body weight/day, 1 µg/kg body weight/day to about 100 µg/kg body weight/day, 10 µg/kg body weight/day to about 100 µg/kg body weight/day, 10 µg/kg body weight/day to about 1 mg/kg body weight/day, 100 µg/kg body weight/day to about 10 mg/kg body weight/day, 1 mg/kg body weight/day to about 100 mg/kg body weight/day and 10 mg/kg body weight/day to about 100 mg/kg body weight/day.

In another embodiment, the antibody is administered at a dosage range of 1 ng-10 ng per injection, 10 ng to 100 ng per injection, 100 ng to 1 µg per injection, 1 µg to 10 µg per injection, 10 µg to 100 µg per injection, 100 µg to 1 mg per injection, 1 mg to 10 mg per injection, 10 mg to 100 mg per injection, and 100 mg to 1000 mg per injection. The antibody may be injected daily, or every 2, 3, 4, 5, 6 and 7 days, or every 1, 2, 3 or 4 weeks.

In another particular embodiment, the dose range of antibody administered is from about 1 ng/kg to about 100 mg/kg In still another particular embodiment, the range of antibody administered is from about 1 ng/kg to about 10 ng/kg, about 10 ng/kg to about 100 ng/kg, about 100 ng/kg to about 1 µg/kg, about 1 µg/kg to about 10 µg/kg, about 10 µg/kg to about 100 µg/kg, about 100 µg/kg to about 1 mg/kg, about 1 mg/kg to about 10 mg/kg, about 10 mg/kg to about 100 mg/kg, about 0.5 mg/kg to about 30 mg/kg, and about 1 mg/kg to about 15 mg/kg.

In other particular embodiments, the amount of antibody administered is, or is about, 0.0006, 0.001, 0.003, 0.006, 0.01, 0.03, 0.06, 0.1, 0.3, 0.6, 1, 3, 6, 10, 30, 60, 100, 300, 600 and 1000 mg/day. As expected, the dosage will be dependant on the condition, size, age and condition of the patient.

The antibody may be administered, as appropriate or indicated, a single dose as a bolus or by continuous infusion, or as multiple doses by bolus or by continuous infusion. Multiple doses may be administered, for example, multiple times per day, once daily, every 2, 3, 4, 5, 6 or 7 days, weekly, every 2, 3, 4, 5 or 6 weeks or monthly. However, other dosage regimens may be useful. The progress of this therapy is easily monitored by conventional techniques.

In particular embodiments of the present invention, therapeutically effective amount of anti-CXCL13 and/or anti-CXCR5 antibody may be administered to a subject in need thereof as a sole therapeutic agent. In a particular embodiment, the therapeutically effective amount of anti-CXCL13 and/or anti-CXCR5 antibody to kill or promote apoptosis of the tumor or carcinoma cells. In another particular embodiment, the therapeutically effective amount of anti-CXCL13 and/or anti-CXCR5 antibody inhibits or prevents the establishment of a tumor or carcinoma. In a further particular embodiment, the therapeutically effective amount of anti-CXCL13 and/or anti-CXCR5 antibody inhibits or prevents the migration or metastasis of tumor or carcinoma cells from an existing tumor or carcinoma. In yet another particular embodiment, the therapeutically effective amount of anti-CXCL13 and/or anti-CXCR5 antibody inhibits or prevents the invasion of tumor or carcinoma cells into non-cancerous tissues.

In particular embodiments of the present invention, therapeutically effective amount of anti-CXCL13 and/or anti-CXCR5 antibody may be administered to a subject in need thereof in conjunction with one or more additional therapeutically effective antibodies. Said one or more additional therapeutically effective antibodies may be directed to additional determinants on CXCL13 and/or CXCR5, other chemokines, other chemokine receptors, other soluble or cell surface ligands or receptors including, but not limited to, tumor or carcinoma specific antigens, viral, bacterial or parasite antigens, products of cancer cells or remnants of apoptosis. The anti-CXCL13 and/or anti-CXCR5 antibody may be administered before, concurrently with, and/or after the one or more additional therapeutically effective antibodies.

In a particular embodiment, the therapeutically effective amount of anti-CXCL13 and/or anti-CXCR5 antibody augments the effectiveness of the one or more additional therapeutically effective antibodies in killing tumor or carcinoma cells. In a more particular embodiment, the therapeutically effective amount of anti-CXCL13 and/or anti-CXCR5 antibody reduces the amount of the one or more additional therapeutically effective antibodies required for killing tumor or carcinoma cells. In a further particular embodiment, the therapeutically effective amount of anti-CXCL13 and/or anti-CXCR5 antibody inhibits or prevents the migration or metastasis of tumor or carcinoma cells from an established tumor or carcinoma, enhancing the local effectiveness of the one or more additional therapeutically effective antibodies in killing tumor or carcinoma cells. In yet another particular embodiment, the therapeutically effective amount of anti-CXCL13 and/or anti-CXCR5 antibody inhibits or prevents the invasion of tumor or carcinoma cells into non-cancerous tissues, enhancing the local effectiveness of the one or more additional therapeutically effective antibodies in killing tumor or carcinoma cells.

In another embodiment, the anti-CXCL13 antibody and/or anti-CXCR5 antibody is an antibody conjugated to a cytotoxic agent. In another embodiment, the anti-CXCL13 antibody and/or anti-CXCR5 antibody is administered with another anti-cancer agent, such as chemotherapy agent.

Another aspect of the present invention relates to a method of inhibiting the interaction of the chemokine CXCL13 with a receptor therefore, comprising contacting the cell with an effective amount of an antibody or functional fragment thereof which binds to a mammalian CXCL13 or a portion of CXCL13.

Another aspect of the present invention relates to a method of inhibiting the interaction of a cell bearing CXCR5 with a ligand thereof, comprising contacting the cell with an effective amount of an antibody or functional fragment thereof which binds to a mammalian CXCR5 or a portion of CXCR5.

In another embodiment, the method of treating cancer comprises administering to an subject in need of such treatment, an effective amount of an expression vector that expresses an anti-CXCL13 antibody, an anti-CXCR5 antibody, or a combination thereof in a cancer or malignant cell. In another embodiment, the method of treating cancer comprises the step of immunizing the subject with an effective amount of CXCL13 and/or CXCR5 immunogen(s) to induce the host to produce antibodies that inhibit the biological activity of CXCL13 and/or CXCR5.

The expression vectors can be any vector that is capable of nucleotide deliver nucleotides encoding an anti-CXCL13 antibody and/or an anti-CXCR5 antibody into a target cell and express the anti-CXCL13 antibody and/or anti-CXCR5 antibody in the target cell. In another embodiment, the expression vector is capable of delivering nucleotides encoding CXCL13 and/or CXCR6 into a target cell to induce the host to produce anti-CXCL13 and/or CXCR5 antibodies. Examples of expression vectors include viral vectors and non-viral vectors.

Viral vectors include, but are not limited to, retrovirus vectors, adenovirus vectors, adeno-associated virus vectors, and other large capacity viral vectors, such as herpes virus and vaccinia virus. Also included are any viral families which share the properties of these viruses which make them suitable for use as expression vectors.

Retroviral Vectors

A retrovirus is an animal virus belonging to the virus family of Retroviridae, including any types, subfamilies, genus, or tropisms. Examples of methods for using retroviral vectors for gene therapy are described in U.S. Pat. Nos. 4,868,116 and 4,980,286; PCT applications WO 90/02806 and WO 89/07136; and Mulligan, (Science 260:926-932 (1993)); the teachings of which are incorporated herein by reference.

Adenoviral Vectors

Recombinant adenoviruses have been shown to achieve high efficiency gene transfer after direct, in vivo delivery to airway epithelium, hepatocytes, vascular endothelium, CNS parenchyma and a number of other tissue sites. Recombinant adenoviruses achieve gene transduction by binding to specific cell surface receptors, after which the virus is internalized by receptor-mediated endocytosis, in the same manner as wild type or replication-defective adenovirus.

A viral vector can be one based on an adenovirus which has had one or more viral genes removed and these virions are generated in a complement cell line, such as the human 293 cell line. In one embodiment, the E1 gene is removed from the adenoviral vector. In another embodiment, both the E1 and E3 genes are removed from the adenoviral vector. In another embodiment, both the E1 and E4 genes are removed from the adenoviral vector. In another embodiment, the adenovirus vector is a gutless adenovirus vector.

Adeno-Associated Viral Vectors

Another type of viral vector is based on an adeno-associated virus (AAV). This defective parvovirus is a preferred vector because it can infect many cell types and is nonpathogenic to humans. AAV type vectors can transport about 4 to 5 kb and wild type AAV is known to stably insert into chromosome 19. Vectors which contain this site specific integration property are preferred. An especially preferred embodiment of this type of vector is the P4.1 C vector produced by Avigen, San Francisco, Calif., which can contain the herpes simplex virus thymidine kinase gene, HSV-tk, and/or a marker gene, such as the gene encoding the green fluorescent protein, GFP.

In another type of AAV virus, the AAV contains a pair of inverted terminal repeats (ITRs) which flank at least one cassette containing a promoter which directs cell-specific expression operably linked to a heterologous gene. Heterologous in this context refers to any nucleotide sequence or gene which is not native to the AAV or B19 parvovirus.

Typically the AAV and B19 coding regions have been deleted, resulting in a safe, noncytotoxic vector. The AAV ITRs, or modifications thereof, confer infectivity and site-specific integration, but not cytotoxicity, and the promoter directs cell-specific expression. U.S. Pat. No. 6,261,834 is herein incorporated by reference for material related to the AAV vector.

Large Payload Viral Vectors

Molecular genetic experiments with large human herpes viruses have provided a means whereby large heterologous DNA fragments can be cloned, propagated and established in cells permissive for infection with herpes viruses (Sun et al., Nature genetics 8: 33-41, 1994; Cotter and Robertson, Curr Opin Mol Ther 5: 633-644, 1999). These large DNA viruses (herpes simplex virus (HSV) and Epstein-Barr virus (EBV), have the potential to deliver fragments of human heterologous DNA>150 kb to specific cells. EBV recombinants can maintain large pieces of DNA in the infected B-cells as episomal DNA. Individual clones carried human genomic inserts up to 330 kb appeared genetically stable. The maintenance of these episomes requires a specific EBV nuclear protein, EBNA1, constitutively expressed during infection with EBV. Additionally, these vectors can be used for transfection, where large amounts of protein can be generated transiently in vitro. Herpesvirus amplicon systems are also being used to package pieces of DNA>220 kb and to infect cells that can stably maintain DNA as episomes. Other useful systems include, for example, replicating and host-restricted non-replicating vaccinia virus vectors.

Non-Viral vectors include plasmid expression vectors. Plasmid vectors typically include a circular double-stranded DNA loop into which additional DNA segments can be inserted.

In both viral and non-viral expression vectors, the polynucleotide encoding the antibody or antibodies is typically arranged in proximity and orientation to an appropriate transcription control sequence (promoter, and optionally, one or more enhancers) to direct mRNA synthesis. That is, the polynucleotide sequence of interest is operably linked to an appropriate transcription control sequence. Examples of such promoters include: viral promoters such as the immediate early promoter of CMV, LTR or SV40 promoter, polyhedron promoter of baculovirus, *E. coli* lac or trp promoter, phage T7 and lambda PL promoter, and other promoters known to control expression of genes in eukaryotic cells or their viruses. The promoters may be a tissue specific promoter.

The expression vector typically also contains a ribosome binding site for translation initiation, and a transcription terminator. The vector optionally includes appropriate sequences for amplifying expression. In addition, the expression vectors optionally comprise one or more selectable marker genes to provide a phenotypic trait for selection of transformed host cells, such as dihydrofolate reductase or neomycin resistance for eukaryotic cell culture, or such as tetracycline or ampicillin resistance in *E. coli*.

The expression vector can also include additional expression elements, for example, to improve the efficiency of translation. These signals can include, e.g., an ATG initiation codon and adjacent sequences. In some cases, for example, a translation initiation codon and associated sequence elements are inserted into the appropriate expression vector simultaneously with the polynucleotide sequence of interest (e.g., a native start codon). In such cases, additional translational control signals are not required. However, in cases where only a polypeptide coding sequence, or a portion thereof, is inserted, exogenous translational control signals, including an ATG initiation codon is provided. The initiation codon is placed in the correct reading frame to ensure translation of the polynucleotide sequence of interest. Exogenous transcriptional elements and initiation codons can be of various origins, both natural and synthetic. If desired, the efficiency of expression can be further increased by the inclusion of enhancers appropriate to the cell system in use (Scharf et al. (1994) Results Probl Cell Differ 20:125-62; Bitter et al. (1987) Methods in Enzymol 153:516-544).

In one embodiment, the expression vector contains an inducible or regulatable expression system. Examples of regulatable expression systems are briefly described below:

Ecdysone System.

The ecdysone system is based on the molting induction system found in *Drosophila*, but modified for inducible expression in mammalian cells. The system uses an analog of the *drosophila* steroid hormone ecdysone, muristerone A, to activate expression of the gene of interest via a heterodimeric nuclear receptor. Expression levels have been reported to exceed 200-fold over basal levels with no effect on mammalian cell physiology.

Progesterone System.

The progesterone receptor is normally stimulated to bind to a specific DNA sequence and to activate transcription through an interaction with its hormone ligand. Conversely, the progesterone antagonist mifepristone (RU486) is able to block hormone-induced nuclear transport and subsequent DNA binding. A mutant form of the progesterone receptor that can be stimulated to bind through an interaction with RU486 has been generated. To generate a specific, regulatable transcription factor, the RU486-binding domain of the progesterone receptor has been fused to the DNA-binding domain of the yeast transcription factor GAL4 and the trans-activation domain of the HSV protein VP16. The chimeric factor is inactive in the absence of RU486. The addition of hormone, however, induces a conformational change in the chimeric protein, and this change allows binding to a GAL4-binding site and the activation of transcription from promoters containing the GAL4-binding site.

Rapamycin System.

Immunosuppressive agents, such as FK506 and rapamycin, act by binding to specific cellular proteins and facilitating their dimerization. For example, the binding of rapamycin to FK506-binding protein (FKBP) results in its heterodimerization with another rapamycin binding protein FRAP, which can be reversed by removal of the drug. The ability to bring two proteins together by addition of a drug potentiates the regulation of a number of biological processes, including transcription. A chimeric DNA-binding domain has been fused to the FKBP, which enables binding of the fusion protein to a specific DNA-binding sequence. A transcriptional activation domain also has been fused to FRAP. When these two fusion proteins are co-expressed in the same cell, a fully functional transcription factor can be formed by heterodimerization mediated by addition of rapamycin. The dimerized chimeric transcription factor can then bind to a synthetic promoter sequence containing copies of the synthetic DNA-binding sequence. This system has been successfully integrated into adenoviral and AAV vectors. Long term regulatable gene expression has been achieved in both mice and baboons.

Methods for Treating or Preventing Cancer Using Agents that Inhibits the Expression or Activity of CXCL13 or CXCR5

Another aspect of the present invention relates to methods for treating or preventing cancer by using agents that inhibits the expression or activity of CXCL13 or CXCR5. In another embodiment, the method comprises administering to a subject in need of such treatment, an effective amount of an expression vector that expresses an agent that (1) inhibits the expression of CXCL13 and/or CXCR5, or (2) inhibits the interaction between CXCL13 and CXCR5, or (3) inhibits a biological activity of CXCL13 and/or CXCR5. In one embodiment, the biological activity of CXCL13 and CXCR5 includes the interaction between CXCL13 and CXCR5.

In another embodiment, the subject is diagnosed with a cancer that results in elevated CXCL13 and/or CXCR5 expression in the cancer cells. Examples of such cancer include, but are not limited to, melanoma, lymphoma, myeloma, leukemia and carcinoma, such as ovarian cancer, vaginal cancer, cervical cancer, uterine cancer, prostate cancer, anal cancer, rectal cancer, colon cancer, stomach cancer, pancreatic cancer, insulinoma, glucagonoma, adenocarcinoma, adenosquamous carcinoma, neuroendocrine tumor, breast cancer, lung cancer, esophageal cancer, oral cancer, brain cancer, medulloblastoma, neuroectodermal tumor, glioma, pituitary cancer, and bone cancer.

In another embodiment, the method further comprises determining the level of CXCL13 and/or CXCR5 expression in a tissue from the subject, and administering the agent to the subject only if an increased level of CXCL13 and/or CXCR5 is detected in the tissue.

In one embodiment, the expression vector is a viral vector. In another embodiment, the expression vector is a non-vector vector. In another embodiment, the expression vector is capable of delivering nucleotides encoding CXCL13 and/or CXCR5 into a target cell to induce the host to produce anti-CXCL13 and/or CXCR5 antibodies.

In another embodiment, the agent is an anti-CXCL13 antibody, an anti-CXCR5 antibody, or a combination thereof.

In yet another embodiment, the agent is a functional nucleic acid. Functional nucleic acids are nucleic acid molecules that have a specific function, such as binding a target molecule or catalyzing a specific reaction. The functional nucleic acid molecules can act as inhibitors of a specific activity possessed by a target molecule. Functional nucleic acid molecules can interact with any macromolecule, such as DNA, RNA and polypeptides. Thus, functional nucleic acids can interact with mRNA or the genomic DNA of CXCL13 or CXCR5 to inhibit expression or interact with CXCL13 or CXCR5 protein to inhibit activity. Often functional nucleic acids are designed to interact with other nucleic acids based on sequence homology between the target molecule and the functional nucleic acid molecule. In other situations, the specific recognition between the functional nucleic acid molecule and the target molecule is not based on sequence homology between the functional nucleic acid molecule and the target molecule, but rather is based on the formation of tertiary structure that allows specific recognition to take place. Examples of functional nucleic acid molecules include siRNA, antisense molecules, aptamers, ribozymes, triplex forming molecules, and external guide sequences.

siRNA is involved in RNA interference (RNAi) which involves a two-step mechanism: an initiation step and an effector step. In the first step, input double-stranded (ds) RNA (siRNA) is processed into small fragments, such as 21-23-nucleotide 'guide sequences'. RNA amplification occurs in whole animals. Typically then, the guide RNAs can be incorporated into a protein RNA complex which is capable of degrading RNA, the nuclease complex, which has been called the RNA-induced silencing complex (RISC). This RISC complex acts in the second effector step to destroy mRNAs that are recognized by the guide RNAs through base-pairing interactions. RNAi involves the introduction by any means of double stranded RNA into the cell which triggers events that cause the degradation of a target RNA. RNAi is a form of post-transcriptional gene silencing. In addition to the siRNAs disclosed herein, disclosed are RNA hairpins that can act in RNAi. For description of making and using RNAi molecules see, e.g., Hammond et al., Nature Rev Gen 2: 110-119 (2001); Sharp, Genes Dev 15: 485-490 (2001), Waterhouse et al., Proc. Natl. Acad. Sci. USA 95(23): 13959-13964 (1998) all of which are incorporated herein by reference in their entireties and at least form material related to delivery and making of RNAi molecules.

RNAi has been shown to work in many types of cells, including mammalian cells. For work in mammalian cells it is preferred that the RNA molecules which will be used as targeting sequences within the RISC complex are shorter. For example, less than or equal to 50 or 40 or 30 or 29, 28, 27, 26, 25, 24, 23, 22, 21, 20, 19, 18, 17, 16, 15, 14, 13, 12, 11, or 10 nucleotides in length. These RNA molecules can also have overhangs on the 3' or 5' ends relative to the target RNA which is to be cleaved. These overhangs can be at least or less than or equal to 1, 2, 3, 4, 5, 6, 7, 8, 9, 10, 15, or 20 nucleotides long.

Antisense molecules are designed to interact with a target nucleic acid molecule through either canonical or non-canonical base pairing. The interaction of the antisense molecule and the target molecule is designed to promote the destruction of the target molecule through, for example, RNAseH mediated RNA-DNA hybrid degradation. Alternatively the antisense molecule is designed to interrupt a processing function that normally would take place on the target molecule, such as transcription or replication. Antisense molecules can be designed based on the sequence of the target molecule. Numerous methods for optimization of antisense efficiency by finding the most accessible regions of the target molecule exist. Exemplary methods would be in vitro selection experiments and DNA modification studies using DMS and DEPC. It is preferred that antisense molecules bind the target molecule with a dissociation constant (kd) less than or equal to $10^{-6}$, $10^{-8}$, $10^{-10}$, or $10^{-12}$. A representative sample of methods and techniques which aid in the design and use of antisense molecules can be found in the following non-limiting list of U.S. Pat. Nos. 5,135,917, 5,994,320, 6,046,319, and 6,057,437.

Aptamers are molecules that interact with a target molecule, preferably in a specific way. Typically aptamers are small nucleic acids ranging from 15-50 bases in length that fold into defined secondary and tertiary structures, such as stem-loops or G-quartets. Aptamers can bind a chemokines and block its function (see, e.g., Marro et al., Biochem Biophys Res Commun. 2006 Oct. 13; 349:270-6). Aptamers can bind very tightly with kds from the target molecule of less than $10^{-12}$ M. It is preferred that the aptamers bind the target molecule with a $k_d$ less than $10^{-6}$, $10^{-8}$, $10^{10}$, or $10^{-12}$. Aptamers can bind the target molecule with a very high degree of specificity. For example, aptamers have been isolated that have greater than a 10000 fold difference in binding affinities between the target molecule and another molecule that differ at only a single position on the molecule (U.S. Pat. No. 5,543,293). It is preferred that the aptamer have a $k_d$ with the target molecule at least 10, 100, 1000, 10,000, or 100,000 fold lower than the $k_d$ with a background binding molecule. Representative examples of how to make and use aptamers to bind a variety of different target molecules can be found in the following non-limiting list of U.S. Pat. Nos. 5,476,766, 5,861,254, 6,030,776, and 6,051,698.

Ribozymes are nucleic acid molecules that are capable of catalyzing a chemical reaction, either intramolecularly or intermolecularly. Ribozymes are thus catalytic nucleic acid. It is preferred that the ribozymes catalyze intermolecular reactions. There are a number of different types of ribozymes that catalyze nuclease or nucleic acid polymerase type reactions which are based on ribozymes found in natural systems, such as hammerhead ribozymes, (see, e.g., U.S. Pat. Nos. 5,334,711 and 5,861,288, WO 9858058 and WO 9718312) hairpin ribozymes (see, e.g., U.S. Pat. Nos. 5,631,115 and 6,022,962), and tetrahymena ribozymes (see, e.g., U.S. Pat. Nos. 5,595,873 and 5,652,107). There are also a number of ribozymes that are not found in natural systems, but which have been engineered to catalyze specific reactions de novo (see, e.g., U.S. Pat. Nos. 5,580,967 and 5,910,408). Preferred ribozymes cleave RNA or DNA substrates, and more preferably cleave RNA substrates. Ribozymes typically cleave nucleic acid substrates through recognition and binding of the target substrate with subsequent cleavage. This recognition is often based mostly on canonical or non-canonical base pair interactions. This property makes ribozymes particularly good candidates for target specific cleavage of nucleic acids because recognition of the target substrate is based on the target substrates sequence. Representative examples of how to make and use ribozymes to catalyze a variety of different reactions can be found in U.S. Pat. Nos. 5,646,042, 5,869, 253, 5,989,906, and 6,017,756.

Triplex forming functional nucleic acid molecules are molecules that can interact with either double-stranded or single-stranded nucleic acid. When triplex molecules interact with a target region, a structure called a triplex is formed, in which three strands of DNA are forming a complex dependant on both Watson-Crick and Hoogsteen base-pairing. Triplex molecules are preferred because they can bind target regions with high affinity and specificity. It is preferred that the triplex forming molecules bind the target molecule with a $k_d$ less than $10^{-6}$, $10^{-8}$, $10^{-10}$, or $10^{-12}$. Representative examples of how to make and use triplex forming molecules to bind a variety of different target molecules can be found in U.S. Pat. Nos. 5,176,996, 5,683,874, 5,874,566, and 5,962,426.

External guide sequences (EGSs) are molecules that bind a target nucleic acid molecule forming a complex, and this complex is recognized by RNase P, which cleaves the target molecule. EGSs can be designed to specifically target a RNA molecule of choice. RNAse P aids in processing transfer RNA (tRNA) within a cell. Bacterial RNAse P can be recruited to cleave virtually any RNA sequence by using an EGS that causes the target RNA:EGS complex to mimic the natural tRNA substrate (see, e.g., WO 92/03566 by Yale, and Forster and Altman, *Science* 238:407-409 (1990)).

Similarly, eukaryotic EGS/RNAse P-directed cleavage of RNA can be utilized to cleave desired targets within eukaryotic cells. (Yuan et al., *Proc. Natl. Acad. Sci. USA* 89:8006-8010 (1992); WO 93/22434 by Yale; WO 95/24489 by Yale; Yuan and Altman, *EMBO J* 14:159-168 (1995), and Carrara et al., *Proc. Natl. Acad. Sci. USA* 92:2627-2631 (1995)). Representative examples of how to make and use EGS molecules to facilitate cleavage of a variety of different target molecules be found in the following non-limiting list of U.S. Pat. Nos. 5,168,053, 5,624,824, 5,683,873, 5,728,521, 5,869,248, and 5,877,162.

Methods for Prevention or Inhibition of Migration or Metastasis of Cancer Cells with Elevated Expression of CXCL13 and/or CXCR5

Another aspect of the present invention relates to a method for prevention or inhibition of the migration or metastasis of cancer cells with elevated expression of CXCL13 and/or CXCR5 in a subject.

In one embodiment, the method comprises the step of administering to the subject a therapeutically effective amount of an anti-CXCL13 antibody, or an anti-CXCR5 antibody, or a combination thereof.

In another embodiment, the method comprises the step of administering to the subject an expression vector that expresses an anti-CXCL13 antibody, or an anti-CXCR5 antibody, or a combination thereof in said subject.

In another embodiment, the method comprises administering to the subject an expression vector that expresses an agent capable of inhibiting the expression of CXCL13 or CXCR5, or a biological activity of CXCL13 or CXCR5, or the interaction between CXCL13 and CXCR5. In one embodiment, the expression vector is capable of delivering nucleotides encoding CXCL13 and/or CXCR5 into a target cell to induce the host to produce anti-CXCL13 and/or CXCR5 antibodies.

Expression of CXCL13 and/or CXCR5 in cancer cells can be determined using methods well known in the art, such as immunostaining or quantitative PCR. Cancer cells that are known to overexpress CXCL13 and/or CXCR5 include, but are not limited to, melanoma cells and carcinoma cells. Examples of carcinoma include, but are not limited to, ovarian cancer, vaginal cancer, cervical cancer, uterine cancer, prostate cancer, anal cancer, rectal cancer, colon cancer, stomach cancer, pancreatic cancer, insulinoma, adenocarcinoma, adenosquamous carcinoma, neuroendocrine tumor, breast cancer, lung cancer, esophageal cancer, oral cancer, brain cancer, medulloblastoma, neuroectodermal tumor, glioma, pituitary cancer, and bone cancer.

In one embodiment, the cancer cells are brain cancer cells. In another embodiment, the cancer cells are bone cancer cells. In another embodiment, the cancer cells are pituitary cancer cells. In yet another embodiment, the cancer cells are ovarian cancer cells.

Method for Enhancing the Effect of Chemotherapy

Another aspect of the present invention relates to a method for enhancing the effect of chemotherapy. In one embodiment, the method comprises administering to a subject who is under chemotherapy for a cancer, an effective amount of an anti-CXCL13 antibody, or an anti-CXCR5 antibody, or a combination thereof.

In another embodiment, the method comprises administering to a subject who is under chemotherapy for a cancer, an effective amount of an expression vector that expresses anti-CXCL13 antibody, or an anti-CXCR5 antibody, or a combination thereof.

In another embodiment, the method comprises administering to a subject who is under chemotherapy for a cancer an expression vector that expresses an agent capable of inhibiting the expression of CXCL13 or CXCR5, or a biological activity of CXCL13 or CXCR5, or the interaction between CXCL13 and CXCR5. In another embodiment, the expression vector is capable of delivering nucleotides encoding CXCL13 and/or CXCR5 into a target cell to induce the host to produce anti-CXCL13 and/or CXCR5 antibodies.

In one embodiment, the subject is under chemotherapy for melanoma, lymphoma, myeloma, leukemia or carcinoma. In another embodiment, the subject is under chemotherapy for brain cancer. In another embodiment, the subject is under chemotherapy for bone cancer. In another embodiment, the subject is under chemotherapy for pituitary cancer. In yet another embodiment, the subject is under chemotherapy for ovarian cancer.

Compositions and Kits for Treating of Preventing Cancer

Another aspect of the present invention relates to compositions and kits for treating or preventing cancer. In one embodiment, the composition comprises (1) an anti-CXCL13 antibody, an anti-CXCR5 antibody, or a combination thereof, and (2) a pharmaceutically acceptable carrier. In another embodiment, the composition comprises (1) an expression vector carrying the coding sequence for an anti-CXCL13 antibody, an anti-CXCR5 antibody, or a combination thereof, and (2) a pharmaceutically acceptable carrier. In another embodiment, the composition comprises (1) an expression vector carrying the coding sequence for an agent that inhibits the expression of CXCL13 or CXCR5, or a biological activity of CXCL13 or CXCR5, or the interaction between CXCL13 and CXCR5, and (2) a pharmaceutically acceptable carrier.

The composition of the present invention may contain a single type of antibody, such as an anti-CXCL13 or anti-CXCR5 antibody alone, or both types of antibodies. The composition may also contain therapeutically effective amounts of antibodies specific for one or more additional antigens as described above as necessary for the particular indication being treated, preferably those with complementary activities that do not adversely affect one another. For example, where the carcinoma being treated is ovarian cancer, it may be desirable to prepare a therapeutic formulation comprising anti-CXCL13 and/or -CXCR5 with one or more further anti-cancer determinant antibodies, such as an anti-CEA, anti-CA125 and/or anti-TA90 in a single formulation. In some embodiments of the present invention, a therapeutic antibody may be combined with an chemotherapy agent or a cytotoxic agent. In other embodiments of the present invention, a therapeutic antibody may be combined with an anti-inflammatory agent or a thrombolytic agent. Such agents are suitably present in combination in amounts that are effective for the purpose intended.

As used herein the language "pharmaceutically acceptable carrier" is intended to include any and all solvents, solubilizers, fillers, stabilizers, binders, absorbents, bases, buffering agents, lubricants, controlled release vehicles, diluents, emulsifying agents, humectants, lubricants, dispersion media, coatings, antibacterial or antifungal agents, isotonic and absorption delaying agents, and the like, compatible with pharmaceutical administration. The use of such media and agents for pharmaceutically active substances is well-known in the art. Except insofar as any conventional media or agent is incompatible with the active compound, use thereof in the compositions is contemplated. Supplementary agents can also be incorporated into the compositions. In certain embodiments, the pharmaceutically acceptable carrier comprises serum albumin.

The pharmaceutical composition of the invention is formulated to be compatible with its intended route of administration. Examples of routes of administration include parenteral, e.g., intrathecal, intra-arterial, intravenous, intradermal, subcutaneous, oral, transdermal (topical) and transmucosal administration. In certain embodiments, the pharmaceutical composition is administered directly into a tumor tissue.

Solutions or suspensions used for parenteral, intradermal, or subcutaneous application can include the following components: a sterile diluent such as water for injection, saline solution, fixed oils, polyethylene glycols, glycerine; propylene glycol or other synthetic solvents; antibacterial agents such as benzyl alcohol or ethyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the injectable composition should be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the requited particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a neuregulin) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Stertes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the pharmaceutical compositions are formulated into ointments, salves, gels, or creams as generally known in the art.

In certain embodiments, the pharmaceutical composition is formulated for sustained or controlled release of the active ingredient. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from e.g. Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein includes physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within orange of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. In certain embodiments, single dosage contains 0.01 ug to 50 mg of a chimeric neuregulin. The pharmaceutical compositions can be included in a container, pack, or dispenser together with instructions for administration.

The present invention is further illustrated by the following examples that should not be construed as limiting. The contents of all references, patents, and published patent applications cited throughout this application, as well as the Figures and Tables, are incorporated herein by reference.

Example 1

In Vitro Analysis of DOCK2 Expression in Cancer Cell Lines and CXCL13-CXCR5 Mediation of Cancer Cell Invasion Total cell lysates (60 µg) from RWPE-1, LNCaP, and PC3 cells were resolved by SDS-PAGE and subjected to immunoblotting using antibodies against DOCK2 (FIG. 1A). GAPDH served as loading control. In FIG. 1B, DOCK2 silencing conditions were optimized by transfecting PC3 cells with 2 µM of DOCK2 siRNA duplex following manufacturer's protocol (Santa Cruz), and incubating cells for 0, 24, 48, and 72 hours. The efficacy of DOCK2 silencing was determined by Western blot analysis.

Figure 2:
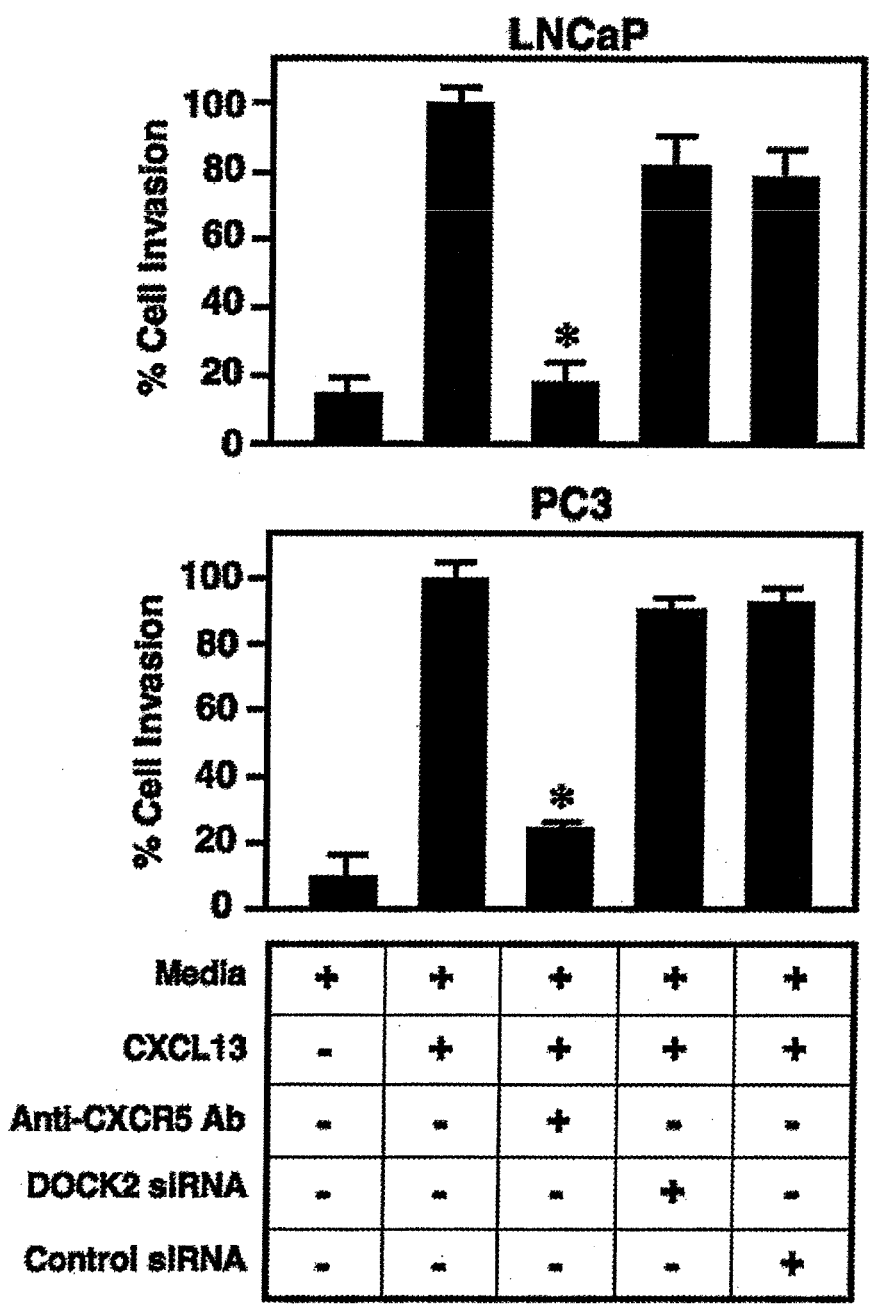
FIG. 2 shows that CXCL13:CXCR5 interaction promotes LNCaP and PC3 cell invasion independent of DOCK2.

While CXCL13:CXCR5 interaction is known to mediate DOCK2-dependent chemotaxis of neutrophils, it was also found that CXCL13:CXCR5 interaction is also capable of promoting cancer cell metastasis and invasion independent of DOCK2. In FIG. 2, LNCaP and PC3 cells were tested for their ability to invade Matrigel™ Matrix and migrate through an 8.0 µm porous membrane in the presence of CXCL13 (100 ng/ml), anti-human CXCR5 antibody (1 µg/ml), DOCK2 or control siRNA. Cells which invaded to the lower surface of the membrane were stained with crystal violet and counted by microscopy at 40× magnification. Percent cell invasion was calculated following manufacturer's instructions (BD Biosciences). Error bars represent standard error of means of 3 independent experiments. Asterisks (*) indicate significant differences (p<0.05) relative to CXCL13-treated cells (control).

Figure 3:
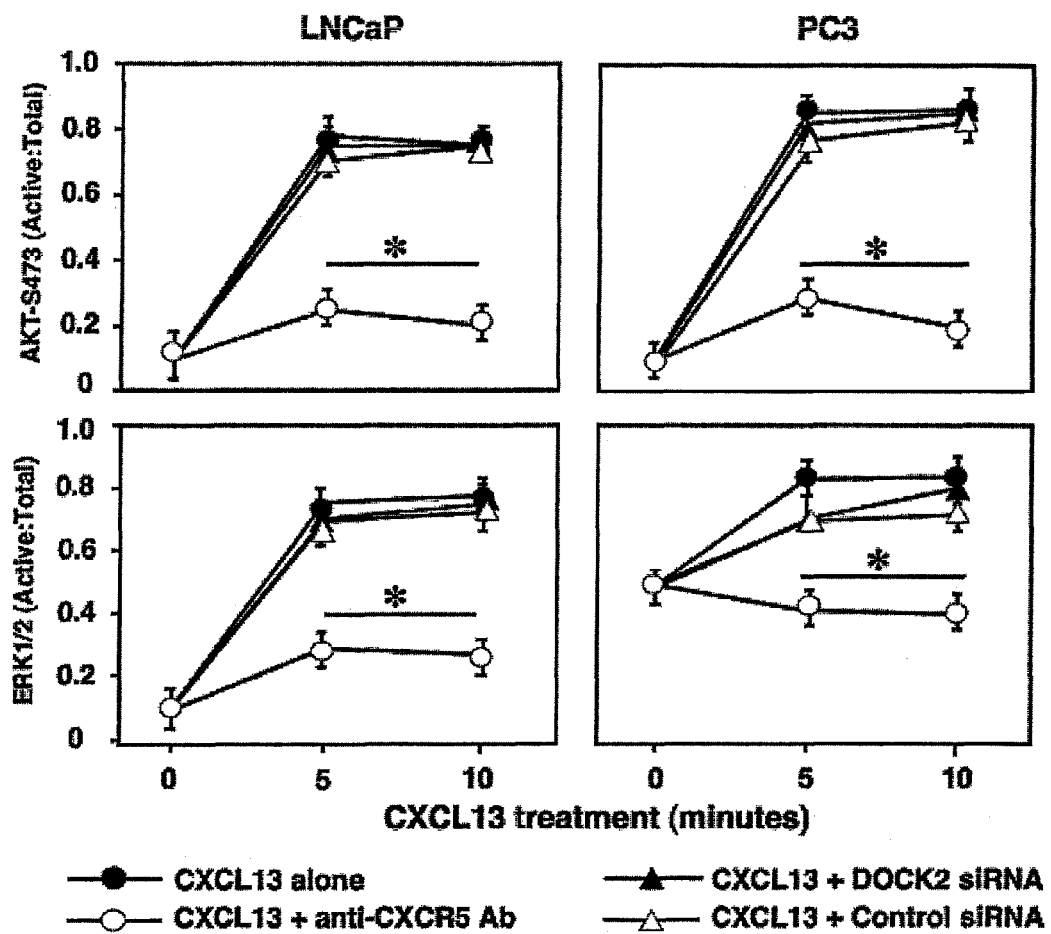
FIG. 3 shows CXCL13 regulation of Akt and ERK1/2 activation.

CXCL13 also regulates activation of Akt and ERK1/2, as shown in FIG. 3. FACE assays were performed to measure active and total Akt or ERK1/2 in LNCaP and PC3 cell lines. Cells were treated with anti-human CXCR5 antibody, DOCK2 siRNA, Control siRNA, or JNK inhibitor in the presence of CXCL13 (100 ng/ml) for 0, 5 or 10 minutes. Experiments were performed in triplicate and results show the ratio of active (phosphorylated) to total Akt or ERK1/2. Error bars represent ±standard error of means of 3 independent experiments. Asterisks (*) indicate significant (p<0.05) decrease in phosphorylation.

Figure 4:
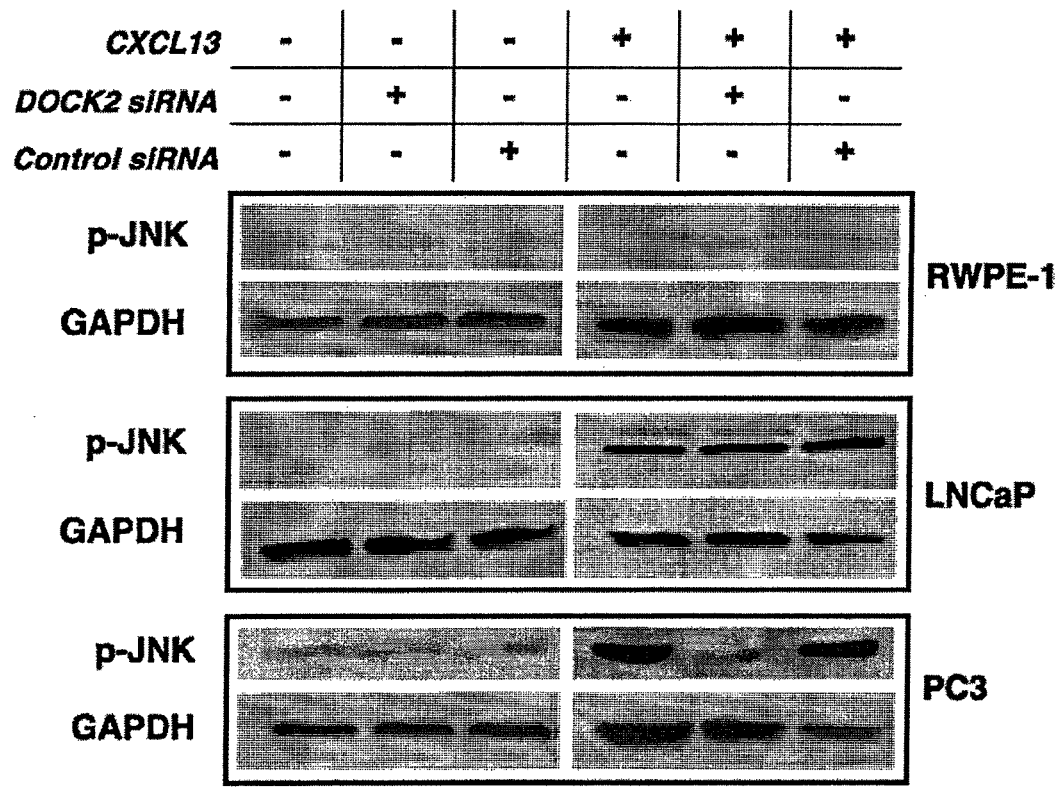
FIG. 4 shows that CXCL13 induces JNK activation through DOCK2 in PC3 cells.

FIG. 4 shows that CXCL13 induces JNK activation through DOCK2 in PC3 cells. RWPE-1, LNCaP, and PC3 cells were treated with DOCK2 siRNA and corresponding control in the presence or absence of CXCL13 (100 ng/ml). Lysates were collected 5 minutes following CXCL13 stimulation and samples were resolved on SDS-PAGE. Membranes were blotted for phospho-JNK (46 kDa). GAPDH serves as loading control.

Figure 5:
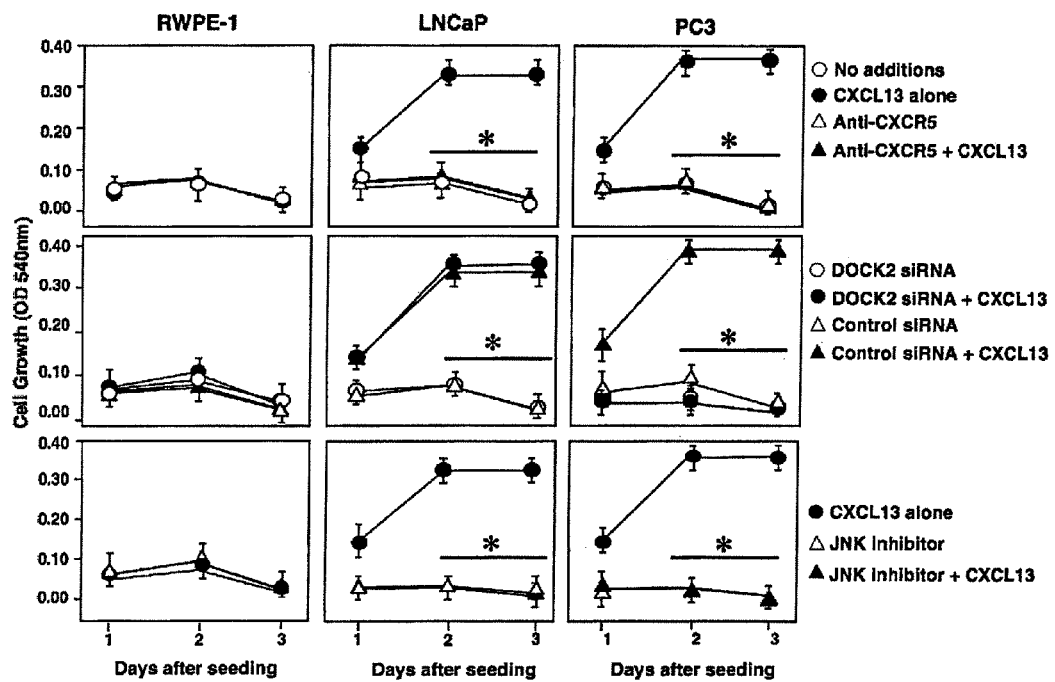
FIG. 5 shows CXCL13 regulation of prostate cancer (PCa) cell proliferation through JNK and DOCK2.

In FIG. 5, it is shown that CXCL13 regulates prostate cancer (PCa) cell proliferation through JNK and DOCK2. RWPE-1, LNCaP, and PC3 cells were grown in reduced serum conditions (2% FBS) in the presence or absence of 100 ng/ml CXCL13, 1 µg/ml anti-CXCR5 antibody, DOCK2 siRNA, and/or 10 µM JNK inhibitor. MTT assay was done over 3 days to assess cell proliferation. Error bars represent ±standard error of means of 3 independent experiments. Asterisks (*) indicate significant (p<0.05) changes relative to CXCL13 treated cells.

Figure 6:
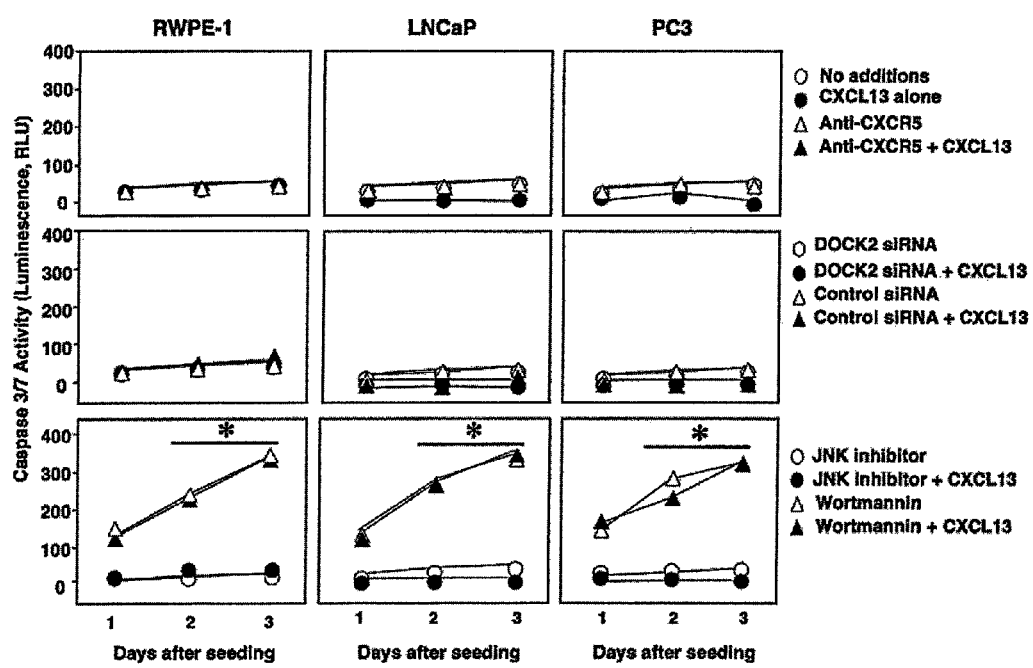
FIG. 6 shows that JNK inhibition and DOCK2 knockdown lead to reduction of PCa cell proliferation not due to cell death by apoptosis.

FIG. 6 shows JNK inhibition and DOCK2 knockdown lead to reduction of PCa cell proliferation that is not due to apoptosis. RWPE-1, LNCaP, and PC3 cells were grown in reduced serum conditions (2% FBS) in the presence or absence of 100 ng/ml CXCL13, 1 µg/ml anti-CXCR5 antibody, DOCK2 siRNA, 10 µM JNK inhibitor, or 1 µM Wortmannin. Caspase activity was measured using the CASPASE-GLO 3/7 Assay (Promega, Madison, Wis.) according to the manufacturer's directions. Asterisks (*) indicate significant (p<0.05) changes relative to no additions.

Figure 7:
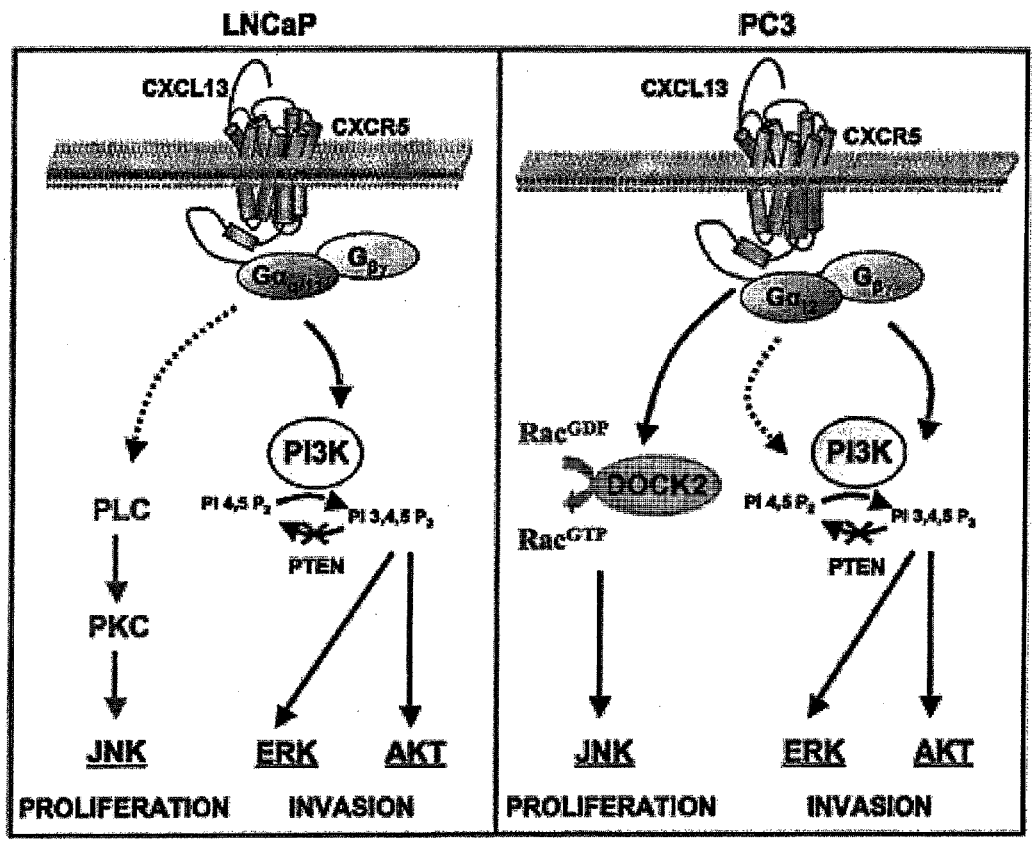
FIG. 7 shows CXCL13 modulation of signaling cascades in PCa cell lines.

FIG. 7 shows CXCL13 modulation of signaling cascades in PCa cell lines. CXCL13 through its cognate receptor CXCR5 elicits Akt and ERK1/2 activation. In LNCaP cells CXCL13 also regulates JNK activation, presumably via $G_{\alpha q/11}$ coupled to CXCR5, which mediates activation of phospholipase C (PLC) and protein kinase C (PKC). In PC3 cells, however, JNK activation is mediated through DOCK2.

Figure 8:
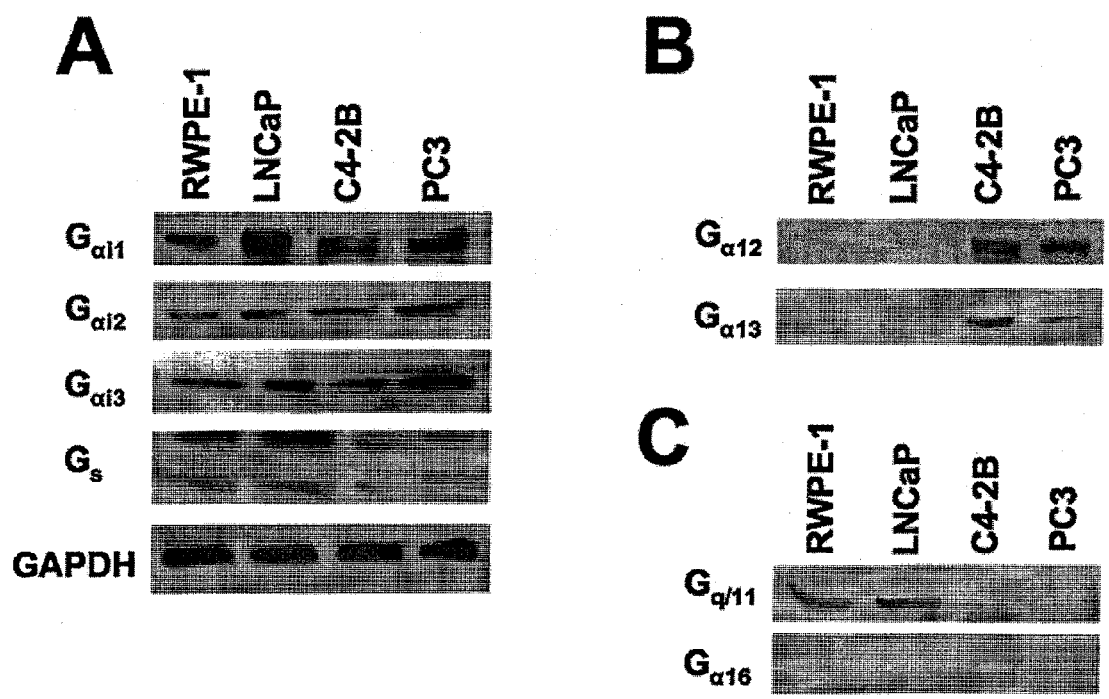
FIGS. 8A-C show the expression of α subunit isoforms of G-protein by prostate cancer cell lines.

FIGS. 8A-C demonstrate the expression of G-protein α subunit isoforms in prostate cancer cell lines. Equal amounts of protein (50 µg) from RWPE-1, LNCaP, C4-2B, and PC3 cells were resolved by SDS-Page. Expression of (A) $G_{\alpha i1,2,3}$, $G_{\alpha s}$; (B) $G_{\alpha 12}$, $G_{\alpha 13}$ and (C) $G_{\alpha q/11}$ and $G_{\alpha 16}$ were determined by immunoblot. GAPDH served as a loading control.

Figure 9:
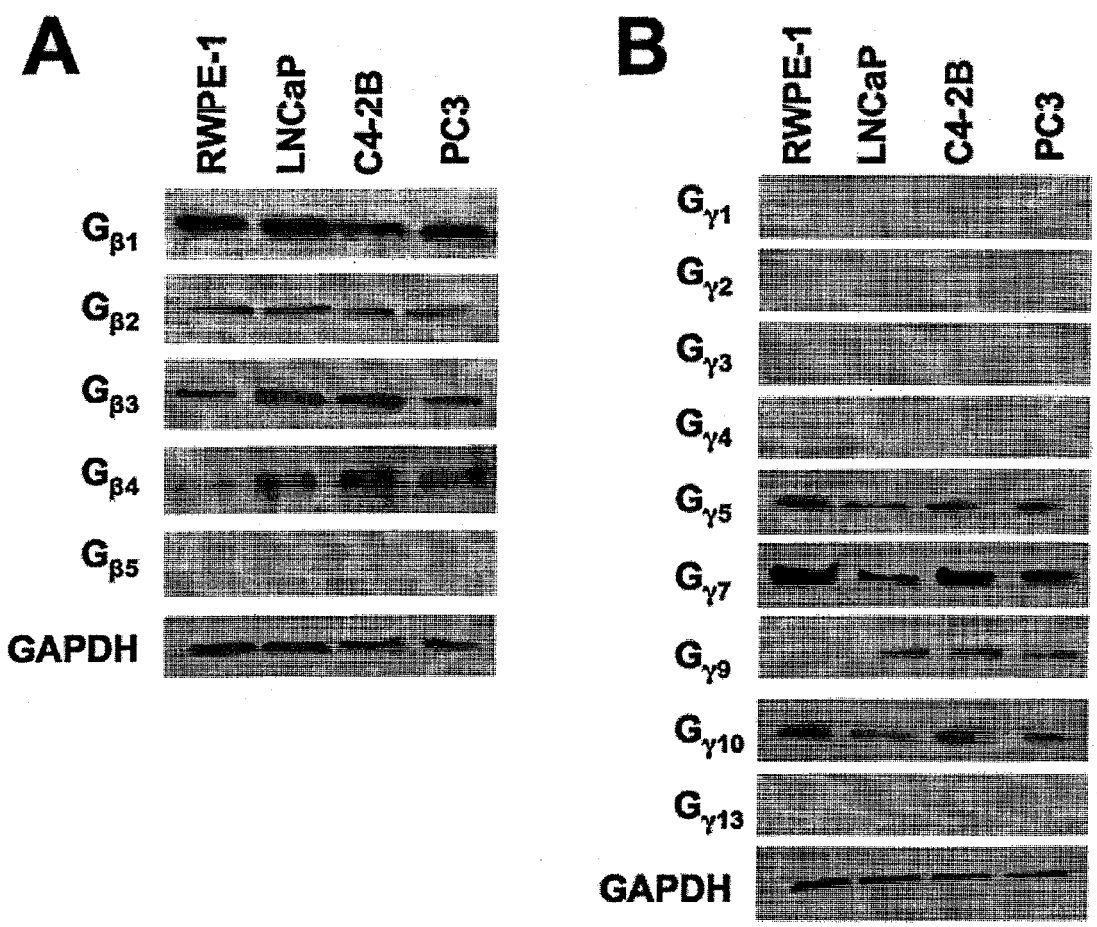
FIGS. 9A-B show G-protein β and γ subunit isoform expression of by prostate cancer cell lines.

FIGS. 9A-B demonstrates the expression of G-protein β and γ subunit isoforms in prostate cancer cell lines. Equal amounts of protein (50 µg) from RWPE-1, LNCaP, C4-2B, and PC3 cells were resolved by SDS-Page. Expression of $G_{\beta 1,2,3,4,5}$ and $G_{\gamma 1,2,3,4,5,7,9,10,13}$ were determined by immunoblot. GAPDH served as a loading control.

Figure 10:
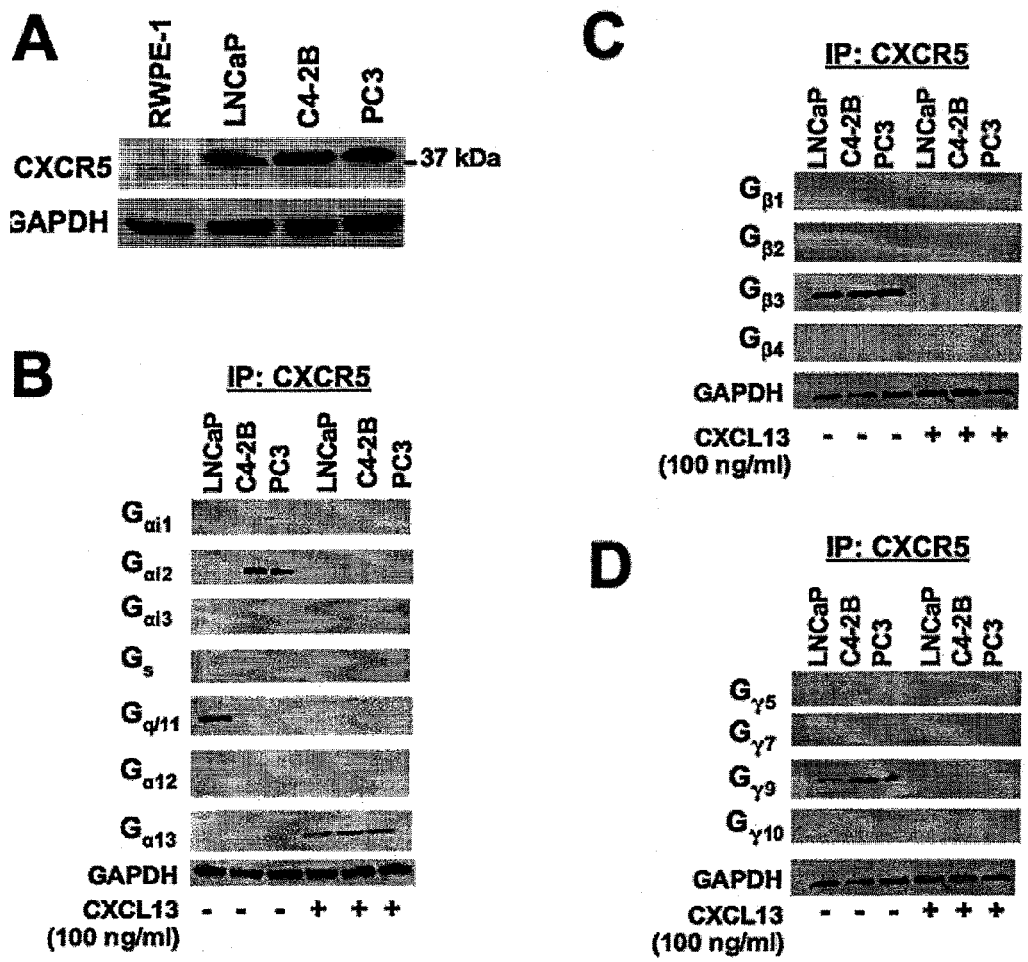
FIGS. 10A-D show expression of CXCR5 and associated G proteins in prostate cancer cell lines treated with or without CXCL13.

FIGS. 10 A-C show expression of CXCR5 and associated G proteins in prostate cancer cell lines treated with or without CXCL13. (A) C) CXCR5 protein levels were analyzed by Western blot of RWPE-1, LNCaP, C4-2B, and PC3 cell lysates (50 Ng). GAPDH served as loading control. (B) Cell lines were treated with or without CXCL13 and lysed. CXCR5 was immuno-precipitated (IP) to pull down associated proteins from total cell lysates. The IP cell lysates were resolved by SDS-PAGE and the expression of (B) $G_{\alpha i1}$, $G_{\alpha i2}$, $G_{\alpha 13}$, $G_{\alpha s}$, $G_{\alpha q/11}$, $G_{\alpha 12}$, $G_{\alpha 13}$, (C) $G_{\beta 1}$, $G_{\beta 2}$, $G_{\beta 3}$, $G_{\beta 4}$, and (D) $G_{\gamma 5}$, $G_{\gamma 7}$, $G_{\gamma 9}$, $G_{\gamma 10}$ were examined by immunoblot.

Figure 11:
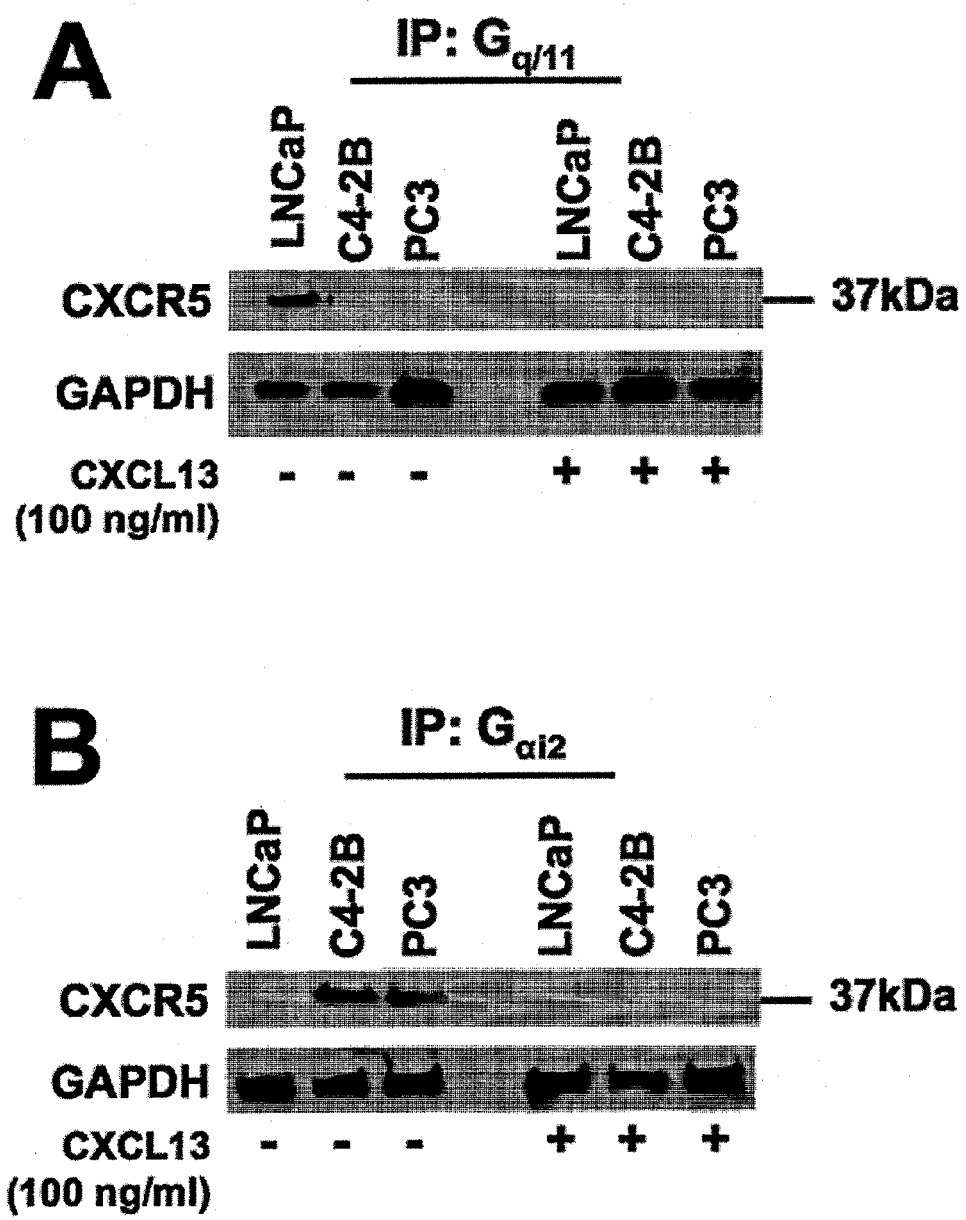
FIGS. 11A-B depict validation of Gq/11 and Gαi2 protein association with CXCR5 by immunoprecipitation.

The validation of $G_{q/11}$ and $G_{\alpha i2}$ protein association with CXCR5 by immunoprecipitation is shown in FIGS. 11A-B. Cell lines were treated with or without CXCL13 and lysed (A) $G_{\alpha q/11}$ and (B) $G_{\alpha i2}$ were immunoprecipitated (IP) from total cell lysates. The IP cell lysates were resolved by SDS-PAGE and CXCR5 expression was examined by immunoblot.

Figure 12:
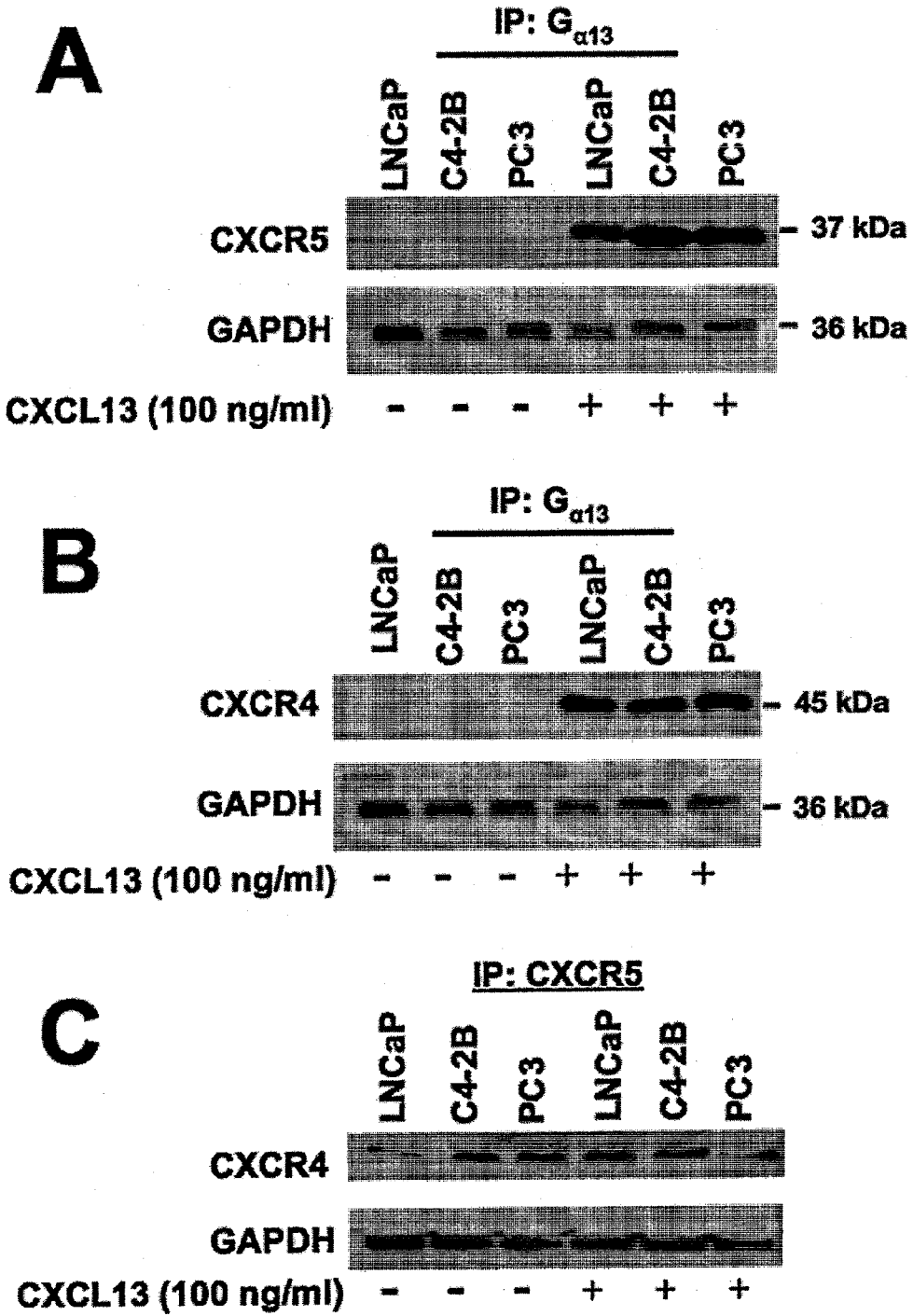
FIGS. 12A-C show the identification of CXCR4 and CXCR5 coupled to Gα13 following CXCL13 stimulation.

Identification of CXCR4 and CXCR5 coupled to Gα13 following CXCL13 stimulation is shown in FIGS. 12A-C. Cell lines were treated with or without CXCL13 and lysed. Antibody against Gα13 was used to immunoprecipitate (IP) it from total cell lysates. The IP cell lysates were resolved by SDS PAGE and immunoblotted for (FIG. 12A) CXCR5 and (FIG. 12B) CXCR4. (FIG. 12C) Western blot analysis of CXCR4 expression was also performed for CXCR5 IP lysates before and after CXCL13 treatment. GAPDH served as a loading control.

Figure 13:
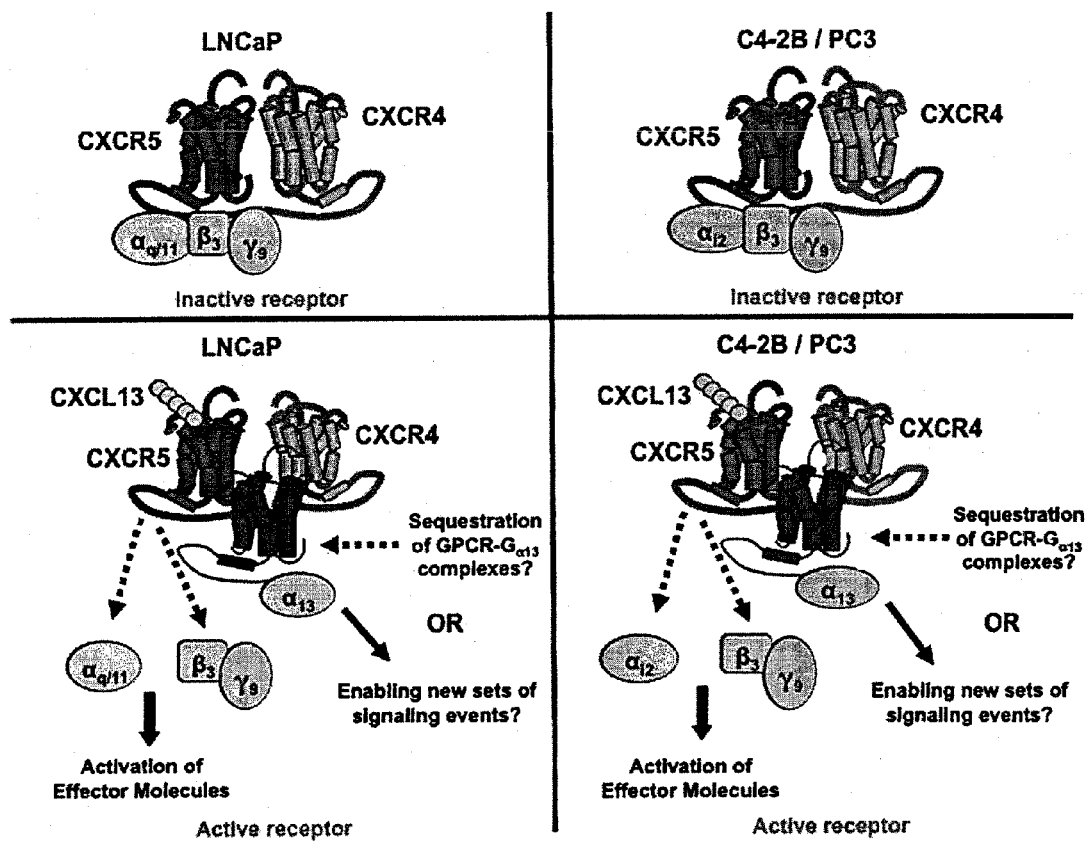
FIG. 13 depicts a hypothetical model of CXCR5 interactions in prostate cancer cells.

FIG. 13 depicts a hypothetical model of CXCR5 interactions in prostate cancer cells. CXCR5 associates with CXCR4 and couples with $G_{\alpha q/11}/G_{\beta 3}/G_{\gamma 9}$ heterotrimers in androgen-dependent LNCaP cell lines or $G_{\alpha i2}/G_{\beta 3}/G_{\gamma 9}$ heterotrimers in hormone refractory C4-2B and PC3 cell lines in the absence of its specific ligand, CXCL13. Upon CXCL13 stimulation, G-proteins dissociate from CXCR5 to activate effector molecules. In addition, CXCL13-activated CXCR5 causes, associates or sequesters $G_{\alpha 13}$ protein favoring signals that would promote PCa cell motility.

Table 1 shows the different networks that are affected by anti-CXCL13 and/or anti-CXCR5 treatment of prostate cancer cells, and the functions in prostate cancer cells that each of those networks is involved in. Score indicates the number of molecules known to participate in each respective network. Focus molecules (indicated by underline) are those molecules of particular interest or importance in each network.

TABLE 1

Highest scoring networks involved in CXCL13-treated metastatic prostate cancer

| Network ID | Molecules in Network (Focus Molecules in Bold) | Score | # of Focus Molecules | Top Functions |
|---|---|---|---|---|
| 1 | AKT1, AKT2, RTK, AMPK, ATM/ATR, BRCA1, CDC2, CDC25A, CDC25B/C, CDC25C, CDK2, CDKN1B, CHEK1, CHEK2, Cyclin A, Cyclin B, Cyclin D, Cyclin E, E2f, Fcer1, Foxo, Ige, Laminin, LIMK1, MAP2K2, MAP2K3, MEF2, Mek, Pkg, PRKAA1, RAF1, Rb, RB1, Scf, STMN1 | 31 | 19 | Cancer, Cell Cycle |
| 2 | Actin, α Actinin, βArrestin, Calpain, CAV1, CFL1, Cofilin, Collagen(s), CTTN, Dynamin, Erm, EZR, F Actin, FAK-Src, FCGR1A/2A/3A, G3BP1, Integrin αVβ3, KRT18, MAP2K1/2, NF2, NTRK2, Pak, phosphatase, PTEN, PTK2, PXN, Rac, Ras homolog, Rock, SRC, Talin, VASP | 26 | 20 | Cellular Movement, Cell Morphology |
| 3 | AKT1, ALP, Calmodulin, CaMKII, Caspase, CDKN1A, Ck2, Creb, CREB1, CTNNB1, Cytochrome c, ERBB2, ESR1, FSH, GLRX2, HDAC8, Histone h3, Histone h4, Hsp70, HSP84-2, HSP90AB1, ICAM1, JUN, Nfat, PDPK1, Pp2b, Proteasome, RNA polymerase II, Rxr, Smad, SYN1, TFIIH, Tubulin, YWHAZ | 21 | 14 | Cancer, Reproductive System Disease |

Table 2 shows the proteins that have been found to be regulated by CXCL13 and CXCR5 in prostate cancer cells. The molecules are arranged according to the particular biological functions they are associated with in the cells and the functions or diseases for which their increased expression in the cells can be used as a marker.

TABLE 2

Proteins regulated by CXCL13 and their relevant biological functions in PC3 cells

| Biological functions and diseases | Molecules | P-value |
|---|---|---|
| Growth of tumor cell lines | AKT1, AKT2, BAD, BCL2, BCL2L1, CAV1, CDC2, CDK2, ELK1, JUN, MAPK3, MAPK8, NF2, PTK2, RAF1, SRC, STMN1 | 1.11E−09 |
| Proliferation of tumor cell lines | AKT1, AKT2, BAD, CAV1, GJA1, ITGB3, JUN, JUNB, LIMK1, MAPK3, MAPK8, PDPK1, SRC | 6.66E−08 |
| Anti-Apoptosis | AKT1, AKT2, BAD, BCL2, BCL2L1, CAV1, CDC2, ITGB3, JUN, MAPK3, MAPK8, PDPK1, PTK2, SRC, STMN1, VAV1 | 4.26E−07 |
| Prostate carcinoma | AKT1, AKT2, CDC2, CDK2, ITGB3, JUN, RAF2, SRC | 9.16E−07 |
| Metastasis | AKT1, ITGB1, NF2, PTK2, RELA, SRC | 9.29E−07 |
| Cell cycle progression | BCL2, CAV1, CDC25C, CDK2, MAPK8, RAF1, VAV1 | 1.85E−05 |
| Survival of tumor cell lines | AKT1, AKT2, BCL2, BCL2L1, CAV1, CDK2, CDKN1A, CDKN1B, CHEK1, CHEK2, CREB1, EGFR, ERBB2, FRAP1, JAK1, MET, NFKB1, NFKB2, NTRK2, PDGFRB, PRKAA1, PTK2, RELA, RELB, SRC, STAT3 | 2.05E−05 |

Figure 14:
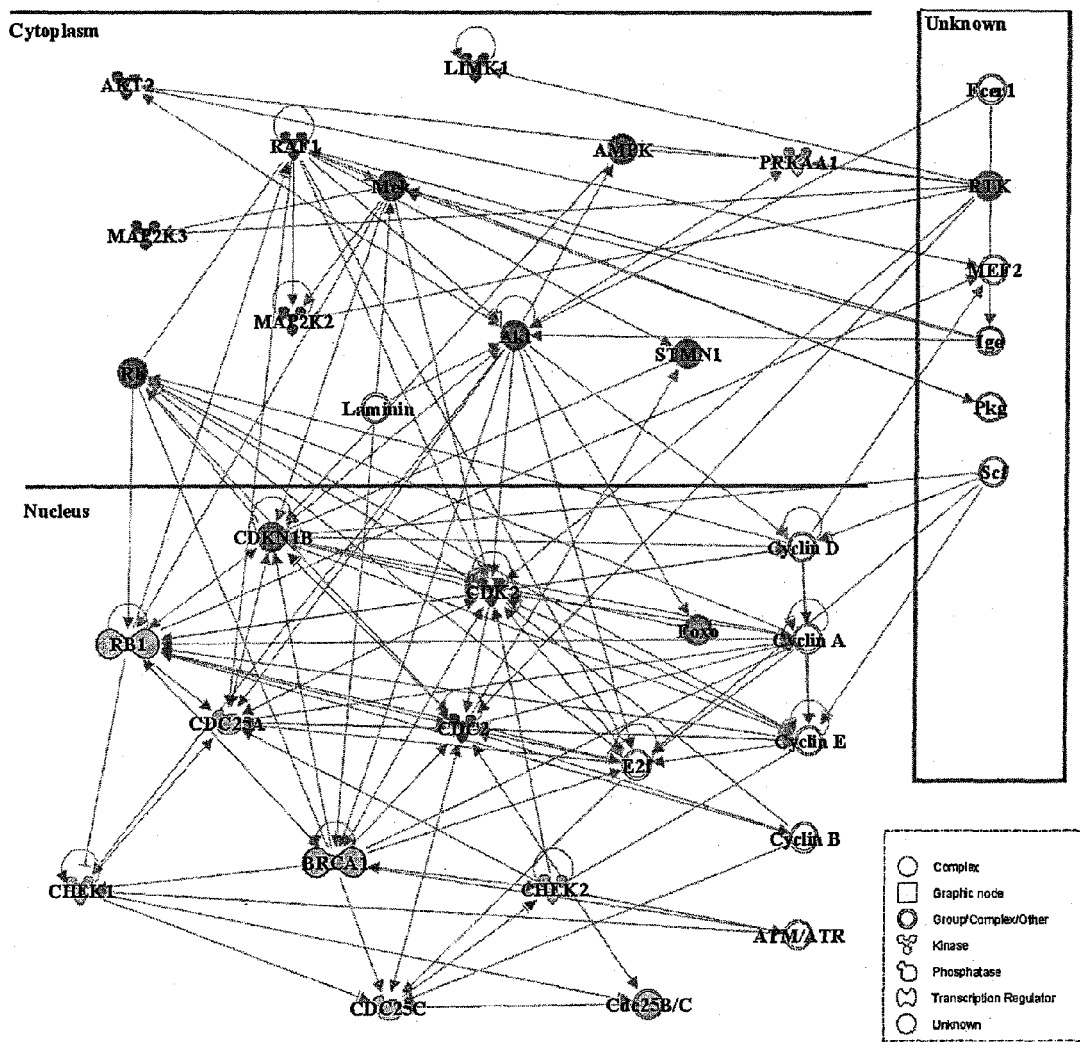
FIG. 14 depicts how CXCL13 regulates key molecules involved in the cell cycle.

FIG. 14 depicts how CXCL13 regulates key molecules involved in cell cycle. Phospho-specific antibody microarrays were separately hybridized with CXCL13-treated or untreated PC3 cell lysates. Ratios of phosphorylated to unphosphorylated molecules were calculated and the datasets uploaded into the Ingenuity Pathways Analysis application. Networks were algorithmically generated based on molecules' connectivity. Results were normalized to GAPDH levels. Colors represent fold changes in phosphorylation. Gray indicates no change in phosphorylation status, green indicates decreased phosphorylation, pink indicates baseline phosphorylation, and red indicates increased phosphorylation relative to baseline.

Figure 15:
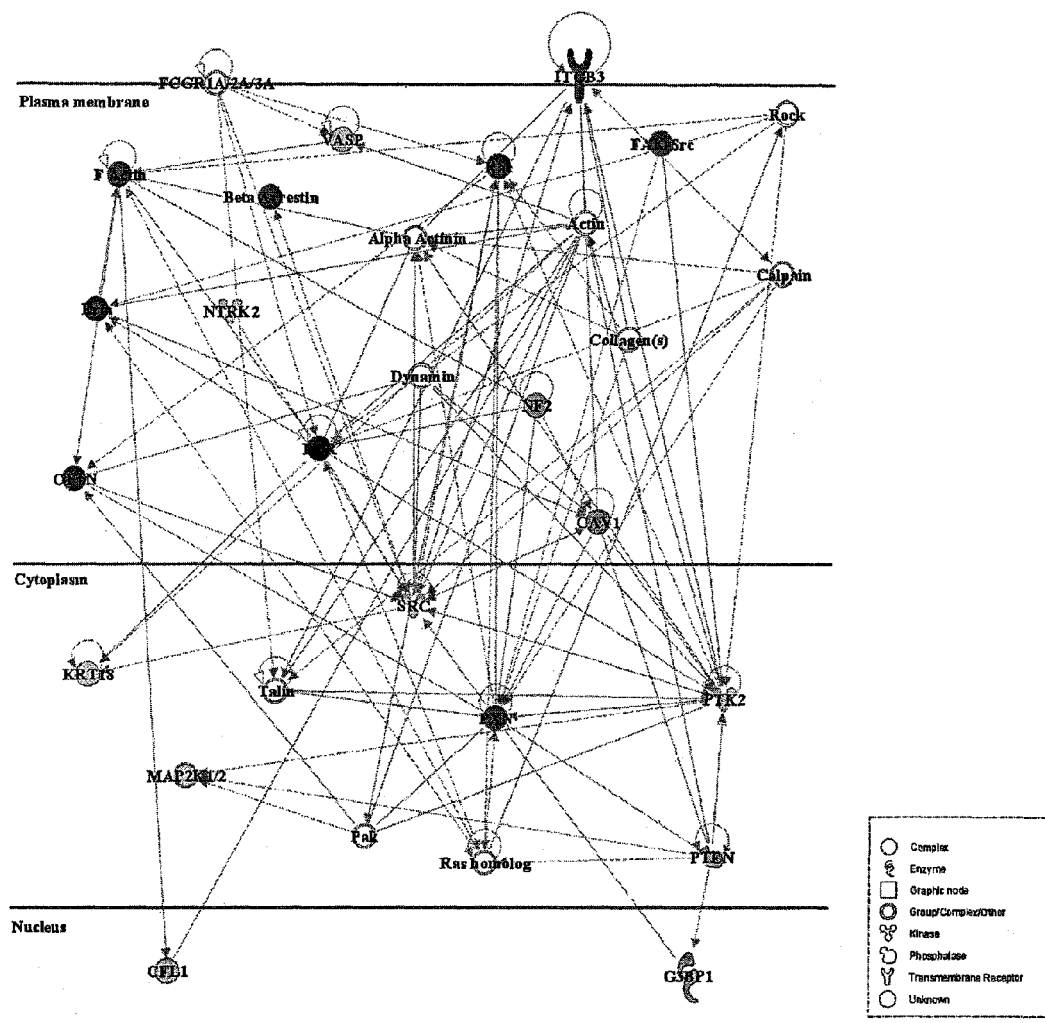
FIG. 15 depicts how CXCL13 regulates key molecules involved in cell migration.

FIG. 15 depicts how CXCL13 regulates key molecules involved in cell migration. Phospho-specific antibody microarrays were separately hybridized with CXCL13-treated or untreated PC3 cell lysates. Ratios of phosphorylated to unphosphorylated molecules were calculated and the datasets uploaded into the Ingenuity Pathways Analysis application. Networks were algorithmically generated based on molecules' connectivity. Results were normalized to GAPDH levels. Colors represent fold changes in phosphorylation. Gray indicates no change in phosphorylation status, green indicates decreased phosphorylation, pink indicates baseline phosphorylation, and red indicates increased phosphorylation relative to baseline.

Figure 16:
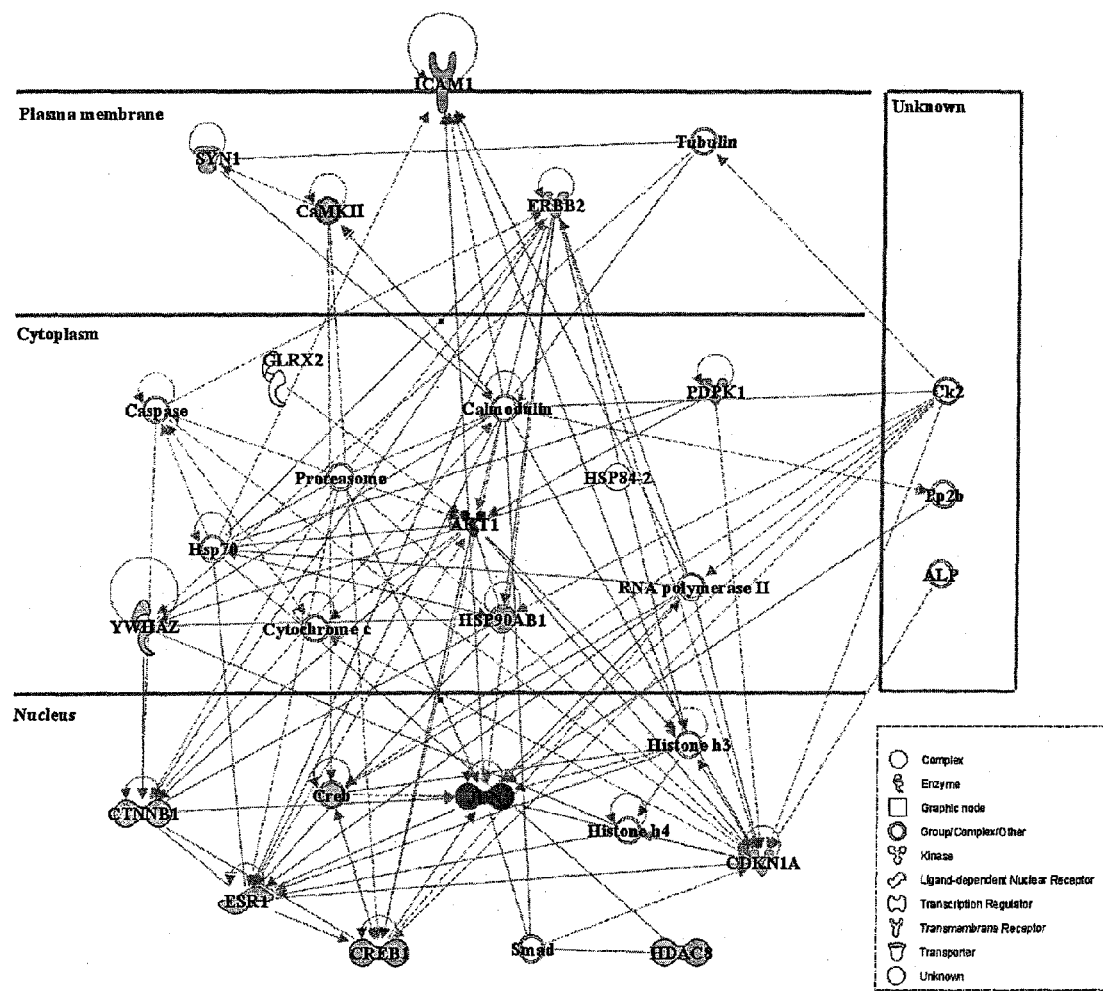
FIG. 16 depicts how CXCL13 regulates key molecules involved in cell survival and growth.

FIG. 16 depicts how CXCL13 regulates key molecules involved in cell survival and growth. Phospho-specific antibody microarrays were separately hybridized with CXCL13-treated or untreated PC3 cell lysates. Ratios of phosphorylated to unphosphorylated molecules were calculated and the datasets uploaded into the Ingenuity Pathways Analysis application. Networks were algorithmically generated based on molecules' connectivity. Results were normalized to GAPDH levels. Colors represent fold changes in phosphorylation. Gray indicates no change in phosphorylation status, green indicates decreased phosphorylation, pink indicates baseline phosphorylation, and red indicates increased phosphorylation relative to baseline.

Figure 17:
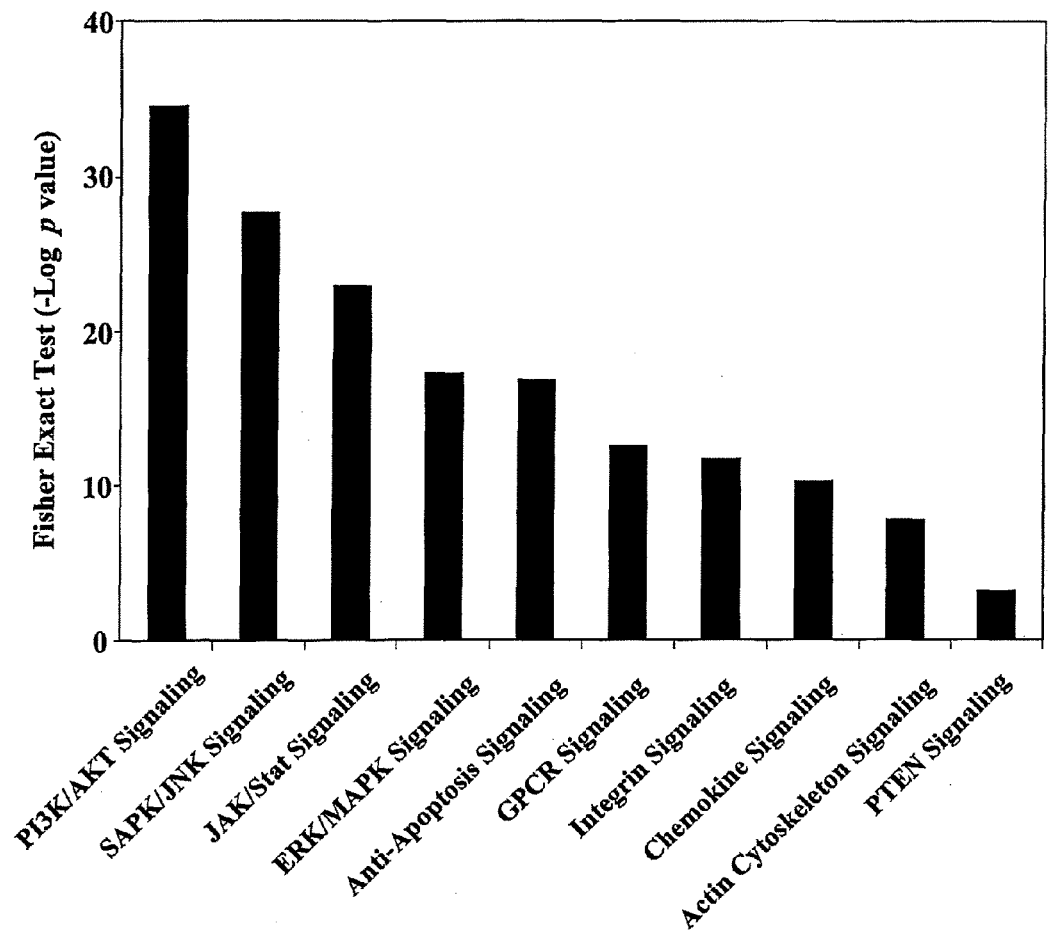
FIG. 17 depicts the top Canonical pathways regulated by CXCL13 in PC3 cells.

The top ten signaling pathways regulated by CXCL13 based on their significance (p-value) calculated using the right-tailed Fisher's Exact test using the entire dataset are shown in FIG. 17.

Figure 18:
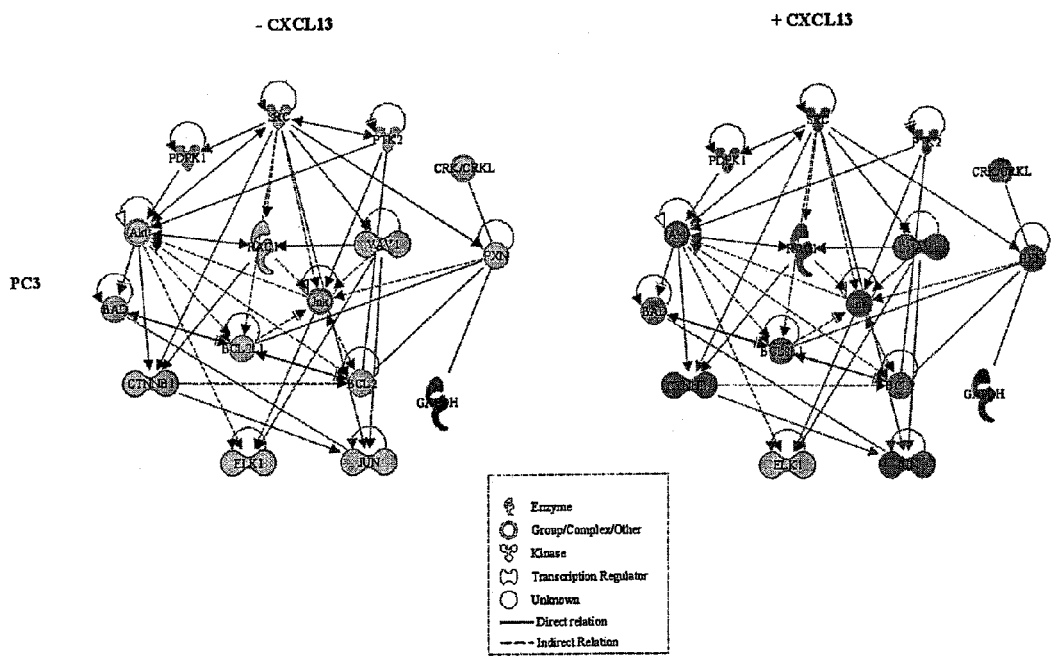
FIG. 18 shows CXCL13 mediation of differential phosphorylation of proteins belonging to the PI3K/Akt and SAPK/JNK signaling pathways.

It was found that CXCL13 mediates differential phosphorylation of proteins (colored molecules) belonging to the P13K/Akt and SAPK/JNK signaling pathways, as shown in FIG. 18. The two canonical pathways were merged and overlaid with the analyzed microarray data from CXCL13-treated or untreated PC3 cells. Gray indicates no change in phosphorylation status, green indicates decreased phosphorylation, pink indicates baseline phosphorylation, and red indicates increased phosphorylation relative to baseline.

Figure 19:
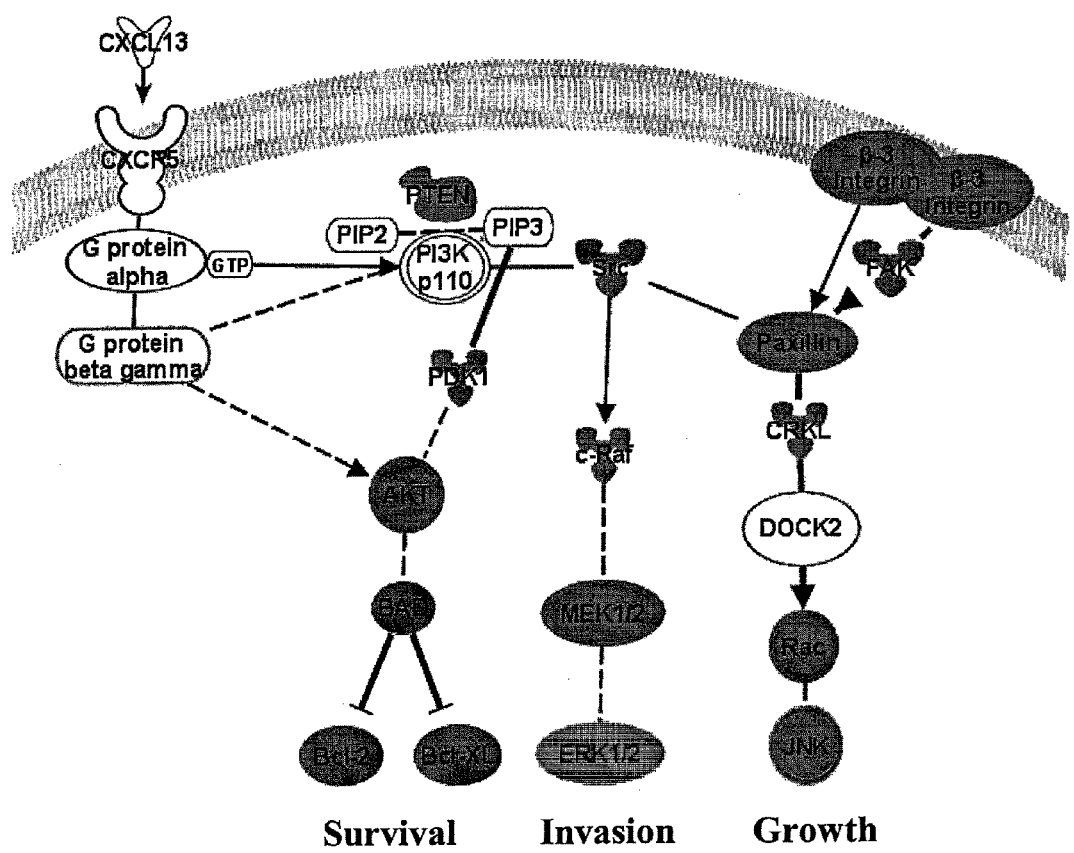
FIG. 19 is a summary diagram of signaling pathways modulated by CXCL13-CXCR5 interactions.

FIG. 19 summarizes the signaling pathways modulated by CXCL13:CXCR5 interactions. CXCL13 binding to CXCR5 results in the activation of PI3K/Akt, Raf/MEK/ERK, Integrin/33/Src/FAK, and DOCK2/Rac/JNK pathways involved in cell survival, invasion, and growth respectively.

Figure 20:
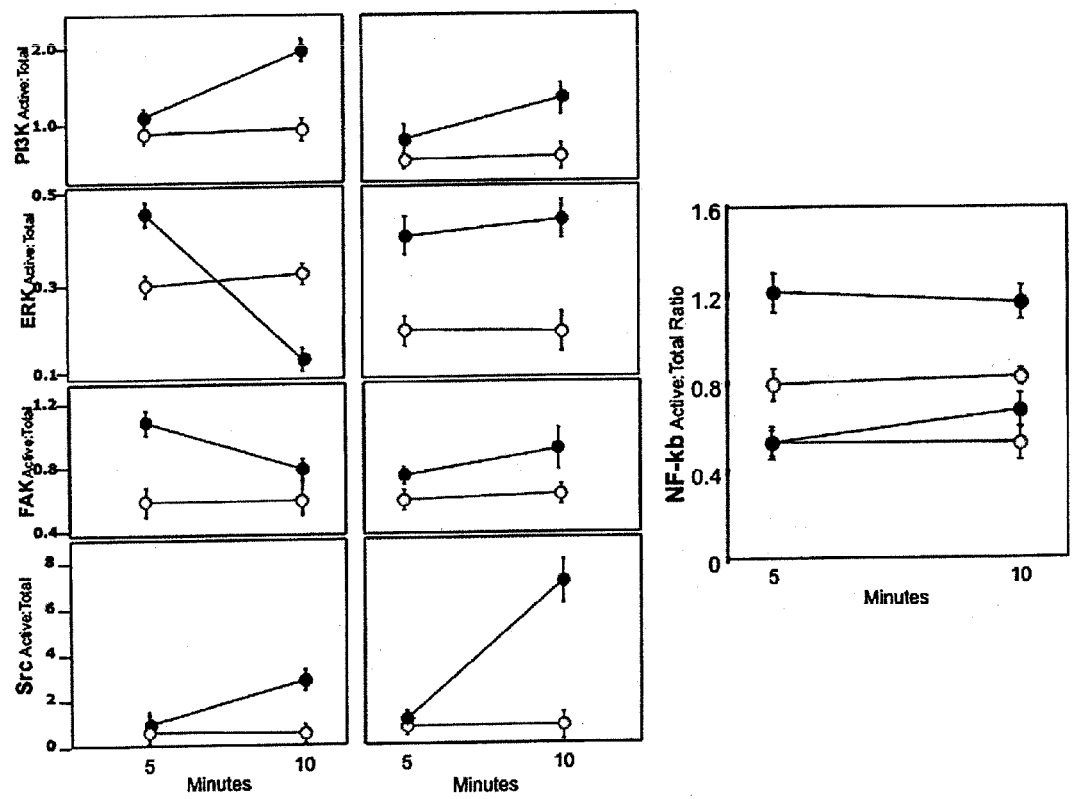
FIG. 20 shows confirmation of major CXCL13-CXCR5 cell signaling cascades.

A confirmation of major CXCL13-CXCR5 cell signaling cascades is shown in FIG. 20. LNCaP (blue circles) or PC3 (magenta circles) cells received no additions (open circles) or 100 ng/ml of CXCL13 (closed circles) for 5 or 10 minutes. FACE™ assays (Active Motif, Carlsbad, Calif.) were used to detect both active and inactive (total) P13K, ERK, FAK, Src kinase and NFkb proteins, 5 or 10 minutes after stimulation. Ratios of active (phosphorylated) to total proteins are presented ±SEM from 3 separate experiments performed in triplicate.

Figure 21:
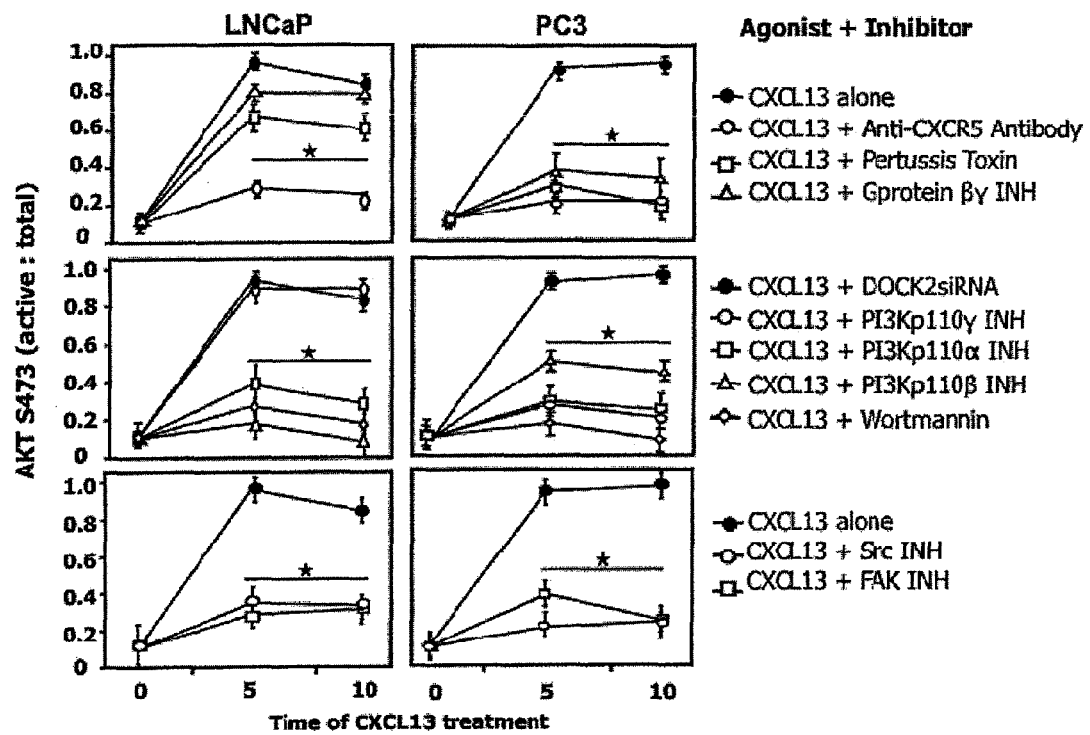
FIG. 21 shows CXCL13-CXCR5 signaling events required for AKT activation.

CXCL13-CXCR5 signaling events required for AKT activation are shown in FIG. 21. FACE assays were performed to measure active and total AKT levels in LNCaP and PC3 cell lines. Cells were treated with (or without) CXCL13 for 5 or 10 minutes, along with or without CXCR5 blockade, pertussis toxin, U-73122, wortmannin, PI-103, TGX221, and AS605240, DOCK2 siRNA, SU6656, and PF-573228. Experiments were performed in triplicate and results show the ratio of p-AKT to total AKT.

Figure 22A:
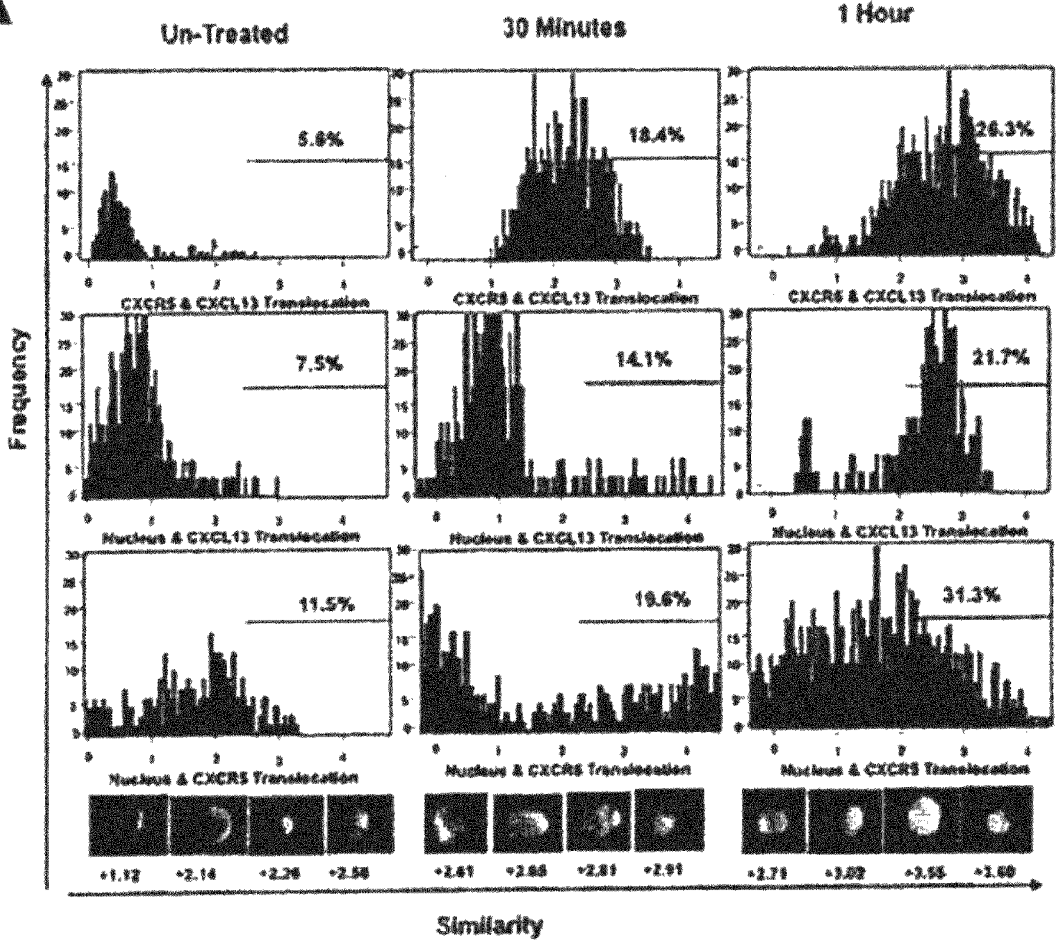
FIGS. 22A-B depicts CXCL13-mediated CXCR5 ligation and translocation to nuclei.
Figure 22B:
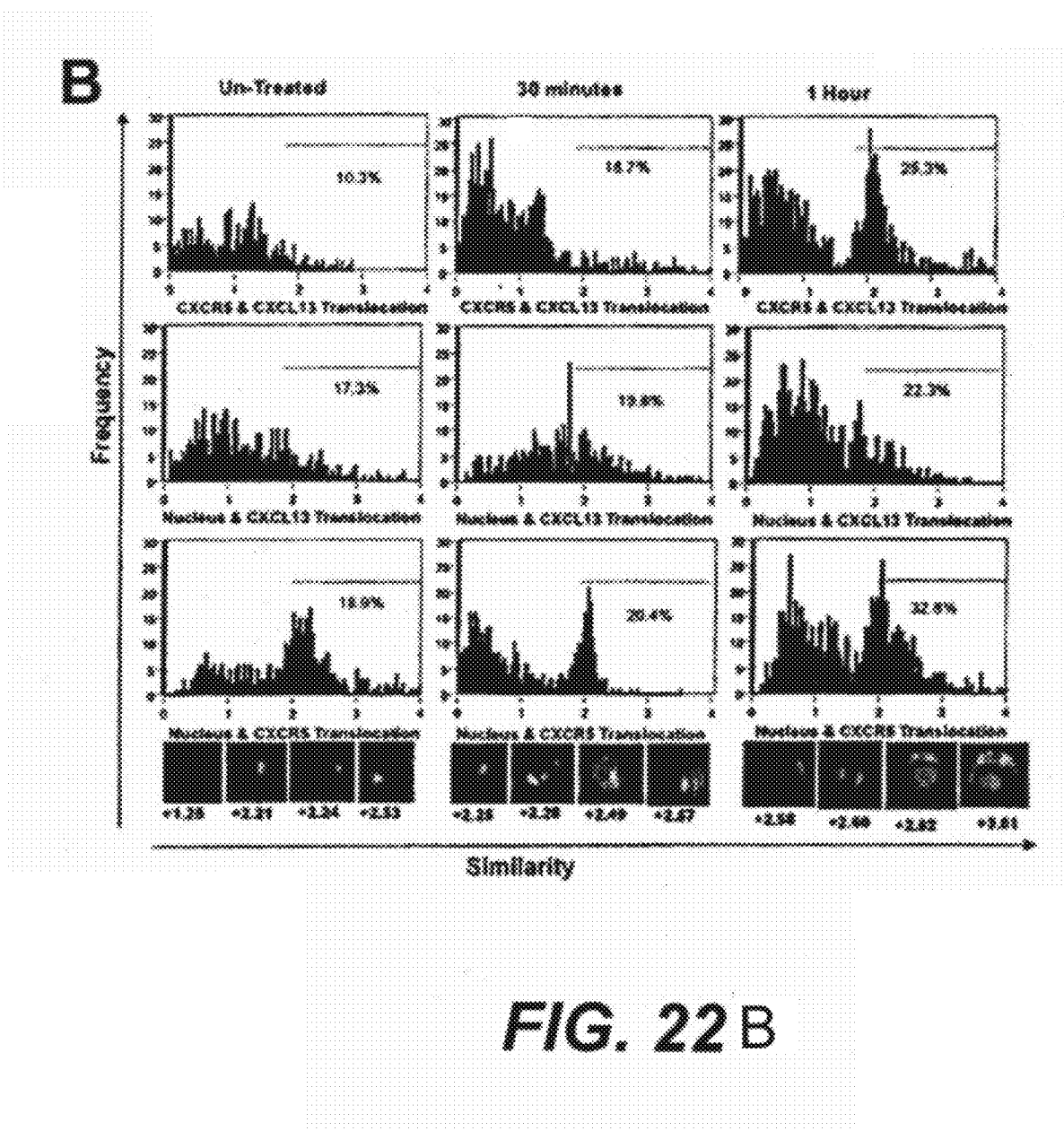

FIGS. 22A-B show CXCL13-mediated CXCR5 ligation and translocation to nuclei. LNCaP (FIG. 22A) and PC3 (FIG. 22B) cancer cell lines were stained with FITC (green)-conjugated anti-CXCR5 antibody, Alexa455 (orange)-conjugated anti-CXCL13 antibody and 7AAD (red) as a nuclear stain 30 and 60 minutes after treatment with 0 or 100 ng/ml of CXCL13. Histograms indicate the degree of signal correlation between CXCR5 and CXCL13 or these pairs with nuclei. The gate for positive population thresholds was determined by referencing dark field and 7AAD similarity scores with the Amnis Imagestream INSPIRE™ and IDEAS™ acquisition, and analysis software and system. The percentage of translocated cells are given above the 'Translocated' region bars.

Example 2

Anti-CXCL13 Antibody Treatment Inhibits Metastasis and Tumor Growth in Bone

Figure 23:
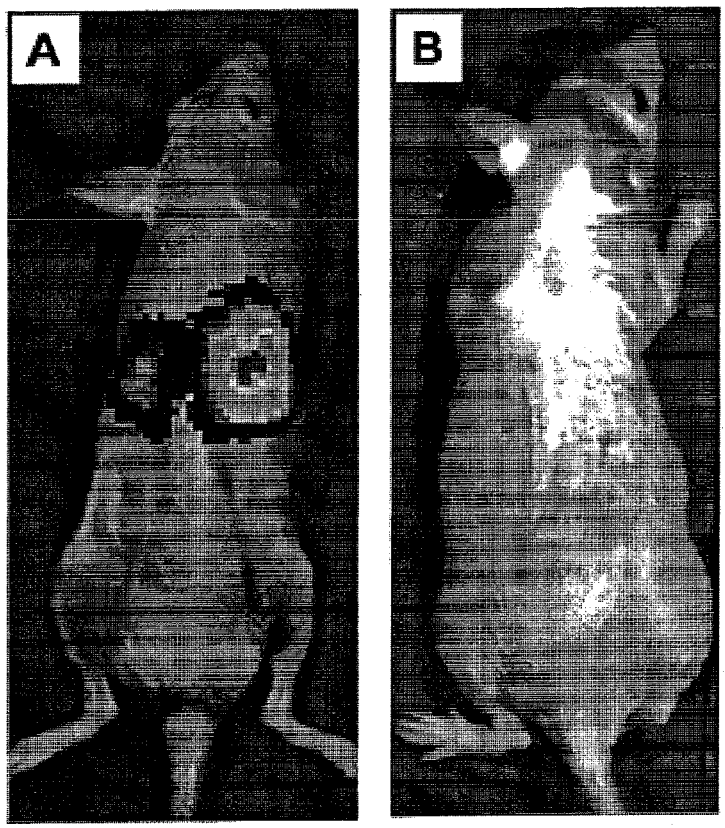
FIGS. 23A-B show that anti-CXCL13 antibody treatment inhibits prostate cancer progression and bone metastasis.

Anti-CXCL13 antibody treatment is shown in FIGS. 23A-B to inhibit prostate cancer progression and bone metastasis. Two groups of ten B6.Cg-Foxn-Nu/J male mice (ten-week old) were challenged with $10^6$ luciferase-positive PC3 cells in 50 µl of saline by intracardiac injection. Prostate tumors were allowed to develop over 30 days; afterwards groups received either 0.5 µg of control (FIG. 23A) or anti-CXCL13 (FIG. 23B) antibodies every three days for an additional 30 days. This representative image shows the changes in tumor burden and bone metastasis that was analyzed by in vivo imaging using a Caliper/Xenogen IVIS100 imaging system (Caliper, San Diego, Calif.).

Figure 24A:
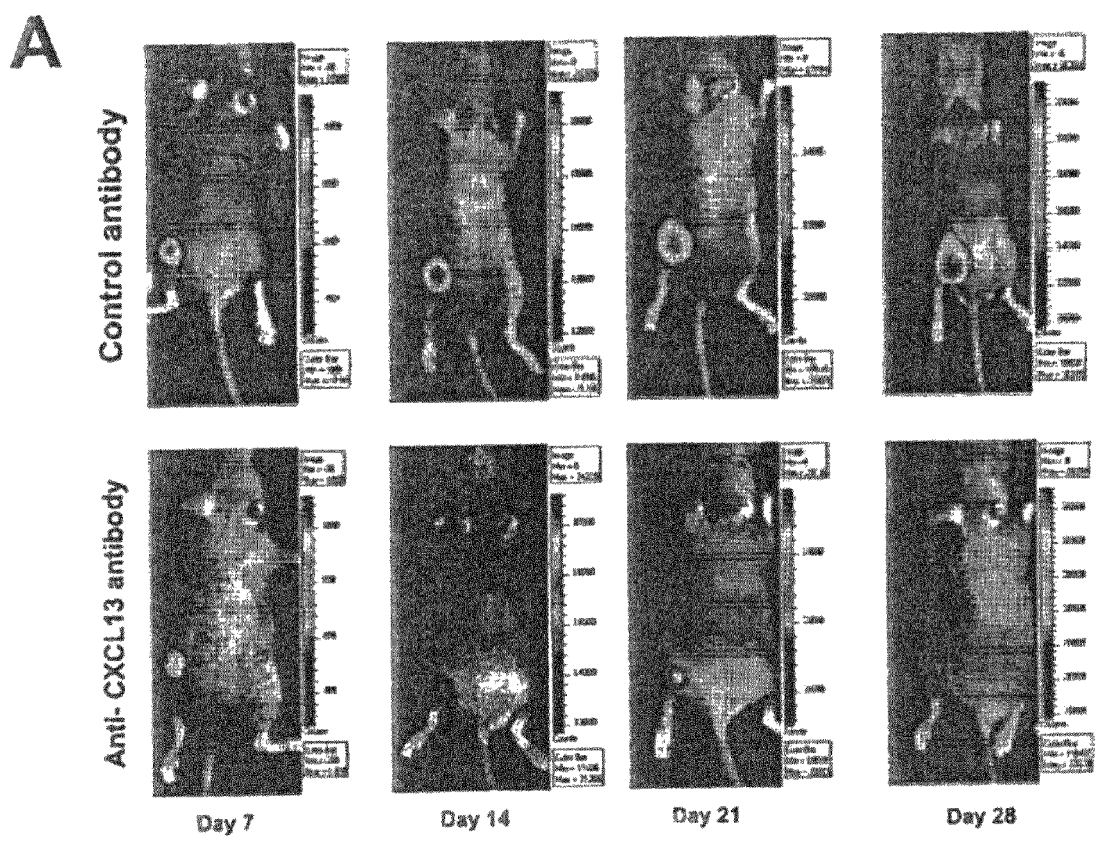
FIGS. 24A-B show that CXCL13 blockade inhibits prostate tumor growth in bone.
Figure 24B:
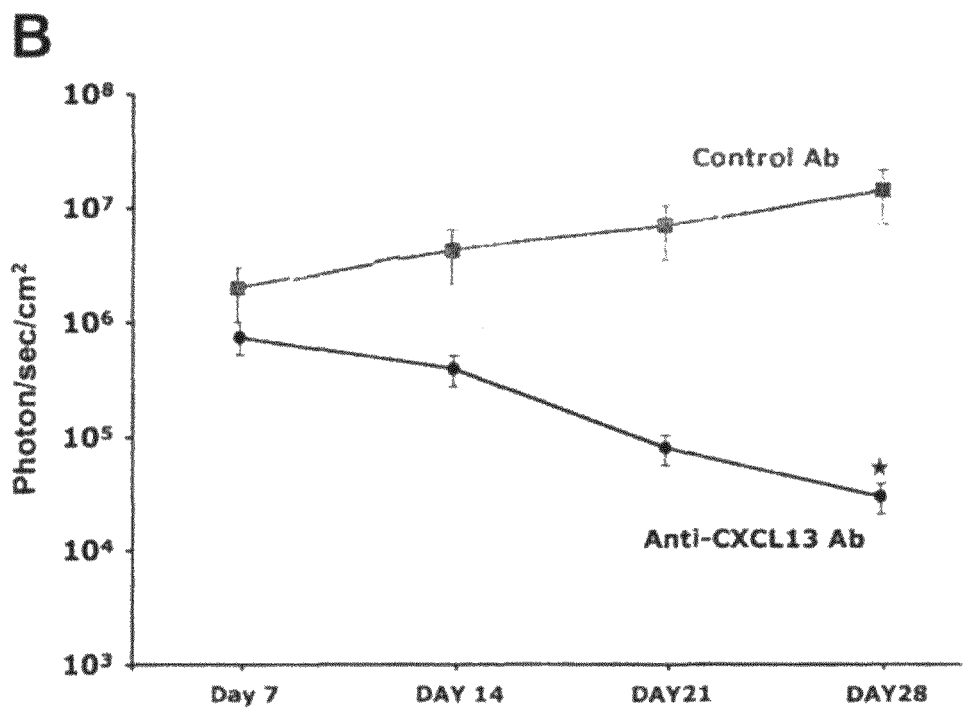

FIGS. 24A-B show that CXCL13 blockade inhibits prostate tumor growth in bone. Male Nu/Nu mice were intra-tibially injected with $10^6$ luciferase-positive PC3 (PC3-luc) cells and tumors were allowed to develop for one week. Subsequently, the mice were intraperitoneally injected with 475 µg/kg isotype control or anti-CXCL13 antibody suspended in 100 µl of sterile saline every 72 hours for one week. Experimental groups were imaged every week for four weeks using the Caliper/Xenogen In Vivo imaging system 100 and analyzed using the Caliper LIVING IMAGE® (Caliper, San Diego, Calif.) software. FIG. 24A displays representative images of PC3-luc tumor growth in bone. FIG. 24B shows luminescence (photons/sec/cm$^2$)±SEM of PC3-luc tumors in bone 7, 14, 21, and 28 days post challenge. Asterisk (*) indicates significant (p<0.01) differences between isotype control and anti-CXCL13 antibody-treated groups.

Figure 25:
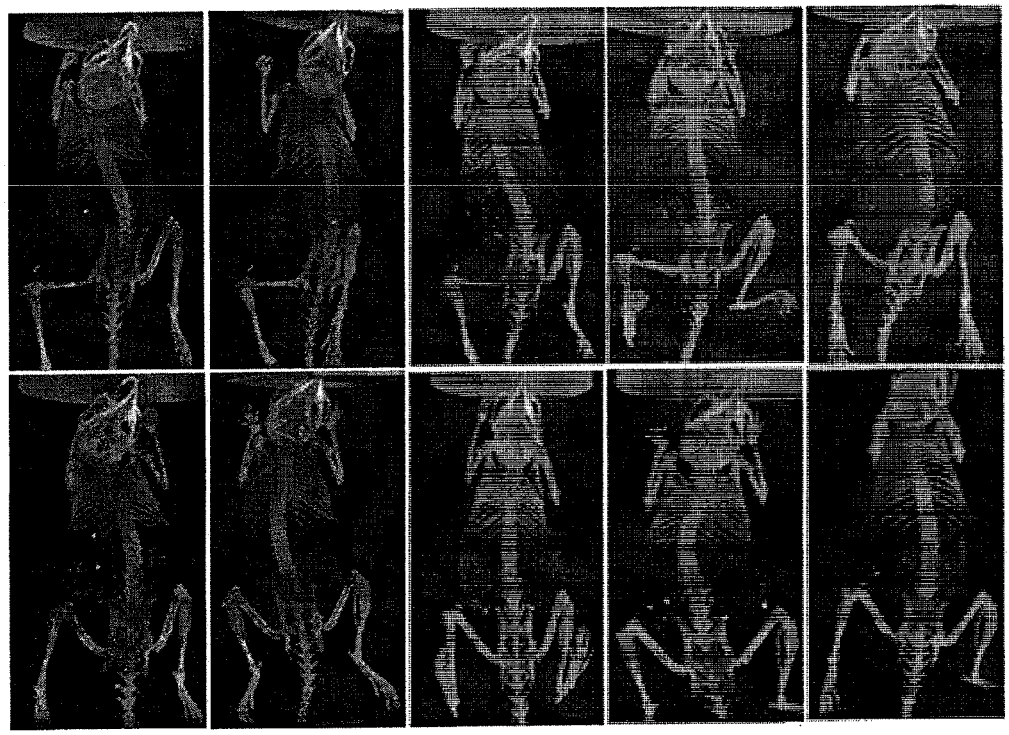
FIGS. 25A-B show that CXCL13 blockade abrogates osteolytic prostate tumor growth in bone.
Figure 25:
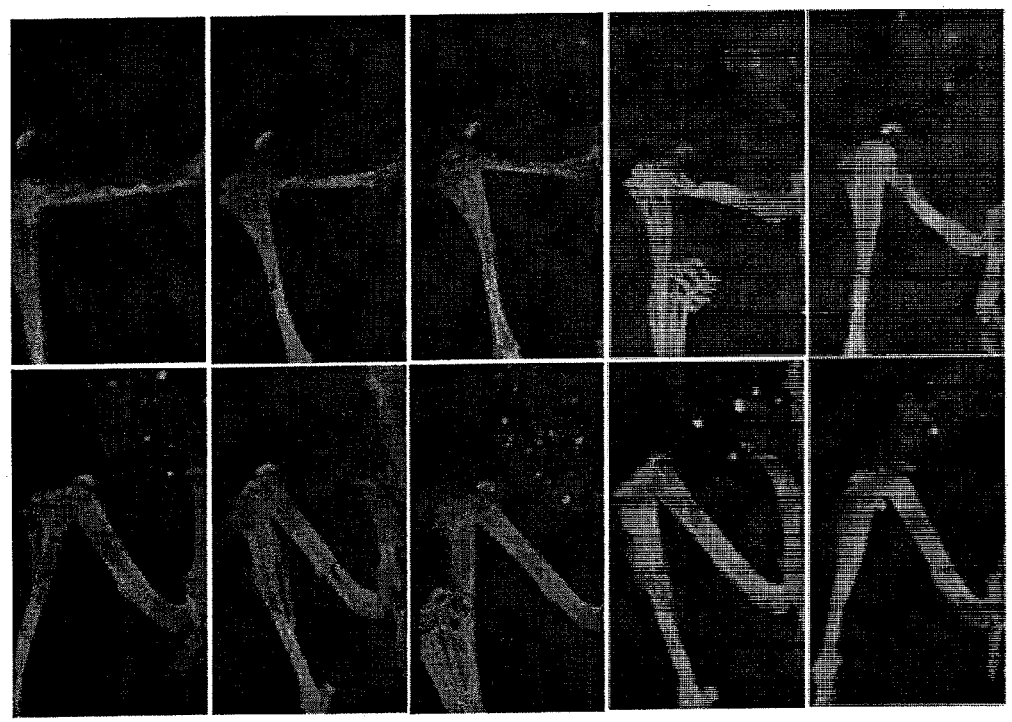

CXCL13 blockade also abrogates osteolytic prostate tumor growth in bone, as shown in FIGS. 25A-B. Male Nu/Nu mice were intra-tibially injected with $10^6$ luciferase-positive PC3 (PC3-luc) cells and tumors were allowed to develop for one week. Subsequently, mice were intraperitoneally injected with 475 µg/kg isotype control or anti-CXCL13 antibody suspended in 100 of sterile saline every 72 hours for one week. Experimental groups were imaged 28 days post challenge using a Siemens microCT Scan System. Low (FIG. 25A) and high FIG. 25B) resolution images from five mice in each group processed using OsiriX imaging software are shown.

Figure 26:
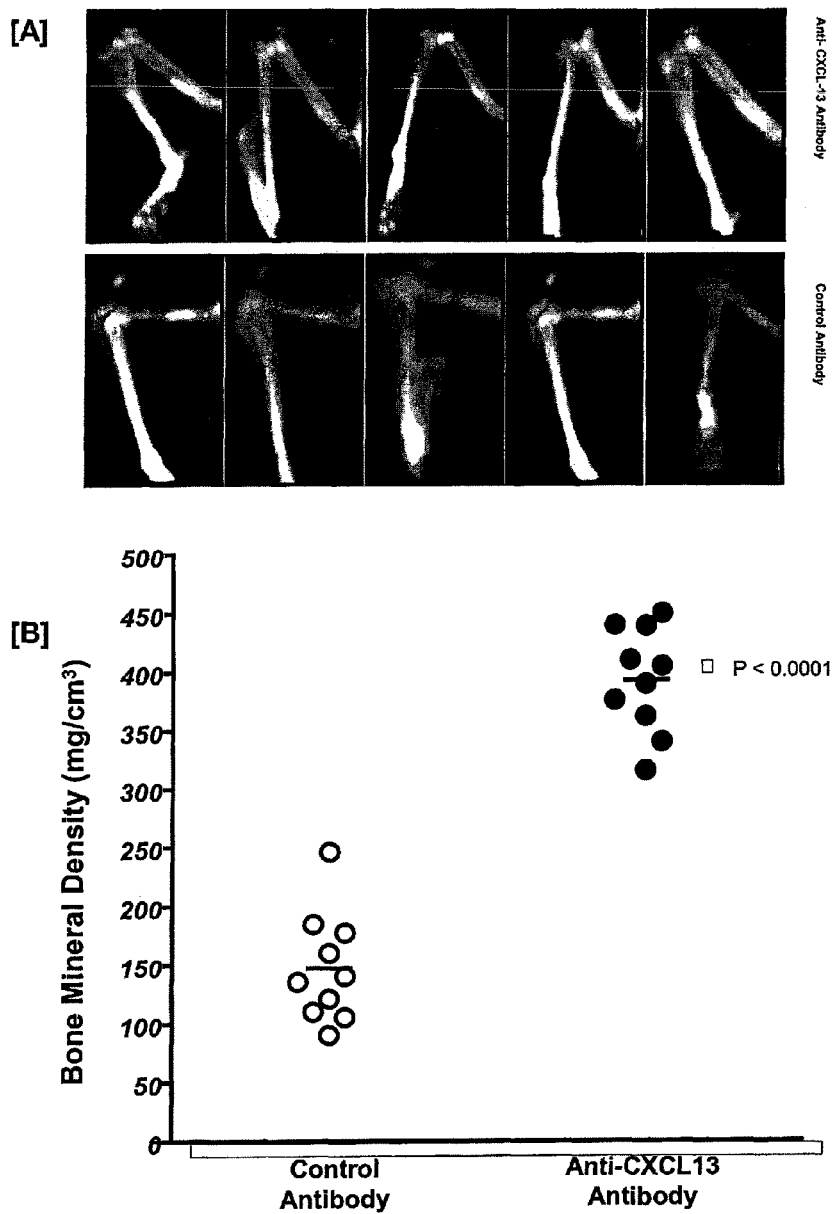
FIGS. 26A-B show that CXCL13 blockade inhibits loss of bone mineral density (BMD) induced by prostate cancer metastasis to bone.

FIGS. 26A-B demonstrate that CXCL13 blockade inhibits loss of bone mineral density (BMD) induced by prostate cancer bone metastasis. Male Nu/Nu mice were intra-tibially injected with $10^6$ of luciferase positive PC3 (PC3-luc) cell lines and tumors were allowed to develop for one week. Subsequently, the mice were intraperitoneally injected with 475 ug/kg isotype control or anti-CXCL13 antibody suspended in 100 ul of sterile saline every 72 hours for one week. Experimental groups were imaged 28 days post challenge using a Siemens microCT Scan System. FIG. 26A displays representative in mineral density images. FIG. 26B shows the moral diaphysis BMD (mg/cm$^3$) scans for each subject, which were quantified using MicroView software version 2.1.1 (General Electric Medical). Asterisk (*) indicates statistical significance (p<0.0001) between isotype control or anti-CXCL13 antibody-treated group.

Example 3

Detection of CXCL13 and CXCR5 Expression in Various Tumors

Figure 27:
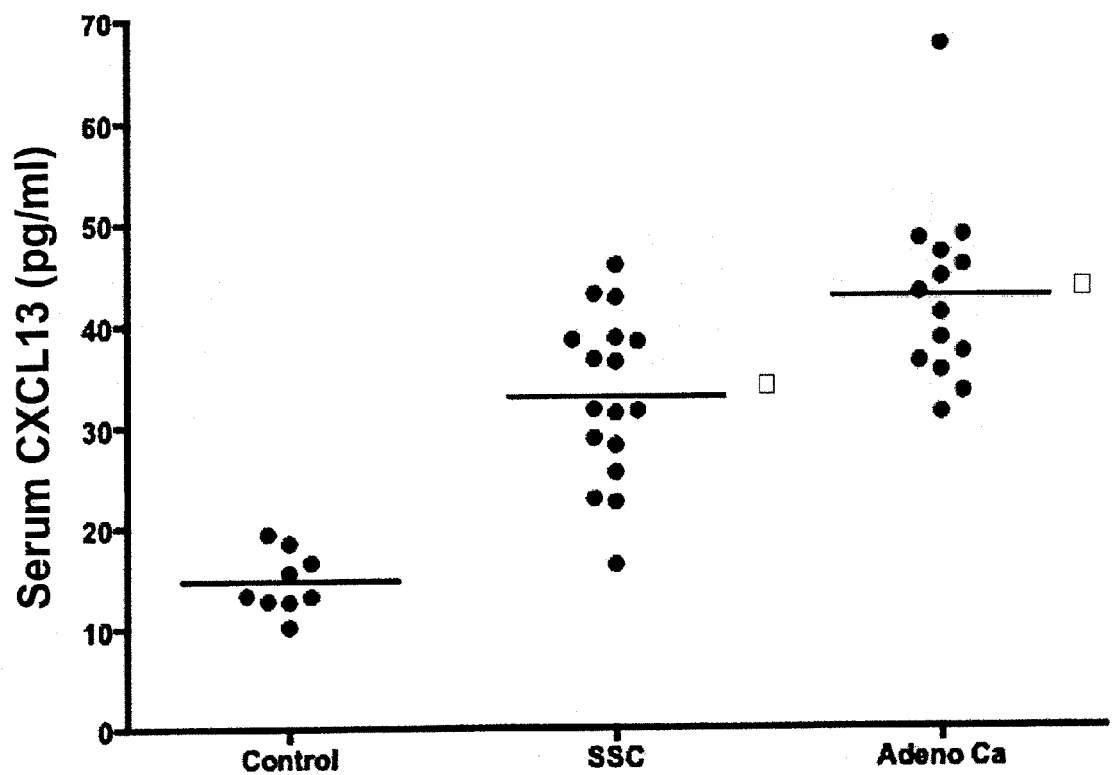
FIG. 27 depicts the levels of CXCL13 in serum of normal healthy controls and lung cancer subjects.

FIG. 27 shows CXCL13 levels in serum of normal healthy controls and lung cancer subjects. ELISA assays, capable of detecting >5 pg/mL of CXCL13, were performed to quantify CXCL13 levels se from normal healthy donors (n=9) or patients diagnosed with squamous cell carcinoma (SSC; n=17) or adenocarcinoma (Adeno Cu; n=14). Solid circles indicate individual serum CXCL13 levels and lines show median concentrations for each group. Asterisks (*) show significant differences (p<0.01) between normal healthy donor (i.e., control) or lung cancer patient serum samples.

Figure 28:
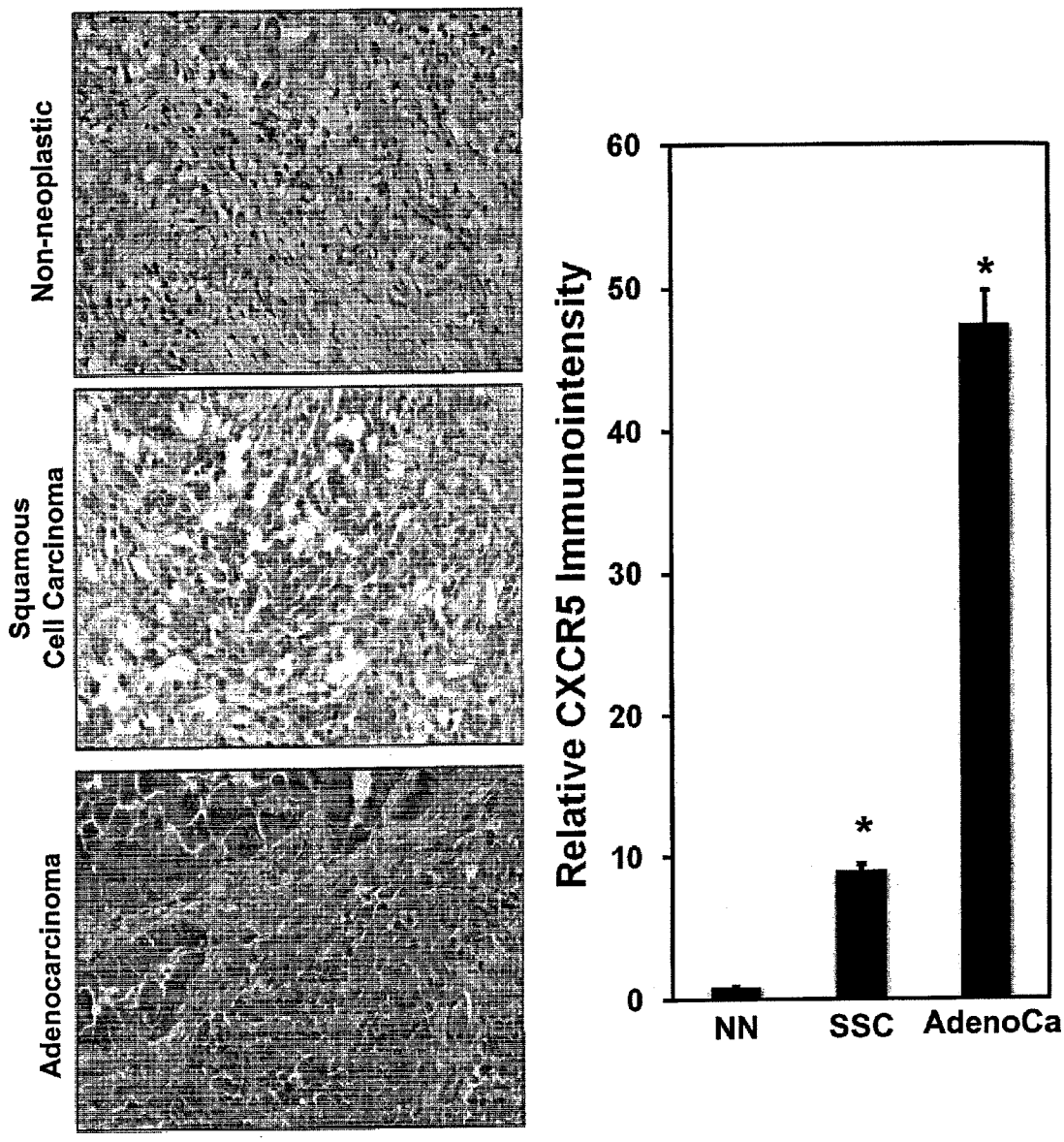
FIG. 28 shows CXCR5 expression by non-neoplastic lung and lung cancer tissue.

CXCR5 expression by non-neoplastic lung and lung cancer tissue is shown in FIG. 28. Lung tissue from non-neoplastic (NN; n=8), squamous cell carcinoma (SCC; n=24), and adenocarcinoma (AdenoCa; n=54) were stained with isotype control or anti-CXCR5 antibodies. Brown (DAB) color show CXCR5 staining. An Aperio ScanScope CS system with a 40x objective captured digital images of each slide. Representative cases are indicated and immuno-intensities of CXCR5 were quantified using image analysis Aperio ImageScope v.6.25 software. Asterisks (*) show significant differences (p<0.01) between non-neoplastic and lung cancer tissue.

Figure 29:
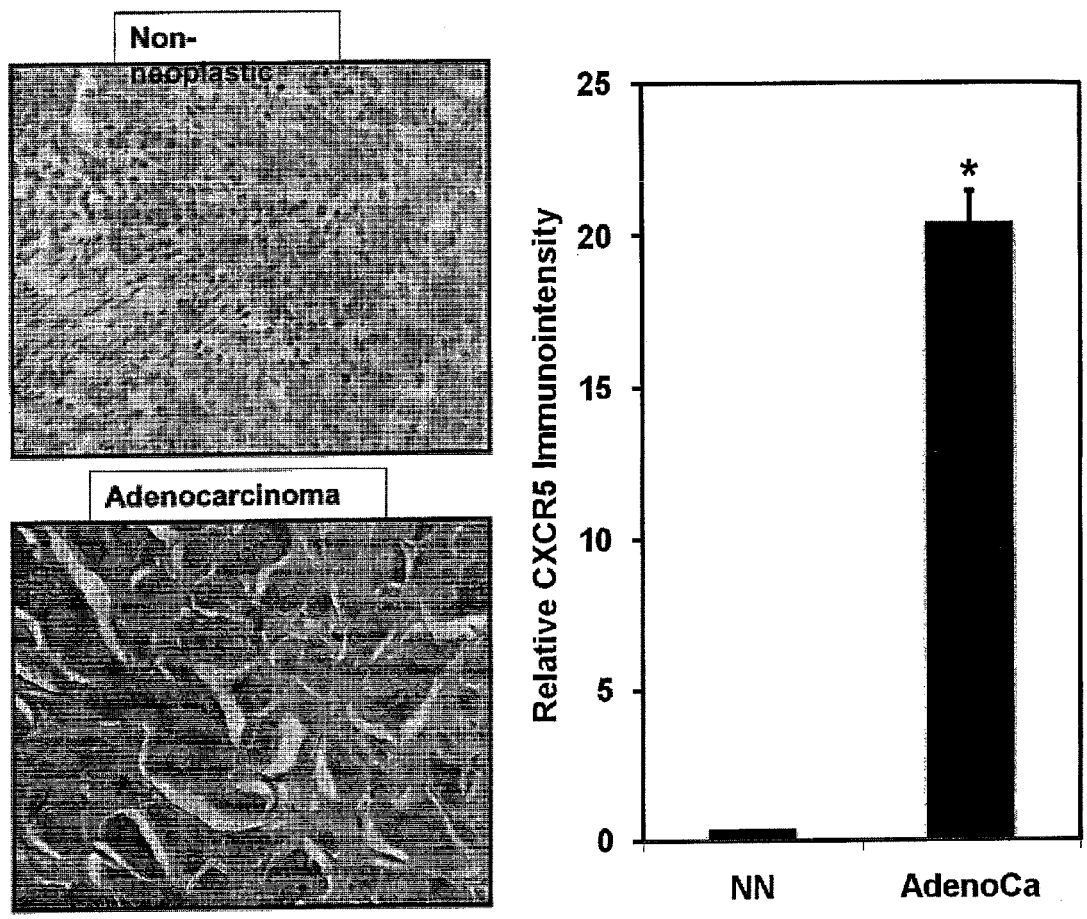
FIG. 29 shows CXCR5 expression by non-neoplastic mammary and breast cancer tissue.

FIG. 29 illustrates CXCR5 expression by non-neoplastic mammary and breast cancer tissue. Breast tissue from non-neoplastic (NN; n=8) and adenocarcinoma (AdenoCa; n=16) were stained with isotype control or anti-CXCR5 antibodies. Brown (DAB) color show CXCR5 staining. An Aperio ScanScope CS system with a 40× objective captured digital images of each slide. Representative cases are indicated and immuno-intensities of CXCR5 were quantified using image analysis Aperio ImageScope v.6.25 software. Asterisks/*) show significant differences (p<0.01) between non-neoplastic and cancerous tissue.

Figure 30:
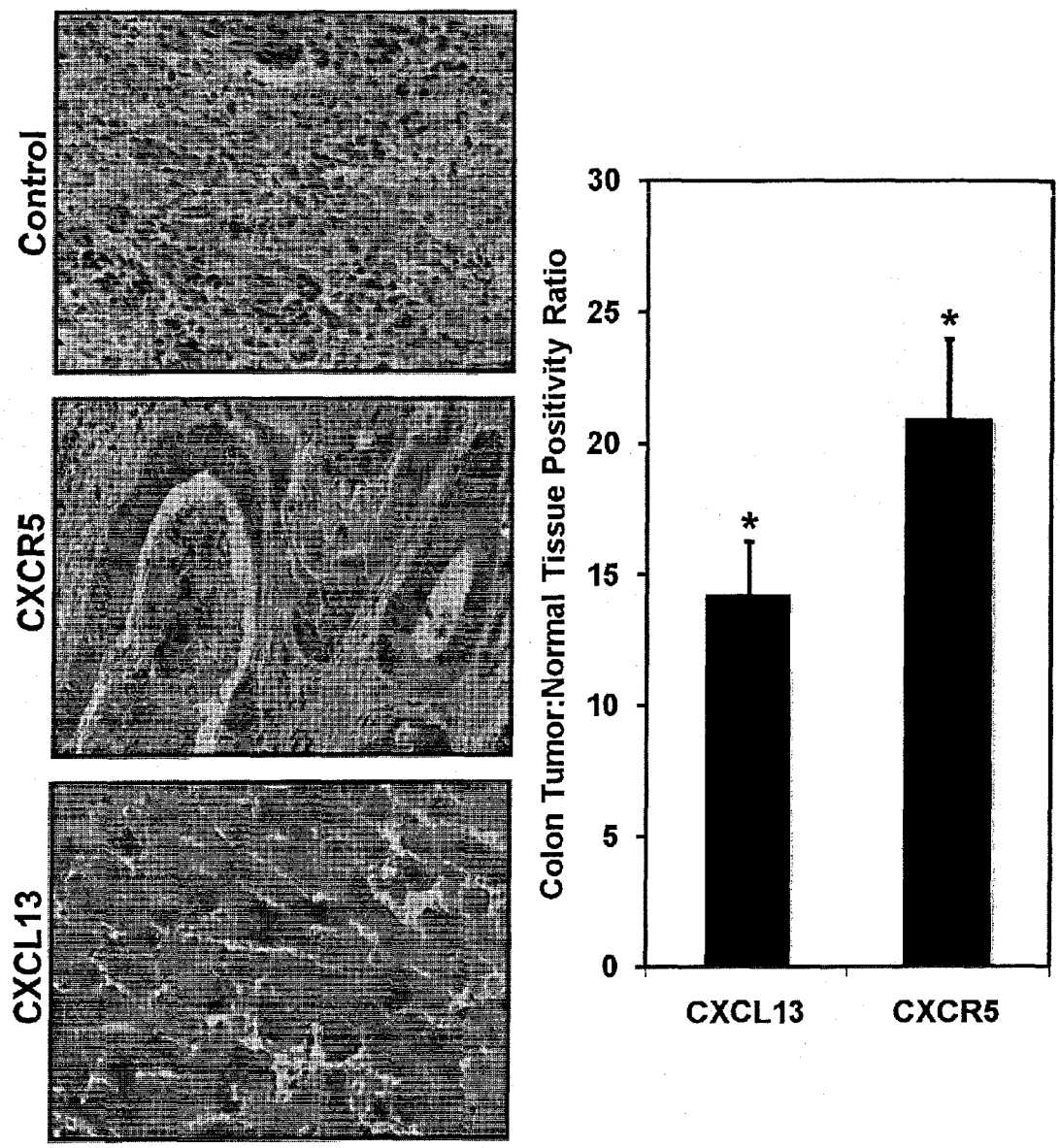
FIG. 30 is a depiction of CXCR5 and CXCL13 expression by colon cancer tissue relative to non-neoplastic controls.

CXCR5 and CXCL13 expression are also increased in colon cancer tissue relative to nonneoplastic controls, as shown in FIG. 30. Colon tissue from non-neoplastic (n=8) and adenocarcinoma (n=16) were stained with isotype control, anti-CXCR5, or anti-CXCL13 antibody. Brown (DAB) and magenta stain indicates CXCR5 and CXCL13 positivity, respectively. An Aperio ScanScope CS system with a 40× objective captured digital images. Representative cases are shown along with relative colon cancer to non-neoplastic control tissue immuno-intensities ratios of CXCR5 and CXCL13 that were quantified using Aperio ImageScope v.6.25 software. Asterisks (*) show significant differences (p<0.01) between non-neoplastic and cancerous tissue.

Figure 31:
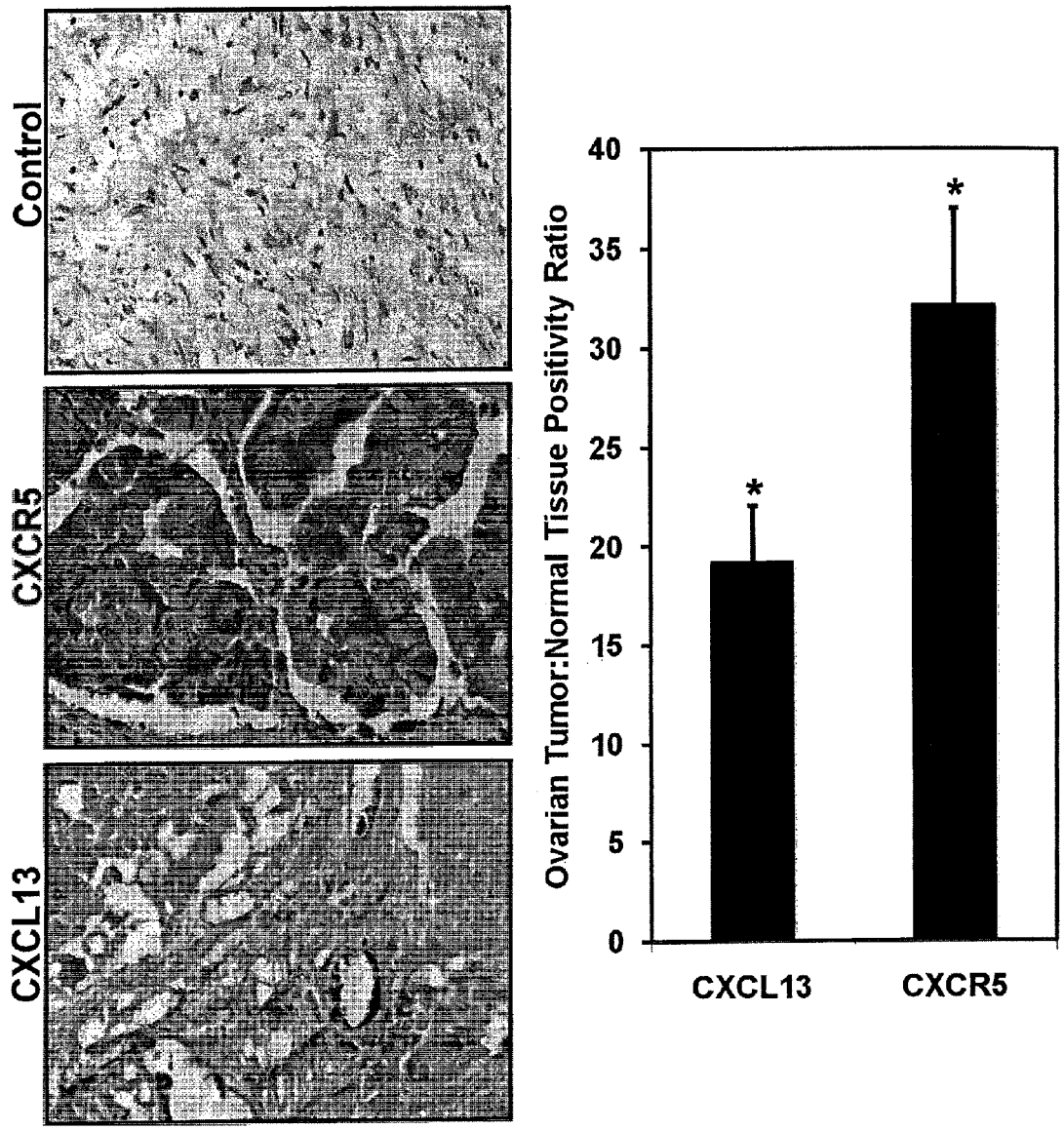
FIG. 31 is a depiction of CXCR5 and CXCL13 expression by ovarian cancer tissue relative to non-neoplastic controls.

It was also found that CXCR5 and CXCL13 expression by ovarian cancer tissue relative to nonneoplastic controls is significantly higher, as shown in FIG. 31. Ovarian tissue from non-neoplastic (n=8) and adenocarcinoma (n=16) were stained with isotype control, anti-CXCR5, or anti-CXCL13 antibody. Brown (DAB) and magenta stain indicates CXCR5 and CXCL13 positivity, respectively. Aperio ScanScope CS system with a 40× objective captured digital images. Representative cases are shown along with relative ovarian cancer to non-neoplastic control tissue immuno-intensities ratios of CXCR5 and CXCL13 that were quantified using Aperio ImageScope v.6.25 software. Asterisks (*) show significant differences (p<0.01) between non-neoplastic and cancerous tissue.

Example 4

Detecting Chemokine Expression Levels with Real Time-PCR Analysis Primer Design

Messenger RNA sequences for CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, CXCR1, CXCR2, CXCR3, CXCR4, CXCR5, CXCR5a, CXCR5b, CXCR6, CXCR7, CCL1, CCL2, CCL3, CCL4, CCL5, CCL6, CCL7, CCL8, CCL9, CCL10, CCL11, CCL12, CCL13, CCL14, CCL15, CCL16, CCL17, CCL18, CCL19, CCL20, CCL21, CCL22, CCL24, CCL25, CCL25-1, CCL25-2, CCL27, CCL28, CCR1, CCR2, CCR3, CCR4, CCR5, CCR6, CCR7, CCR8, CCR9, CCR10, CCR11, XCL1, XCL2, XCR1, CX3CR1, or CX3CL1 were obtained from the NIH-NCBI gene bank database. Primers were designed using the BeaconJ 2.0 computer program. Thermodynamic analysis of the primers was conducted using computer programs: Primer PremierJ and MIT Primer 3. The resulting primer sets were compared against the entire hu an genome to confirm specificity.

Real Time PCR Analysis

Cancer cell lines (ATCC, Rockville, Md.) were cultured in RMPI-1640 containing 10% fetal calf serum supplemented with non-essential amino acids, L-glutamate, and sodium pyruvate (complete media). Primary tumor and normal-paired matched tissues were obtained from clinical isolates (Clinomics Biosciences, Frederick, Md. and UAB Tissue Procurement, Birmingham, Ala.). Messenger RNA (mRNA) was isolated from $10^6$ cells using TriReagent (Molecular Research Center, Cincinnati, Ohio) according to manufacturer's protocols. Potential genomic DNA contamination was removed from these samples by treatment with 10 U/Fl of RNase free DNase (Invitrogen, San Diego, Calif.) for 15 minutes at 37° C. RNA was then precipitated and resuspended in RNA Secure (Ambion, Austin, Tex.). The cDNA was generated by reverse transcribing approximately 2 μg of total RNA using Taqman7 reverse transcription reagents (Applied Biosystems, Foster City, Calif.) according to manufacturer's protocols. Subsequently, cDNAs were amplified with specific human cDNA primers, to CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, CXCR1, CXCR2, CXCR3, CXCR4, CXCR5, CXCR5a, CXCR5b, CXCR6, CXCR7, CCL1, CCL2, CCL3, CCL4, CCL5, CCL6, CCL7, CCL8, CCL9, CCL10, CCL11, CCL12, CCL13, CCL14, CCL15, CCL16, CCL17, CCL18, CCL19, CCL20, CCL21, CCL22, CCL24, CCL25, CCL25-1, CCL25-2, CCL27, CCL28, CCR1, CCR2, CCR3, CCR4, CCR5, CCR6, CCR7, CCR8, CCR9, CCR10, CCR11, XCL1, XCL2, XCR1, CX3CR1, or CX3CL1 using SYBR7 Green PCR master mix reagents (Applied Biosystems) according to manufacturer's protocol. The level of copies of mRNA of these targets were evaluated by real-time PCR analysis using the BioRad Icycler and software (Hercules, Calif.).

The RT-PCR products obtained using CXCL1-, CXCL2-, CXCL3-, CXCL4-, CXCL5-, CXCL6-, CXCL7-, CXCL8-, CXCL9-, CXCL10-, CXCL11-, CXCL12-, CXCL13-, CXCL14-, CXCL15-, CXCL16-, CXCR1-, CXCR2-, CXCR3-, CXCR4-, CXCR5-, CXCR5a-, CXCR5b-, CXCR6-, CXCR7-, CCL1, CCL2-, CCL3-, CCL4-, CCL5-, CCL6-, CCL7-, CCL8-, CCL9-, CCL10-, CCL11-, CCL12-, CCL13-, CCL14-, CCL15-, CCL16-, CCL17-, CCL18-, CCL19-, CCL20-, CCL21-, CCL22-, CCL24-, CCL25-, CCL25-1-, CCL25-2-, CCL27-, CCL28-, CCR1-, CCR2-, CCR3-, CCR4-, CCR5-, CCR6-, CCR7-, CCR8-, CCR9-, CCR10-, CCR11-XCL1-, XCL2-, XCR1-, CX3CR1-, or CX3CL1-specific primer sets did not cross react with other gene targets due to exclusion of primers that annealed to host sequences (NIH-NCBI Genebank). The primers produced different size amplicon products relative the polymorphisms that resulted in CXCR5a versus CXCR5b and CCL25, CCL25-1, versus CCL25-2. To this end, RT-PCR analysis of adenoma, carcinoma, leukemia, lymphoma, melanoma, and/or myeloma cell lines and tumor tissue revealed that chemokines and chemokine receptors were differentially expressed by cancer cells.

Example 5

Anti-Chemokine and Anti-Chemokine Receptor Antibodies Inhibit Tumor Cell Growth In Vitro and In Vivo Anti-Sera Preparation The 15 amino acid peptides from CXCR1, CXCR2, CXCL1, CXCL2, CXCL3, CXCL5, CXCL6, CXCL7, CXCL8, CXCL12, CXCR5a, CXCR5b, CXCL13, CXCR6, CXCL16, CCL16, CCL25, CCL25-1, CCL25-2, CX3CR1, and CX3CL1 (SEQ ID NOS:1-21) were synthesized (Sigma Genosys, The Woodlands, Tex.) and conjugated to hen egg lysozyme (Pierce, Rockford, Ill.) to generate the antigen for subsequent immunizations for anti-sera preparation or monoclonal antibody generation. The endotoxin levels of chemokine peptide conjugates were quantified by the chromogenic *Limulus amebocyte* lysate assay (Cape Cod, Inc., Falmouth, Miss.) and shown to be <5 EU/mg. 100 μg of the antigen was used as the immunogen together with complete Freund's adjuvant Ribi Adjuvant system (RAS) for the first immunization in a final volume of 1.0 ml. This mixture was administered in 100 ml aliquots on two sites of the back of the rabbit subcutaneously and 400 ml intramuscularly in each hind leg muscle. Three to four weeks later, rabbits received 100 μg of the antigen in addition to incomplete Freund's adjuvant for 3 subsequent immunizations. Anti-sera were collected when anti-CXCR1, -CXCR2, -CXCL1, -CXCL2, -CXCL3, -CXCL5, -CXCL6-CXCL7, -CXCL8, -CXCL12, -CXCR5a, -CXCR5b, -CXCL13, -CXCR6, -CXCL16, -CCL16, -CCL25, -CCL25-1, -CCL25-2, -CX3CR1, and -CX3CL1 antibody titers reached 1:1,000,000. Subsequently, normal or anti-sera were heat-inactivated and diluted 1:50 in PBS.

Monoclonal Antibody Preparation

The 15 amino acid peptides from CXCR1, CXCR2, CXCL1, CXCL2, CXCL3, CXCL5, CXCL6, CXCL7, CXCL8, CXCL12, CXCR5a, CXCR5b, CXCL13, CXCR6, CXCL16, CCL16, CCL25, CCL25-1, CCL25-2, CX3CR1, and CX3CL1 were synthesized (Sigma Genosys) and conjugated to hen egg lysozyme (Pierce) to generate the "antigen" for subsequent immunizations for anti-sera preparation or monoclonal antibody generation. The endotoxin levels of chemokine peptide conjugates were quantified by the chromogenic *Limulus amebocyte* lysate assay (Cape Cod, Inc., Falmouth, Miss.) and shown to be <5 EU/mg. 100 μg of the antigen was used as the immunogen together with complete Freund's adjuvant Ribi Adjuvant system (RAS) for the first immunization in a final volume of 200 μl. This mixture was subcutaneously administered in 100 μl aliquots at two sites of the back of a rat, mouse, or immunoglobulin-humanized mouse. Two weeks later, animals received 100 μg of the antigen in addition to incomplete Freund's adjuvant for 3 subsequent immunizations. Serum were collected and when anti-CXCR1, -CXCR2, -CXCL1, -CXCL2, -CXCL3, -CXCL5, -CXCL6-CXCL7, -CXCL8, -CXCL12, -CXCR5a, -CXCR5b, -CXCL13, -CXCR6, -CXCL16, -CCL16, -CCL25, -CCL25-1, -CCL25-2, -CX3CR1, or -CX3CL1 antibody titers reached 1:2,000,000, hosts were sacrificed and splenocytes were isolated for hybridoma generation. Briefly, B cells from the spleen or lymph nodes of immunized hosts were fused with immortal myeloma cell lines (e.g., YB2/0). Hybridomas were next isolated after selective culturing conditions (i.e., HAT-supplemented media) and limiting dilution methods of hybridoma cloning. Cells that produce antibodies with the desired specificity were selected using ELISA. Hybridomas from normal rats or mice were humanized with molecular biological techniques in common use. After cloning a high affinity and prolific hybridoma, antibodies we e isolated from ascites or culture supernatants and adjusted to a titer of 1:2,000,000 and diluted 1:50 in PBS.

Anti-Sera or Monoclonal Antibody Treatment

Immunodeficient nude NIH-III mice (8 to 12 weeks old, Charles River Laboratory, Wilmington, Mass.), which lack T, B, and NK cells, received $1 \times 10^6$ cancer cells, subcutaneously, for the establishment of a tumor. The established solid tumor was then removed from the host for immediate implantation or stored in liquid nitrogen for later implantation. Freshly isolated or liquid nitrogen frozen tumor tissue (1 g) were surgically implanted in the intestinal adipose tissue for the generation of tumor. Once the xenografted tumor growth reached 5 mm in size, the NIH-III mice received 200 μl intraperitoneal injections of either anti-sera or monoclonal antibodies every three days and the tumor was monitored for progression or regression of growth.

Data Analysis

SigmaStat 2000 (Chicago, Ill.) software was used to analyze and confirm the statistical significance of data. The data were subsequently analyzed by the Student's t-test, using a two-factor, unpaired test. In this analysis, treated samples were compared to untreated controls. The significance level was set at $p<0.05$.

In Vitro Growth Studies

The adenoma, carcinoma, leukemia, lymphoma, melanoma, and/or myeloma cell lines were grown in complete media in the presence or absence of antibodies specific for CXCR1, CXCR2, CXCL1, CXCL2, CXCL3, CXCL5, CXCL6 CXCL7, CXCL8, CXCR4, CXCL12, CXCR5a, CXCR5b, CXCL13, CXCR6, CXCL16, CCL16, CCR9, CCL25, CCL25-1, CCL25-2, CX3CR1, or CX3CL1. The growth of cancer cell lines expressing CXCR1 and/or CXCR2 were inhibited by antibodies to CXCR1, CXCR2, CXCL1, CXCL2, CXCL3, CXCL5, CXCL6, CXCL7, or CXCL8. Similarly, the growth of cancer cell lines expressing CXCR4 were inhibited by antibodies to CXCR4 or CXCL12. The growth of cancer cell lines expressing CXCR5a or CXCR5b were inhibited by antibodies to CXCR5a, CXCR5b, or CXCL13. The proliferation of cancer cell lines expressing CXCR6 were inhibited by antibodies to CXCR6 or CXCL16. The growth of cancer cell lines expressing CCR9 were inhibited by antibodies to CCR9, CCL25, CCL25-1, or CCL25-2. The propagation of cancer cell lines expressing CX3CR1 were inhibited by antibodies to CX3CR1 or CXC3L1. Of interest, antibodies against the soluble ligands, CXCL1, CXCL2, CXCL3, CXCL5, CXCL6, CXCL7, CXCL8, CXCL12, CXCL13, CXCL16, CCL16, CCL25, CCL25-1, CCL25-2, or CX3CL1, were more effective at growth inhibition that those directed against the membrane receptors.

In Vitro Angiogenesis Studies

Microvascular endothelial cells (Cell Systems, Kirkland, Wash.) were grown according to supplier's protocols and allowed to form microvascular venules in an in vitro assay for angiogenesis (BD-Biocoat, Hercules, Calif.), in the presence or absence of antibodies specific for CXCR1, CXCR2, CXCL1, CXCL2, CXCL3, CXCL5, CXCL6, CXCL7, CXCL8, CXCR4, CXCL12, CXCR5a, CXCR5b, CXCL13, CXCR6, CXCL16, CCL16, CCR9, CCL25, CCL25-1, CCL25-2, CX3CR1, or CX3CL1. The angiogenesis was inhibited by antibodies against CXCR1, CXCR2, CXCL1, CXCL2, CXCL3, CXCL5, CXCL6, CXCL7, CXCL8, CXCR4, CXCL12, CXCR6 or CXCL16.

In Vivo Growth Studies

Cancer cell lines or primary tumor tissue were adoptively transferred into NIH-III mice and allowed to form the xenograft tumor of interest. Antibodies directed against CXCR1, CXCR2, CXCL1, CXCL2, CXCL3, CXCL5, CXCL6, CXCL7, CXCL8, CXCR4, CXCL12, CXCR5a, CXCR5b, CXCL13, CXCR6, CXCL16, CCL16, CCR9, CCL25, CCL25-1, CCL25-2; CX3CR1, or CX3CL1 differentially affected the progression and regression of tumor size. In certain cases, antibodies directed towards CXCR1, CXCR2, CXCL1, CXCL2, CXCL3, CXCL5, CXCL6, CXCL7, CXCL8, CXCR4, CXCL12, CXCR6 or CXCL16 effectively lead to both regression and impeding progression of tumor growth. Antibodies directed against CXCR4, CXCL12, CXCR5a, CXCR5b, CXCL13, CCL16, CCR9, CCL25, CCL25-1, CCL25-2, CX3CR1, or CX3CL1 were effective at inhibiting the progression of tumor size.

The protein sequences of the chemokines used herein are recorded in NIH-NCBI GenBank as: (1) CXCR1 (ACCESSION# NP 000625), SEQ ID NO:1, (2) CXCR2 (ACCESSION# NP 001548), SEQ ID NO:2, (3) CXCL1 (ACCESSION# NP 001502), SEQ ID NO:3, (4) CXCL2 (ACCESSION# NP 002080), SEQ ID NO:4, (5) CXCL3 (ACCESSION# NP 002081), SEQ ID NO:5, (6) CXCL5 (ACCESSION# NP 002985), SEQ ID NO:6, (7) CXCL6 (ACCESSION# NP 002984), SEQ ID NO:7, (8) CXCL7 (ACCESSION# NP 002695). SEQ ID NO:8, (9) CXCL8 (IL-8, ACCESSION# NP 000575), SEQ ID NO:9, (10) CXCR4 (ACCESSION# NP 003458), SEQ ID NO:10, (11) CXCL12 (ACCESSION# NP 000600), SEQ ID NO:11, (12) CXCR5A (ACCESSION# NP 116743), SEQ ID NO:12, (13) CXCR5B (ACCESSION# NP 001707), SEQ ID NO:13, (14) CXCL13 (ACCESSION# NP 006410), SEQ ID NO:14, (15) CXCR6 (ACCESSION# NP 006555), SEQ ID NO:15, (16) CXCL16 (ACCESSION# NP 071342), SEQ ID NO:16, (17) CCL16 (ACCESSION# NP 004581), SEQ ID NO:17, (18) CCL25 (ACCESSION# NP-005615.2), SEQ ID NO:18, (19) CCL25-1 (ACCESSION# NP 005615), SEQ ID NO:19, (20) CCL25-2 (ACCESSION# NP 683686), SEQ ID NO:20, (21) CX3CR1 (ACCESSION# NP 001328), SEQ ID NO:21, and (22) CX3CL1 (ACCESSION # NP 002987), SEQ ID NO:22.

The cDNA sequences are known and are available in NIH-NCBI GenBank under the following accession numbers: (23) CXCR1 (ACCESSION# NM 000634), SEQ ID NO:23, (24) CXCR2(ACCESSION# NM 001557), SEQ ID NO:24, (25) CXCL1 (ACCESSION# NM 001511), SEQ ID NO:25, (26) CXCL2 (ACCESSION# NM 002089), SEQ ID NO:26, (27) CXCL3 (ACCESSION# NM 002090), SEQ ID NO:27, (28) CXCL5 (ACCESSION# NM 002994), SEQ ID NO:28, (29) CXCL6 (ACCESSION# NM 002993), SEQ ID NO:29, (30) CXCL7 (ACCESSION# NM 002704), SEQ ID NO:30, (31) CXCL8 (IL-8, ACCESSION# NM 000584), SEQ ID NO:31, (32) CXCR4 (ACCESSION# NM 003467), SEQ ID NO:32, (33) CXCL12 (ACCESSION# NM 000609), SEQ ID NO:33, (34) CXCR5A (ACCESSION# NM 032966), SEQ ID NO:34, (35) CXCR5B (ACCESSION# NM 001716), SEQ ID NO:35, (36) CXCL13 (ACCESSION# NM 006419), SEQ ID NO:36, (37) CXCR6 (ACCESSION# NM 006564), SEQ ID NO:37, (38) CXCL16 (ACCESSION# NM 022059), SEQ ID NO:38, (39) CCL16 (ACCESSION# NM 004590), SEQ ID NO:39, (40) CCL25 (ACCESSION# NM 005624.3), SEQ ID NO:40, (41) CCL25-1 (ACCESSION# NM 005624), SEQ ID NO:41, (42) CCL25-2 (ACCESSION# NM 148888), SEQ ID NO:42, (43) CX3CR1 (ACCESSION# NM 001337), SEQ ID NO:43, and (44) CX3CL1 (ACCESSION# NM 002996), SEQ ID NO:44.

As shown in the table below, the particular chemokines which are most which any tumor expresses may vary. The methods of the present invention may be customized for a particular patient, depending on the chemokines over-expressed by the patient's own tumor. It is possible to identify the particular chemokines which are over-expressed in the tumor using methods of the invention and administer antibodies against that over-expressed chemokine. The tailoring of treatment for the cancer patient is novel, and is a particularly valuable aspect of the invention.

TABLE 3 indicates the differing amounts of particular chemokines over-expressed in particular tumors that were studied.

TABLE 3

| | Chemokine | Chemokine Receptor |
|---|---|---|
| Carcinoma | CCL1, CCL2, CCL4, CCL17, CCL19, CCL21, CCL22, CCL25 | CCR2, CCR7, CCR8, CCR9 |
| | CXCL12, CXCL13, CXCL16 | CXCR4, CXCR5, |
| | CX3CL1 | CXCR6 CX3CR1 |
| Leukemia | CCL1, CCL4, CCL17, CCL19, CCL21, CCL22, CCL25 | CCR7, CCR8, CCR9 |
| | CXCL12 | CXCR4, CXCR7 |
| Lymphoma | CXCL12, CXCL13 | CXCR4, CXCR5 |
| Melanoma | CCL25, CCL27 | CCR9, CCR10 |
| | CXCL1, CXCL2, CXCL3, CXCL5, CXCL6, CXCL7, CXCL8, CXCL12, CXCL13, CXCL16 | CXCR1, CXCR2, CXCR4, CXCR5, CXCR6, CXCR7 |
| | CX3CL1 | CX3CR1 |
| Sarcoma | CCL1, CCL3, CCL4, CCL5, CCL7, CCL8, CCL11, CCL13, CCL17, CCL22, CCL24 | CCR3, CCR5, CCR8 |
| | CXCL12 | CXCR4, CXCR7 |
| | CX3CL1 | CX3CR1 |

Example 6

CXCR5-CXCL13 Induced Anti-Apoptotic and/or Survival Signal Involved in PCa Chemo Resistance LNCaP (hormone responsive, wild type p53 expression), PC3 (hormone refractory, p53 null), and DU145 (hormone refractory, p53 mutated) cell lines are grown with or without CXCL16 and with or without doxorubicin (1 µM/2 µM/4 µM), etoposide (20 µM/40 µM), estramustine (4 µM/10 µM), or docetaxel (10 nM/20 nM/40 nM) for 4, 8, 12, and 24 hours. Expression and activation of cell survival, pro- and anti-apoptotic signals (Akt, Src, Ca KII, FAK, FKHR, FOXO, CREB, NF-κB, Myc, Fos, Jun Apaf1, Bax, Bcl2, BclX$_L$, BaK, Bad, Bik, Bim, TP53, Caspase-3, -6, -8, -9, survivin, vitronectin, β-Catenin) and molecules responsible for drug resistance or metabolism (Twist-1, Snail-1, Glutathione-S-transferase-π (GST-π), p53, topoisomerase I, IIα, IIβ, and ABC drug transporters) are accessed by real-time PCR and Western blot. Briefly, after treatment of cells, changes in the gene expression is tested using real-time PCR. Activation of signaling molecules is also be tested by phosphorylation specific antibody (i.e., Western blot analysis). To further confirm the role of the activated signaling molecules, following CXCL16 treatment, expression or activity of the candidate molecules is inhibited using chemical inhibitors or siRNAs and target genes are analyzed by real-time PCR and Western blot analysis. Subsequently, the response of treated cells to chemotherapeutic drugs is evaluated by Vybrant apoptosis assay (Molecular probes) kit.

RNA Isolation and Real-Time PCR

Total RNA is isolated by TRIZOL™ (Invitrogen) method and quantified by UV spectrophotometry. Quality of RNA is analyzed by electrophoresis. The cDNA synthesis is completed using the ISCRIPT™ cDNA synthesis kit (BioRad) as described by the manufacturer. Real-time PCR is performed using IQ™ SYBR green supermix (BioRad) as described by manufacturer and specific primers designed against FAK, FKHR, FOXO, Apaf1, Bax, Bcl2, BclX$_L$, BaK, Bad, Bid, XIAP, Bik, Bim, TP53, cytochrome C, Caspase-3, -6, -8, -9, survivin, lamin, CamKII, vitronectin, β-Catenin, cadherins, Twist-1, Snail-1, CREB, NF-κB, Myc, Fos, Jun, β-actin and GAPDH. The results are calculated by delta Ct to quantify fold changes in mRNAs compared to untreated groups.

Western Blotting

Cells are harvested and resuspended in lysis buffer to extract total protein. Lysis buffer contains 50 mM Tris-HCl, pH 7.4, 150 mM NaCl, 1% Triton X-100, 1% deoxycholate, 0.1% SDS, 5 mM EDTA supplemented with protease inhibitors, 1 mM phenylmethylsulphonylfluoride, 1 mM benzamidine, 10 µg/mL soybean trypsin inhibitor, 50 µg/mL leupeptin, 1 µg/mL pepstatin and 20 µg/mL aprotinin. Cell lysates are stored on ice for 30 min, centrifuged (14000×g) for 20 min at 4° C., and supernatant is used for Western blot analysis of genes demonstrating significant modulation in mRNA level. Similarly, phosphor-specific antibodies are used to test changes in the level of phosphorylation of Akt1/2/3, mTOR, FAK, FKHR, FOXO, and GSK-3β. Moreover, activation of caspases and PARP, following cleavage are evaluated using specific antibodies. The results obtained after chemiluminescent detection of protein bands by ECL plus reagent (Pharmecia) on X-ray film is normalized to β-actin and/or GAPDH using Image J image analysis software (NIH).

Detection of Cytochrome C Release

Cells are collected and washed in PBS, and resuspended in extraction buffer containing 220 mM mannitol, 68 mM sucrose, 50 mM PIPES-KOH, pH 7.4, 50 mM KCl, 5 mM EGTA, 2 mM $MgCl_2$, 1 mM DTT, and protease inhibitors. After 30 min incubation on ice, cells are homogenized using Glass-Teflon homogenizer and homogenates will be spun at 14,000 g for 15 mM. Cytosolic extracts are used for Western blot analysis using anti-cytochrome C monoclonal antibody (PharMingen).

siRNA Transfection, Chemical Inhibitor, and Apoptosis Detection

Prostate cancer cell lines are transfected with gene specific and nonspecific control siRNAs (Dharmacon) using LipofectAMINE 2000 (Invitrogen). Optimum gene knock-down time and siRNA concentration are confirmed by Western blot analysis and further evaluated for cell survival following drug treatment with or without CXCL16, control antibody, and/or anti-CXCR6 antibody. The detection of changes in live, apoptotic, and necrotic cells is evaluated as follows: cell survival is tested by Vybrant apoptosis as described by the manufacturer (Molecular probe), using FACScan flow cytometer and CELLQUEST™ software (BD Phammingen). Change in down-stream gene expression after gene knockdown is tested using real-time PCR and western blotting.

Cells treated with CXCL13 show enhanced expression of cell survival and drug transporter proteins which show differences in their expression pattern in hormone responsive and non responsive cells. Anti-CXCL13 Abs effectively reverse the effect of CXCL13 in PCa cells. Doxorubicin, estramustine, etoposide and docetaxel induce apoptosis in PCa cells without CXCL13 treatment (or CXCR5 blockade).

Example 7

CXCR5-CXCL13 Induced Changes in ABC Drug Transporters

LNCaP, PC3, and DU145 cells are grown with or without CXCL13, control antibody, and/or anti-CXCR5 antibodies along with or without doxorubicin, estramustine, etoposide or docetaxel for 4, 8, 12 or 16 hours as described earlier. After treatment, changes in the ABC transporter and Twist-1 mRNA expression are quantified by real-time PCR, as described above, using specific primers directed for ABC and Twist-1 cDNA. The genes demonstrating significant alterations in mRNA expression are further tested by Western blot analysis. Nuclear extracts from treated cells are evaluated by chromatin immuno-precipitation (ChIP) assay to determine whether the transcriptional factors induced by CXCL13 bind the promoter region of ABC transporters and Twist-1.

Chromatin Immuno-Precipitation (ChIP)

The results from Example 4 provide information about the genes that are regulated as well as those that may modulate transcription factors activated by CXCR5-CXCL13 interaction. Based on these results, target transcription factors and genes are selected. Specific PCR primers are designed against the promoter region of these genes containing the binding sites of transcription factors. PCR primer are used to amplify the DNA being precipitated along with transcription factors. Cells are harvested by trypsinization in the presence of 20 mM butyrate. 50,000 cells are re-suspended in 500 µl PBS/butyrate. Proteins and DNA are cross-linked with 1% formaldehyde for 8 min at room temperature and cross-linking is stopped with 125 mM glycine for 5 min. Cells are centrifuged at 470 g in a swing-out rotor with soft deceleration settings for 10 min at 4° C. and washed twice in 0.5 ml ice-cold PBS/butyrate by vortexing followed by centrifugation. Cells are lysed by addition of lysis buffer (50 mM Tris-HCl, pH 8, 10 mM EDTA, 1% SDS, protease inhibitor cocktail (Sigma-Aldrich), 1 mM PMSF, 20 mM butyrate, vortexing and subsequent centrifugation. This procedure is known to produce chromatin fragments of 500 bp. The sonicated lysate is diluted 8-fold in RIPA buffer containing a protease inhibitor cocktail, 1 mM PMSF, and 20 mM butyrate (RIPA ChIP buffer). RIPA ChIP buffer (330 µl) is added to the pellet and mixed by vortexing. Immunoprecipitation and washes of the ChIP material is accomplished by the use of antibody-directed against specific transcription factors. Chromatin is aliquoted into tubes containing antibody-bead complexes. Input sample is placed in a tube for phenol-chloroform isoamyl alcohol isolation. The immunoprecipitated material is washed three times and transferred into a new tube while in TE. DNA elution in 1% SDS, cross-link reversal and proteinase K digestion is carried out in a single step for 2 hrs at 68° C. DNA is extracted with phenol-chloroform isoamylalcohol, and ethanol-precipitation in presence of acrylamide carrier (Sigma-Aldrich) and dissolved in TE. Immunoprecipitated DNA from 3-4 independent ChIPs is analyzed by real time PCR. Real-time PCR data is expressed as percent (±SD) precipitated (antibody-bound) DNA relative to input DNA, in three independent replicate ChIP assays.

Phosphorylation and activation of transcription factors such as CREB, Fos, Jun, and NFkB via CXCR5-CXCL13 signaling subsequently leads to increases in expression of ABC transporters and Twist-1. Decreases in gene expression are observed if negative regulatory elements are present in the same promoter. Since hormone-dependent and refractory PCa cells have differences in the expression of these intracellular signaling molecules, they show variations in genes to be modulated by hormone dependent and refractory conditions. The modulation in gene expression shows differences with drug treatment in presence of CXCL13 and in absence of CXC L13 treatment.

Example 8

In Vivo Evaluation of CXCL13:CXCR5-Directed Therapy

Male nude mice are subcutaneously challenged by luciferase expressing androgen responsive (LNCaP-Luc) and non-responsive (PC3-Luc) cells. Tumor development is measured non-invasively using in vivo imaging system. After establishment of a measurable tumor, mice are divided into treatment (A, B, C, D and E) and control groups (F, G, H, I, J and K). Group "A" receives CXCL13 or CXCR5 neutralizing antibodies (12.5 mg/kg/day) every alternate day and controls (group F) receive isotype control antibodies (12.5 mg/kg/day). Group "B," "C," "D" and "E" receive CXCL13 or CXCR5 neutralizing antibodies (12.5 mg/kg/day) with intra-peritoneal injection of doxorubicin (5 mg/kg/day on days 1 to 3 followed by administration on days 15 to 17), intravenous injection of etoposide (10 mg/kg/day; on day 1, 5, 9, 14, 19 and 24), intravenous injection of estramustine (4 g/kg/day on day 1-5 and day 26-31), or intraperitoneal injection of docetaxel (8 mg/kg/day twice a week for 4 weeks), respectively. Controls for these treatment groups ("G," "H," "I" and "J," respectively) receive theses drugs using similar concentration and injection protocol with isotype control antibodies (12.5 mg/kg/day). Group "K" receives PBS and serves as placebo. Tumor progression and regression in treatment and controls are evaluated by non-invasive in vivo imaging. The tumor from treated groups and untreated control groups is excised and evaluated for the changes in the cell survival and drug resistance proteins by immunohistochemistry.

Statistics (Significance) and Sample Size

Sample size (or power) calculations are relevant to the design of preliminary studies and determining the requirements for proposed experiments. To interpret our results, significance tests and statistical analysis are also critical. The traditional α-value, i.e., p=0.01, is used to evaluate the statistical significance of this study. The proposed experiment will require a minimum of 10 mice per group. The data is expressed as the mean±SEM and compared using a two-tailed paired (or unpaired) students t-test for normally distributed samples or an unpaired Mann Whitney U test as a non-parametric test for samples not normally distributed. The results are analyzed using SYSTAT (Systat Software Inc.) statistical program. Single-factor and two-factor variance ANOVA analyses are used to evaluate groups and subgroups, respectively. Hence, results are considered statistically significant if p values are <0.05.

Animals

Six to eight week old male nude mice are subcutaneously injected with PCa cells. Briefly, 5×10$^6$ Luciferase expressing PC3 cells are resuspended in 100 µl of sterile PBS and injected into the flanks of nude mice under isoflurane anesthesia. Luciferase expressing LNCaP cells (5×10$^6$ cell) are mixed with 50% Matrigel (Becton Dickinson) and injected in the flanks of nude mice under isoflurane anesthesia.

Analysis of In Vivo Tumor Growth

Tumor bearing nude mice receive 150 mg/kg D-Luciferin (Xenogen) by intra-peritoneal injection Using 25×5/8 inch gauge needle 15 minutes before imaging. The mice are imaged using the IVIS100 in vivo imaging system and results expressed in photons/sec/cm$^2$/sr. Tumor volume is measured by use of calipers and calculated by the formula (Larger diameter)×(smaller diameter)$^2$×0.5.

Cell Survival, Apoptotic and Drug Resistant Gene Expression Analysis

Tumors from all groups are excised three days after completion of treatment protocols. Tumors are fixed in 4% PFA and embedded in paraffin. Paraffin sections (thickness 7 µm) are mounted on glass slides, deparaffinized and re-hydrated (Xylene for 5 min; absolute, 95% and 70% ethanol for 1 min each). The rehydrated sections are used for peroxidase based immunohistochemical staining for drug transporters, PI3K, Akt, FAK, FKHR, FOXO, Apaf1, Bax, Bcl2, BclXL, BaK, Bad, Bid, XIAP, Bik, Bim, TP53, Cytochrome C, Caspase-3, -6, -8, -9, survivin, lamin, CamKII, vitronectin, β-Catenin, cadherins, Twist-1, CREB, NF-κB, Myc, Fos, Jun, CXCR5 and CXCL13. After staining, slides are scanned and analyzed by the Aperio scanscope (Aperio) system.

CXCL13 neutralization leads to decreased cell survival in response to drugs, thus reduction of tumor volume. However, the response also varies among the tumors formed by hormone sensitive (LNCaP) and hormone refractory (PC3 cells). Further, chemotherapeutic drugs have lower efficacy in the tumors with a functional CXCR5-CXCL13 axis, which may enhance the expression of ABC proteins known to transport these drugs out of the cell.

The above description is for the purpose of teaching the person of ordinary skill in the art how to practice the present invention, and is not intended to detail all those obvious modifications and variations of it that will become apparent to the skilled worker upon reading the description. It is intended, however, that all such obvious modifications and variations be included within the scope of the present invention, which is defined by the following claims. The claims are intended to cover the components and steps in any sequence that is effective to meet the objectives there intended, unless the context specifically indicates the contrary. All the references cited in the specification are herein incorporated by reference in their entirely.

What is claimed is:

1. A method for treating cancer in a subject, comprising: administering to said subject a therapeutically effective amount of an anti-CXCL13 antibody, or an anti-CXCR5 antibody, or a combination thereof, wherein said cancer is prostate cancer, and wherein said anti-CXCL13 antibody, or said anti-CXCR5 antibody, or said combination of anti-CXCL13 antibody and said anti-CXCR5 antibody is given in a dosage range of 1 ng/kg body weight/day to about 100 mg/kg body weight/day.

2. The method of claim 1, wherein said anti-CXCL13 antibody, or anti-CXCR5 antibody, or a combination thereof is administered directly into a cancerous tissue.

3. The method of claim 1, wherein said anti-CXCL13 antibody, or anti-CXCR5 antibody, or a combination thereof is administered in conjunction with a chemotherapeutic agent.

4. The method of claim 1, wherein said anti-CXCL13 antibody, or said anti-CXCR5 antibody, or a combination thereof is administered in conjunction with one or more antibodies that bind specifically to one or more chemokines or chemokine receptors selected from the group consisting of CCL1, CCL2, CCL4, CCL17, CCL19, CCL21, CCL22, CCL25, CXCL12, CXCL16, CCR2, CCR7, CCR8, CCR9, CXCR4, CXCR6, CX3CL1 and CX3CR1.

5. The method of claim 1, further comprising: determining the level of CXCL13 and/or CXCR5 expression in a tissue from said subject, and, if an increased level of CXCL13 and/or CXCR5 is detected, administering to said subject a therapeutically effective amount of said anti-CXCL13 antibody, said anti-CXCR5 antibody, or a combination thereof.

6. The method of claim 1, wherein said anti-CXCL13 antibody, or said anti-CXCR5 antibody, or said combination of anti-CXCL13 antibody and said anti-CXCR5 antibody is given in a dosage range of 1 ng/kg body weight/day to about 100 ng/kg body weight/day.

7. The method of claim 1, wherein said anti-CXCL13 antibody, or said anti-CXCR5 antibody, or said combination of anti-CXCL13 antibody and said anti-CXCR5 antibody is given in a dosage range of 10 ng/kg body weight/day to about 1 μg/kg body weight/day.

8. The method of claim 1, wherein said anti-CXCL13 antibody, or said anti-CXCR5 antibody, or said combination of anti-CXCL13 antibody and said anti-CXCR5 antibody is given in a dosage range of 100 ng/kg body weight/day to about 10 μg/kg body weight/day.

9. The method of claim 1, wherein said anti-CXCL13 antibody, or said anti-CXCR5 antibody, or said combination of anti-CXCL13 antibody and said anti-CXCR5 antibody is given in a dosage range of 1 μg/kg body weight/day to about 100 μg/kg body weight/day.

10. The method of claim 1, wherein said anti-CXCL13 antibody, or said anti-CXCR5 antibody, or said combination of anti-CXCL13 antibody and said anti-CXCR5 antibody is given in a dosage range of 10 μg/kg body weight/day to about 1 mg/kg body weight/day.

11. The method of claim 1, wherein said anti-CXCL13 antibody, or said anti-CXCR5 antibody, or said combination of anti-CXCL13 antibody and said anti-CXCR5 antibody is given in a dosage range of 100 μg/kg body weight/day to about 10 mg/kg body weight/day.

12. A method for prevention or inhibition of the migration or metastasis of cancer cells with elevated expression of CXCL13 and/or CXCR5 in a subject, comprising: administering to the subject a therapeutically effective amount of an anti-CXCL13 antibody, or an anti-CXCR5 antibody, or a combination thereof, wherein said anti-CXCL13 antibody, or said anti-CXCR5 antibody, or said combination of anti-CXCL13 antibody and said anti-CXCR5 antibody is given in a dosage range of 1 ng/kg body weight/day to about 100 mg/kg body weight/day;
wherein said cancer cells are prostate cancer cells.

13. A method for enhancing the effect of chemotherapy, comprising:
    administering to a subject who is under chemotherapy for a cancer, an effective amount of an anti-CXCL13 antibody, or an anti-CXCR5 antibody, or a combination thereof,
    wherein said cancer is prostate cancer.

* * * * *